(12) United States Patent
Bhanot et al.

(10) Patent No.: US 7,825,235 B2
(45) Date of Patent: Nov. 2, 2010

(54) MODULATION OF DIACYLGLYCEROL ACYLTRANSFERASE 2 EXPRESSION

(75) Inventors: Sanjay Bhanot, Carlsbad, CA (US); Kenneth W. Dobie, Del Mar, CA (US); Xing-Xian Yu, San Diego, CA (US); Brett P. Monia, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 352 days.

(21) Appl. No.: 10/643,801

(22) Filed: Aug. 18, 2003

(65) Prior Publication Data

US 2005/0043524 A1    Feb. 24, 2005

(51) Int. Cl.
*C07H 21/04* (2006.01)
(52) U.S. Cl. ..................................... 536/24.5
(58) Field of Classification Search ................. 536/24.5
See application file for complete search history.

(56) References Cited

U.S. PATENT DOCUMENTS

| | | | |
|---|---|---|---|
| 5,801,154 A | 9/1998 | Baracchini | |
| 5,837,542 A | 11/1998 | Grimm et al. | |
| 5,998,148 A | 12/1999 | Bennett et al. | |
| 6,083,695 A * | 7/2000 | Hardin et al. | 435/6 |
| 6,100,077 A | 8/2000 | Sturley et al. | |
| 6,127,533 A | 10/2000 | Cook | |
| 6,284,538 B1 * | 9/2001 | Monia et al. | 435/375 |
| 6,344,548 B1 | 2/2002 | Farese, Jr. et al. | |
| 6,444,427 B1 | 9/2002 | Ludwig et al. | |
| 6,512,099 B2 | 1/2003 | Omura et al. | |
| 6,582,908 B2 | 6/2003 | Fodor et al. | |
| 6,605,451 B1 * | 8/2003 | Marmaro et al. | 435/91.2 |
| 6,607,893 B2 | 8/2003 | Ramharack et al. | |
| 6,822,141 B2 | 11/2004 | Lardizabal et al. | |
| 7,250,496 B2 | 7/2007 | Bentwich | |
| 2001/0053519 A1 | 12/2001 | Fodor et al. | |
| 2002/0119138 A1 | 8/2002 | Cases et al. | |
| 2002/0127627 A1 | 9/2002 | Ramharack et al. | |
| 2002/0193315 A1 | 12/2002 | Omura et al. | |
| 2003/0028923 A1 | 2/2003 | Lardizabal et al. | 800/281 |
| 2003/0073103 A1 | 4/2003 | Ludwig et al. | |
| 2003/0100480 A1 | 5/2003 | Smith et al. | 514/1 |
| 2003/0104414 A1 | 6/2003 | Attersand | 435/6 |
| 2003/0115632 A1 | 6/2003 | Lardizabal et al. | |
| 2003/0124126 A1 | 7/2003 | Cases et al. | 424/146.1 |
| 2003/0152574 A1 | 8/2003 | Logan et al. | |
| 2003/0161831 A1 | 8/2003 | Cases et al. | |
| 2003/0170691 A1 | 9/2003 | Gimeno et al. | |
| 2003/0200563 A1 | 10/2003 | Butler et al. | |
| 2003/0202968 A1 | 10/2003 | Cases et al. | |
| 2003/0228597 A1 | 12/2003 | Cowsert et al. | |
| 2004/0054177 A1 | 3/2004 | Otake et al. | |
| 2004/0058820 A1 | 3/2004 | Hagmann et al. | |
| 2004/0097459 A1 | 5/2004 | Dobie et al. | |
| 2004/0122033 A1 | 6/2004 | Nargund et al. | |

| | | | |
|---|---|---|---|
| 2004/0259247 A1 | 12/2004 | Tuschl et al. | |

FOREIGN PATENT DOCUMENTS

| | | |
|---|---|---|
| EP | 1 308 459 A3 | 5/2003 |
| WO | WO 00/78961 | 12/2000 |
| WO | WO 01/68848 | 9/2001 |
| WO | WO 01/77389 | 10/2001 |
| WO | WO 01/92512 | 12/2001 |
| WO | WO 02/08260 | 1/2002 |
| WO | WO/02/068595 | 9/2002 |
| WO | WO/03/053363 | 7/2003 |

OTHER PUBLICATIONS

Melo et al. Trends in Molecular Medicine, 2005; vol. 11, No. 5, pp. 240-250.*
Vaughan et al. Current Opinons in Cardiology, 2001; vol. 16, pp. 195-200.*
Buhman et al., DGAT1 is not essential for intestinal triacylglycerol absorption or chylomicron synthesis, *J. Biol. Chem.*, 2002, 277:25474-25479.
Cases et al., Identification of a gene encoding an acyl CoA:diacylglycerol acyltransferase, a key enzyme in triacylglycerol synthesis, *Proc. Natl. Acad. Sci. U. S. A.*, 1998, 95:13018-13023.
Cases et al., Cloning of DGAT2, a second mammalian diacylglycerol acyltransferase, and related family members, *J. Biol. Chem.*, 2001, 276:38870-38876.
Chen et al., Increased insulin and leptin sensitivity in mice lacking acyl CoA:diacylglycerol acyltransferase 1, *J. Clin. Invest.*, 2002, 109:1049-1055.
Chen et al., Leptin modulates the effects of acyl CoA:diacylglycerol acyltransferase deficiency on murine fur and sebaceous glands, *J. Clin. Invest.*, 2002, 109:175-181.
Farese et al., Triglyceride synthesis: insights from the cloning of diacylglycerol acyltransferase, *Curr. Opin. Lipidol.*, 2000, 11:229-234.
Lardizabal et al., DGAT2 is a new diacylglycerol acyltransferase gene family: purification, cloning, and expression in insect cells of two polypeptides from *Mortierella ramanniana* with diacylglycerol acyltransferase activity, *J. Biol. Chem.*, 2001, 276:38862-38869.
Meegalla et al., Concerted elevation of acyl-coenzyme A:diacylglycerol acyltransferase (DGAT) activity through independent stimulation of mRNA expression of DGAT1 and DGAT2 by carbohydrate and insulin, *Biochem. Biophys. Res. Commun.*, 2002, 298:317-323.
Oelkers et al., Characterization of two human genes encoding acyl coenzyme A:cholesterol acyltransferase-related enzymes, *J. Biol. Chem.*, 1998, 273:26765-26771.
Smith et al., Obesity resistance and multiple mechanisms of triglyceride synthesis in mice lacking Dgat, *Nat. Genet.*, 2000, 25:87-90.

(Continued)

*Primary Examiner*—J. E Angell
(74) *Attorney, Agent, or Firm*—McDermott Will & Emery LLP

(57) ABSTRACT

Compounds, compositions and methods are provided for modulating the expression of diacylglycerol acyltransferase 2. The compositions comprise oligonucleotides, targeted to nucleic acid encoding diacylglycerol acyltransferase 2. Methods of using these compounds for modulation of diacylglycerol acyltransferase 2 expression and for diagnosis and treatment of disease associated with expression of diacylglycerol acyltransferase 2 are provided.

40 Claims, No Drawings

OTHER PUBLICATIONS

Waterman et al., Distinct ontogenic patterns of overt and latent DGAT activities of rat liver microsomes, *J. Lipid. Res.*, 2002, 43:1555-1562.

Cheng et al., "Human acyl-CoA: diacylglycerol acyltransferase is a tetrameric protein", *Biochem. J.* Nov. 1, 2001 359(pt 3):707-714.

Ludwig et al., "DGAT1 promoter polymorphism associated with alterations in body mass index, high density lipoprotein levels and blood pressure in Turkish women", *Clin. Genet.* Jul. 2002 62(1):68-73.

Tabata et al., "Xanthohumols, diacylglycerol acyltransferase inhibitors, from *Humulus lupulus*", *Phytochemistry* Oct. 1997 46(4):683-687.

Tomoda et al., "Roselipins, inhibitors of diacylglycerol acyltransferase, produced by *Gliocladium roseum* KF-1040", *J. Antibiot.* (Tokyo) Aug. 1999 52(8):689-694.

Yu et al., "Posttranscriptional control of the expression and function of diacylglycerol acyltransferase-1 in mouse adipocytes", *J. Biol. Chem.* Dec. 27, 2002 277(52):50876-50884.

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

The European Supplementary European Search Report dated Jul. 4, 2008 (EP 04 77 9444).

Branch et al., "A good antisense molecule is hard to find" TIBS (1998) 23:45-50.

Crooke et al., "Basic Principles of Antisense Therapeutics" Antisense Research and Application (1998) Chapter 1:1-50.

Desai et al., "Phenotypic Correction of Diabetic Mice by Adenovirus-Mediated Glucokinase Expression" Diabetes (2001) 50:2287-2295.

Guo et al., "par-1, a Gene Required for Establishing Polarity in *C. elegans* Embryos, Encodes a Putative Ser/Thr Kinase that is Asymmetrically Distributed" Cell (1995) 81:611-620.

Montgomery et al., "RNA as a target of double-stranded RNA-mediated genetic interference in *Caenorhabditis elegans*" Proc. Natl Acad. Sci. (1998) 95:15502-15507.

New England Biolabs 1998/1999 Catalog, cover page, pp. 121 and 284.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Stone et al., "Lipopenia and Skin Bather Abnormalities in DGAT2-deficient Mice" J. Biol. Chem. (2004) 279(12):11767-11776.

Tijsterman et al., "RNA Helicase MUT-14-Dependent Gene Silencing Triggered in *C. elegans* by Short Antisense RNAs" Science (2002) 295:694-697.

Yu et al., "Antisense Oligonucleotide Inhibition of DGAT2 Expression Reduced Hepatic Steatosis and Hyperlipidemia in Diet-Induced Obese Mice" Obesity Res. (2003) NAASO's 2003 Annual Meeting, Oct. 11-15, 11:A48.

Yu et al., "Antisense Oligonucleotide Reduction of DGAT2 Expression Improves Hepatic Steatosis and Hyperlipidemia in Obese Mice" Hepatology (2005) 42:362-371.

International Search Report for Int. Application No. PCT/US04/24384 dated Mar. 23, 2006.

Office Action for U.S. Appl. No. 11/066,725 dated Mar. 8, 2007.
Office Action for U.S. Appl. No. 11/066,725 dated Aug. 18, 2008.
Office Action for U.S. Appl. No. 11/066,725 dated Feb. 4, 2009.
Final Rejection for U.S. Appl. No. 11/066,725 dated Sep. 25, 2007.

* cited by examiner

MODULATION OF DIACYLGLYCEROL ACYLTRANSFERASE 2 EXPRESSION

FIELD OF THE INVENTION

The present invention provides compositions and methods for modulating the expression of diacylglycerol acyltransferase 2. In particular, this invention relates to compounds, particularly oligonucleotide compounds, which, in preferred embodiments, hybridize with nucleic acid molecules encoding diacylglycerol acyltransferase 2. Such compounds are shown herein to modulate the expression of diacylglycerol acyltransferase 2.

BACKGROUND OF THE INVENTION

Triglycerides are one of the major energy storage molecules in eukaryotes. The absorption of triglycerides (also called triacylglycerols) from food is a very efficient process which occurs by a series of steps wherein the dietary triacylglycerols are hydrolyzed in the intestinal lumen and then resynthesized within enterocytes. The resynthesis of triacylglycerols can occur via the monoacylglycerol pathway which commences with monoacylglycerol acyltransferase (MGAT) catalyzing the synthesis of diacylglycerol from monoacylglycerol and fatty acyl-CoA. An alternative synthesis of diacylglycerols is provided by the glycerol-phosphate pathway which describes the coupling of two molecules of fatty acyl-CoA to glycerol-3-phosphate. In either case, diacylglycerol is then acylated with another molecule of fatty acyl-CoA in a reaction catalyzed by one of two diacylglycerol acyltransferase enzymes to form the triglyceride (Farese et al., Curr. Opin. Lipidol., 2000, 11, 229-234).

The reaction catalyzed by diacylglycerol acyltransferase is the final and only committed step in triglyceride synthesis. As such, diacylglycerol acyltransferase is involved in intestinal fat absorption, lipoprotein assembly, regulating plasma triglyceride concentrations, and fat storage in adipocytes. The first diacylglycerol acyltransferase, diacylglycerol transferase 1, was identified in 1960 and the human and mouse genes encoding this protein were isolated in 1998 (Cases et al., Proc. Natl. Acad. Sci. U.S.A., 1998, 95, 13018-13023; Oelkers et al., J. Biol. Chem., 1998, 273, 26765-26771). Mice lacking diacylglycerol acyltransferase 1 are viable and can still synthesize triglycerides through other biological routes, suggesting the existence of multiple mechanisms for triglyceride synthesis (Smith et al., Nat. Genet., 2000, 25, 87-90).

A second diacylglycerol transferase, diacylglycerol transferase 2 (also known as DGAT2, diacylglycerol O-transferase 2, acyl-CoA:diacylglycerol acyltransferase 2), was subsequently identified in the fungus Mortierella, humans and mice (Cases et al., J. Biol. Chem., 2001, 276, 38870-38876; Lardizabal et al., J. Biol. Chem., 2001, 276, 38862-38869). Enzymatic assays indicate that this recently identified protein does possess diacylglycerol transferase activity that utilizes a broad range of long chain fatty acyl-CoA substrates (Cases et al., J. Biol. Chem., 2001, 276, 38870-38876).

Diacylglycerol transferase 2 is a member of a family of genes whose sequences are unrelated to diacylglycerol transferase 1. In addition to differing in sequence compared to diacylglycerol transferase 1, in vitro assays illustrate that diacylglycerol transferase 2 has higher activity at lower concentrations of magnesium chloride and oleoyl-CoA (Cases et al., J. Biol. Chem., 2001, 276, 38870-38876). The predicted protein sequence of diacylglycerol transferase 2 contains at least one putative transmembrane domain, three potential N-linked glycosylation sites, six potential protein kinase C phosphorylation consensus sites, as well as sequences in common with a putative glycerol phosphorylation site found in acyltransferase enzymes (Cases et al., J. Biol. Chem., 2001, 276, 38870-38876). The International Radiation Hybrid Mapping Consortium has mapped human diacylglycerol transferase 2 to chromosome 11q13.3.

In human tissues, the highest levels of diacylglycerol transferase 2 are detected in liver and white adipose tissues, with lower levels found in mammary gland, testis and peripheral blood leukocytes (Cases et al., J. Biol. Chem., 2001, 276, 38870-38876). Two mRNA species of 2.4 and 1.8 kilobases are detected in human tissues, whereas the major diacylglycerol transferase 2 mRNA species in mouse tissues is 2.4 kilobases. In addition to liver and white adipose tissues, diacylglycerol transferase 2 is expressed in all segments of the small intestine in mice, with higher expression in the proximal intestine and lower expression in the distal intestine (Cases et al., J. Biol. Chem., 2001, 276, 38870-38876).

Diacylglycerol transferase activity exhibits distinct patterns during postnatal development of the rat liver. As there is no correlation between the mRNA expression and activity patterns, post-translational modifications may participate in the regulation of diacylglycerol transferase 2 activity during rat development (Waterman et al., J. Lipid. Res., 2002, 43, 1555-1562).

Diacylglycerol transferase 2 mRNA is preferentially upregulated by insulin treatment, as shown by in vitro assays measuring the diacylglycerol activity from the membrane fraction of cultured mouse adipocytes (Meegalla et al., Biochem. Biophys. Res. Commun., 2002, 298, 317-323). In fasting mice, diacylglycerol transferase 2 expression is greatly reduced, and dramatically increases upon refeeding. The expression patterns of two enzymes that participate in fatty acid synthesis, acetyl-CoA carboxylase and fatty acid synthase, respond to fasting and refeeding in a similar fashion. These results, combined with the observation that diacylglycerol transferase 2 is abundantly expressed in liver, suggest that diacylglycerol transferase 2 is tightly linked to the endogenous fatty acid synthesis pathway (Meegalla et al., Biochem. Biophys. Res. Commun., 2002, 298, 317-323).

Studies of mice harboring a disruption in the diacylglycerol acyltransferase 1 gene provide evidence that diacylglycerol acyltransferase 2 contributes to triglyceride synthesis. Levels of diacylglycerol transferase 2 mRNA expression are similar in intestinal segments from both wild type and diacylglycerol transferase 1-deficient mice (Buhman et al., J. Biol. Chem., 2002, 277, 25474-25479). Using magnesium chloride to distinguish between diacylglycerol transferase 1 and 2 activity, Buhman, et al. observed that, in diacylglycerol transferase 1-deficient mice, diacylglycerol transferase activity is reduced to 50% in the proximal intestine and to 10-15% in the distal intestine (Buhman et al., J. Biol. Chem., 2002, 277, 25474-25479).

Additionally, diacylglycerol transferase 2 mRNA levels are not up-regulated the liver or adipose tissues of diacylglycerol transferase 1-deficient mice, even after weeks of high-fat diet (Cases et al., J. Biol. Chem., 2001, 276, 38870-38876; Chen et al., J. Clin. Invest., 2002, 109, 1049-1055). However, in ob/ob mice, which have a mutation in the leptin gene that results in obesity, diacylglycerol transferase 2 is more highly expressed than in wild type mice, suggesting that diacylglycerol transferase 2 may be partly responsible for the highly accumulated fat mass seen in these mice. Furthermore, the combined mutations of leptin and diacylglycerol transferase 1 leads to a three-fold elevation in diacylglycerol transferase 2 expression in white adipose tissue, compared to the levels in the same tissue from diacylglycerol transferase 1-deficient mice (Chen et al., *J. Clin. Invest.*, 2002, 109, 1049-1055). Diacylglycerol transferase 2 mRNA is also upregulated in the skin of these mice (Chen et al., *J. Clin. Invest.*, 2002, 109, 175-181). These data suggest leptin normally downregulates diacylglycerol transferase 2 expression, and that the upregulation of diacylglycerol transferase 2 in white adipose tissue in these mice may provide an alternate pathway for the triglyceride synthesis that still occurs in leptin deficient/diacylglycerol transferase 1-deficient mice (Chen et al., *J. Clin. Invest.*, 2002, 109, 1049-1055).

Diacylglycerol acyltransferase 1 knockout mice exhibit interesting phenotypes in that they are lean, resistant to diet-induce obesity, have decreased levels of tissue triglycerides and increased sensitivity to insulin and leptin (Chen et al., *J. Clin. Invest.*, 2002, 109, 1049-1055; Smith et al., *Nat. Genet.*, 2000, 25, 87-90). As diacylglycerol transferase 2 also participates in triglyceride synthesis, interfering with diacylglycerol transferase 2 may similarly lead to reduced body fat content.

The US pre-grant publications 20030124126 and 20020119138 claim and disclose a nucleic acid molecule encoding human diacylglycerol transferase 2 alpha, as well as compositions, including antisense oligonucleotides, for modulating the activity of said diacylglycerol transferase 2 alpha (Cases et al., 2003).

The US pre-grant publication 20030104414 discloses and claims nucleic acid sequences which are members of a group of genes referred to as "protein cluster V" as well as the method for identification of an agent capable of modulating nucleic acid molecules in the protein cluster V group. This application also discloses the use of RNA interference or double-stranded RNA to disrupt the function of protein cluster V gene family members (Attersand, 2003).

The US pre-grant publication 20030100480 discloses that diacylcglycerol transferase activity, including that of diacylglycerol transferase 2, may be modified by a variety of methods, including antisense, RNA interference and diacylglycerol transferase 2 antisense plasmid constructs (Smith et al., 2003).

The US pre-grant publication 20030028923 claims and discloses a method for modifying the triacylglyerol composition in a plant cell, comprising transforming a plant cell with a nucleic acid construct encoding an enzyme active in the formation of triacylglycerol from diacylglycerol and fatty acyl substrates, including nucleic acid constructs in the antisense orientation. Also disclosed and claimed is a method for ameliorating a disease or condition associated with altered diacylglycerol acyltransferase activity by administering to a subject a therapeutically effective amount of a diacylglycerol acyltransferase agonist. This application discloses that such antagonists can include antisense molecules (Lardizabal et al., 2003).

The PCT publication WO 00/78961 claims and discloses isolated nucleic acid molecules selected from a group including a nucleic acid sequence encoding diacylglycerol acyltransferase 2. This publication also discloses that sense or antisense oligonucleotides binding to target nucleic acid sequences can interfere with transcription or translation of the disclosed and claimed nucleic acid molecules (Baker et al., 2000).

Disclosed and claimed in the PCT publication WO 01/77389 are polynucleotides selected from a group of sequences including a nucleotide sequence encoding a human diacylglycerol acyltransferase. Also claimed and disclosed are a method for screening for the altered expression of said polynucleotides and a method for screening a library of molecules that specifically bind to said polynucleotide sequences (Shiffman et al., 2001).

The PCT publication WO 01/68848 discloses and claims a nucleic acid molecules encoding secreted and transmembrane polypeptides, including a human diacylglycerol acyltransferase 2 nucleic acid molecule, and oligonucleotide probes derived from any of these sequences (Baker et al., 2001).

Disclosed and claimed in the European patent application EP 1 308 459 are a group of polynucleotide sequences, including a nucleic acid molecule encoding human diacylglycerol acyltransferase 2, and antisense polynucleotides against this group of polynucleotide sequences (Isogai et al., 2003).

The PCT publication WO 02/08260 discloses and claims an isolated, purified polynucleotide sequence with identity to a human diacylglycerol transferase 2 nucleotide sequence. This application also discloses a substantially purified oligonucleotide that includes a region of nucleotide sequence that hybridizes to at least 8 consecutive nucleotides of sense or antisense sequence of a nucleotide sequence selected from a group consisting of sequences with identity to human diacylglycerol acyltransferase 2 (Botstein et al., 2002).

Currently, there are no known therapeutic agents which effectively inhibit the synthesis of diacylglycerol acyltransferase 2. Consequently, there remains a long felt need for additional agents capable of effectively inhibiting diacylglycerol acyltransferase 1 function.

Antisense technology is an effective means for reducing the expression of specific gene products and may therefore prove to be uniquely useful in a number of therapeutic, diagnostic, and research applications for the modulation of diacylglycerol acyltransferase 2 expression.

The present invention provides compositions and methods for modulating diacylglycerol acyltransferase 2 expression.

SUMMARY OF THE INVENTION

The present invention is directed to compounds, especially nucleic acid and nucleic acid-like oligomers, which are targeted to a nucleic acid encoding diacylglycerol acyltransferase 2, and which modulate the expression of diacylglycerol acyltransferase 2. Pharmaceutical and other compositions comprising the compounds of the invention are also provided. Further provided are methods of screening for modulators of diacylglycerol acyltransferase 2 and methods of modulating the expression of diacylglycerol acyltransferase 2 in cells, tissues or animals comprising contacting said cells, tissues or animals with one or more of the compounds or compositions of the invention. Methods of treating an animal, particularly a human, suspected of having or being prone to a disease or condition associated with expression of diacylglycerol acyltransferase 2 are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs compounds, preferably oligonucleotides and similar species for use in modulating the function or effect of nucleic acid molecules encoding diacylglycerol acyltransferase 2. This is accomplished by providing oligonucleotides which specifically hybridize with one or more nucleic acid molecules encoding diacylglycerol acyltransferase 2. As used herein, the terms "target nucleic acid" and "nucleic acid molecule encoding diacylglycerol acyltransferase 2" have been used for convenience to encompass DNA encoding diacylglycerol acyltransferase 2, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of diacylglycerol acyltransferase 2. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise-pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, or about 99%.

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. These oligonucleotides are then tested using the methods described herein to determine their ability to inhibit expression of diacylglycerol acyltransferase 2 mRNA.

In the context of this invention, the term "oligomeric compound" refers to a polymer or oligomer comprising a plurality of monomeric units. In the context of this invention, the term oligonucleotide refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes diacylglycerol acyltransferase 2.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding diacylglycerol acyltransferase 2, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5'cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric compounds are also targeted to or not targeted to regions of the target nucleobase sequence (e.g., such as those disclosed in Example 13) comprising nucleobases 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 2101-2150, 2151-2200, 2201-2250, 2251-2300, 2301-2350, 2351-2400, 2401-2439, or any combination thereof.

D. Screening and Target Validation

In a further embodiment, the "preferred target segments" identified herein may be employed in a screen for additional compounds that modulate the expression of diacylglycerol acyltransferase 2. "Modulators" are those compounds that decrease or increase the expression of a nucleic acid molecule encoding diacylglycerol acyltransferase 2 and which comprise at least an 8-nucleobase portion which is complementary to a preferred target segment. The screening method comprises the steps of contacting a preferred target segment of a nucleic acid molecule encoding diacylglycerol acyltransferase 2 with one or more candidate modulators, and selecting for one or more candidate modulators which decrease or increase the expression of a nucleic acid molecule encoding diacylglycerol acyltransferase 2. Once it is shown that the candidate modulator or modulators are capable of modulating (e.g. either decreasing or increasing) the expression of a nucleic acid molecule encoding diacylglycerol acyltransferase 2, the modulator may then be employed in further investigative studies of the function of diacylglycerol acyltransferase 2, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between diacylglycerol acyltransferase 2 and a disease state, phenotype, or condition. These methods include detecting or modulating diacylglycerol acyltransferase 2 comprising contacting a sample, tissue, cell, or organism with the compounds of the present invention, measuring the nucleic acid or protein level of diacylglycerol acyltransferase 2 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SURF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The compounds of the invention are useful for research and diagnostics, because these compounds hybridize to nucleic acids encoding diacylglycerol acyltransferase 2. For example, oligonucleotides that are shown to hybridize with such efficiency and under such conditions as disclosed herein as to be effective diacylglycerol acyltransferase 2 inhibitors will also be effective primers or probes under conditions favoring gene amplification or detection, respectively. These primers and probes are useful in methods requiring the specific detection of nucleic acid molecules encoding diacylglycerol acyltransferase 2 and in the amplification of said nucleic acid molecules for detection or for use in further studies of diacylglycerol acyltransferase 2. Hybridization of the antisense oligonucleotides, particularly the primers and probes, of the invention with a nucleic acid encoding diacylglycerol acyltransferase 2 can be detected by means known in the art. Such means may include conjugation of an enzyme to the oligonucleotide, radiolabelling of the oligonucleotide or any other suitable detection means. Kits using such detection means for detecting the level of diacylglycerol acyltransferase 2 in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of diacylglycerol acyltransferase 2 is treated by administering antisense compounds in accordance with this invention. For example, in one non-limiting embodiment, the methods comprise the step of administering to the animal in need of treatment, a therapeutically effective amount of a diacylglycerol acyltransferase 2 inhibitor. The diacylglycerol acyltransferase 2 inhibitors of the present invention effectively inhibit the activity of the diacylglycerol acyltransferase 2 protein or inhibit the expression of the diacylglycerol acyltransferase 2 protein. In one embodiment, the activity or expression of diacylglycerol acyltransferase 2 in an animal is inhibited by about 10%. Preferably, the activity or expression of diacylglycerol acyltransferase 2 in an animal is inhibited by about 30%. More preferably, the activity or expression of diacylglycerol acyltransferase 2 in an animal is inhibited by 50% or more. Thus, the oligomeric compounds modulate expression of diacylglycerol acyltransferase 2 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of diacylglycerol acyltransferase 2 may be measured in serum, adipose tissue, liver or any other body fluid, tissue or organ of the animal. Preferably, the cells contained within said fluids, tissues or organs being analyzed contain a nucleic acid molecule encoding diacylglycerol acyltransferase 2 protein and/or the diacylglycerol acyltransferase 2 protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphoro-dithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2'to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3'position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—CH$_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C?C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia OfPolymer ScienceAnd Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 ?C and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667;

5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 ?m in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. applications Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2l-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylamino-oxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55?C (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand,.* 1990, 44, 639-641; Reddy, M. P., et al., *Tetrahedron Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH₄OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-methoxyethyl)]-[2'-deoxy]-[2'-O-(Methoxyethyl)]Chimeric Phosphorothioate Oligonucleotides

[2'-O-(2-methoxyethyl)]-[2'-deoxy]-[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl)Phosphodiester]Chimeric Oligonucleotides

[2'-O-(2-methoxyethyl phosphodiester]-[2'-deoxy phosphorothioate]-[2'-O-(methoxyethyl)phosphodiester]chimeric oligonucleotides are prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Diacylglycerol Acyltransferase 2

In accordance with the present invention, a series of nucleic acid duplexes comprising the antisense compounds of the present invention and their complements can be designed to target diacylglycerol acyltransferase 2. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 231) and having a two-nucleobase overhang of deoxythymidine(dT) would have the following structure:

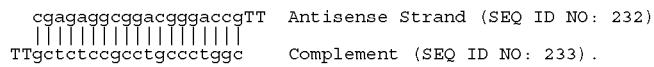

```
cgagaggcggacgggaccgTT  Antisense Strand (SEQ ID NO: 232)
|||||||||||||||||||
TTgctctccgcctgccctggc  Complement (SEQ ID NO: 233).
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate diacylglycerol acyltransferase 2 expression.

When cells reached 80% confluency, they are treated with duplexed antisense compounds of the invention. For cells grown in 96-well plates, wells are washed once with 200 µL OPTI-MEM-1 reduced-serum medium (Gibco BRL) and then treated with 130 µL of OPTI-MEM-1 containing 12 µg/mL LIPOFECTIN (Gibco BRL) and the desired duplex antisense compound at a final concentration of 200 mM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55?C for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE? MDQ) or, for individually prepared samples, on a commercial CE apparatus (e.g., Beckman P/ACE? 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

3T3-L1 Cells:

The mouse embryonic adipocyte-like cell line 3T3-L1 was obtained from the American Type Culture Collection (Manassas, Va.). 3T3-L1 cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 80% confluence. Cells were seeded into 96-well plates (Falcon-Primaria #3872) at a density of 4000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 65-75% confluency, they were treated with oligonucleotide. For cells grown in 96-well plates, wells were washed once with 100 ?L OPTI-MEM? -1 reduced-serum medium (Invitrogen Corporation, Carlsbad, Calif.) and then treated with 130 ?L of OPTI-MEM? -1 containing 3.75 ?g/mL LIPOFECTIN? (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Diacylglycerol Acyltransferase 2 Expression Antisense modulation of diacylglycerol acyltransferase 2 expression can be assayed in a variety of ways known in the art. For example, diacylglycerol acyltransferase 2 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM? 7600, 7700, or 7900 Sequence Detection System, available from PE-Applied Biosystems, Foster City, Calif. and used according to manufacturer's instructions.

Protein levels of diacylglycerol acyltransferase 2 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to diacylglycerol acyltransferase 2 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In Vivo Studies for the Use of Diacylglycerol Acyltransferase 2 Inhibitors Phenotypic Assays Once diacylglycerol acyltransferase 2 inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of diacylglycerol acyltransferase 2 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with diacylglycerol acyltransferase 2 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the diacylglycerol acyltransferase 2 inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or diacylglycerol acyltransferase 2 inhibitor. Furthermore, to prevent the doctors from being biased in treatments, they are not informed as to whether the medication they are administering is a diacylglycerol acyltransferase 2 inhibitor or a placebo. Using this randomization approach, each volunteer has the same chance of being given either the new treatment or the placebo.

Volunteers receive either the diacylglycerol acyltransferase 2 inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding diacylglycerol acyltransferase 2 or diacylglycerol acyltransferase 2 protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and diacylglycerol acyltransferase 2 inhibitor treatment. In general, the volunteers treated with placebo have little or no response to treatment, whereas the volunteers treated with the diacylglycerol acyltransferase 2 inhibitor show positive trends in their disease state or condition index at the conclusion of the study.

Example 12

RNA Isolation

Poly(A)+ mRNA Isolation

Poly(A)+ mRNA was isolated according to Miura et al., (Clin. Chem., 1996, 42, 1758-1764). Other methods for poly (A)+ mRNA isolation are routine in the art. Briefly, for cells grown on 96-well plates, growth medium was removed from the cells and each well was washed with 200 ?L cold PBS. 60 ?L lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 ?L of lysate was transferred to Oligo d(T) coated 96-well plates (AGCT Inc., Irvine Calif.). Plates were incubated for 60 minutes at room temperature, washed 3 times with 200 ?L of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 ?L of elution buffer (5 mM Tris-HCl pH 7.6), preheated to 70?C, was added to each well, the plate was incubated on a 90?C hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96? kit and buffers purchased from Qiagen Inc. (Valencia, Calif.) following the manufacturer's recommended procedures. Briefly, for cells grown on 96-well plates, growth medium was removed from the cells and each well was washed with 200 ?L cold PBS. 150 ?L Buffer RLT was added to each well and the plate vigorously agitated for 20 seconds. 150 ?L of 70% ethanol was then added to each well and the contents mixed by pipetting three times up and down. The samples were then transferred to the RNEASY 96? well plate attached to a QIAVAC? manifold fitted with a waste collection tray and attached to a vacuum source. Vacuum was applied for 1 minute. 500 ?L of Buffer RW1 was added to each well of the RNEASY 96? plate and incubated for 15 minutes and the vacuum was again applied for 1 minute. An additional 500 ?L of Buffer RW1 was added to each well of the RNEASY 96? plate and the vacuum was applied for 2 minutes. 1 mL of Buffer RPE was then added to each well of the RNEASY 96? plate and the vacuum applied for a period of 90 seconds. The Buffer RPE wash was then repeated and the vacuum was applied for an additional 3 minutes. The plate was then removed from the QIAVAC? manifold and blotted dry on paper towels. The plate was then re-attached to the QIAVAC? manifold fitted with a collection tube rack containing 1.2 mL collection tubes. RNA was then eluted by pipetting 140 ?L of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Diacylglycerol Acyltransferase 2 mRNA Levels Quantitation of diacylglycerol acyltransferase 2 mRNA levels was accomplished by real-time quantitative PCR using the ABI PRISM? 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM? Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 ?L PCR cocktail (2.5×PCR buffer minus $MgCl_2$, 6.6 mM $MgCl_2$, 375 ?M each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 ?L total RNA solution (20-200 ng). The RT reaction was carried out by incubation for 30 minutes at 48?C. Following a 10 minute incubation at 95?C to activate the PLATINUM® Taq, 40 cycles of a two-step PCR protocol were carried out: 95?C for 15 seconds (denaturation) followed by 60?C for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 ?L of RiboGreen™ working reagent (RiboGreen™ reagent diluted 1:350 in 10 mM Tris-HCl, 1 mM EDTA, pH 7.5) is pipetted into a 96-well plate containing 30 ?L purified, cellular RNA. The plate is read in a CytoFluor 4000 (PE Applied Biosystems) with excitation at 485 nm and emission at 530 nm.

Probes and primers to human diacylglycerol acyltransferase 2 were designed to hybridize to a human diacylglycerol acyltransferase 2 sequence, using published sequence information (GenBank accession number NM_032564.2, incorporated herein as SEQ ID NO: 4). For human diacylglycerol acyltransferase 2 the PCR primers were: forward primer: CATACGGCCTTACCTGGCTACA (SEQ ID NO: 5) reverse primer: CAGACATCAGGTACTCCCTCAACA (SEQ ID NO: 6) and the PCR probe was: FAM-TGGCAGGCAACT-TCCGAATGCC-TAMRA (SEQ ID NO: 7) where FAM is the fluorescent dye and TAMRA is the quencher dye. For human GAPDH the PCR primers were: forward primer: GAAGGT-GAAGGTCGGAGTC(SEQ ID NO:8) reverse primer: GAA-GATGGTGATGGGATTTC (SEQ ID NO:9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Probes and primers to mouse diacylglycerol acyltransferase 2 were designed to hybridize to a mouse diacylglycerol acyltransferase 2 sequence, using published sequence information (GenBank accession number AK002443.1, incorporated herein as SEQ ID NO:11). For mouse diacylglycerol acyltransferase 2 the PCR primers were:

forward primer: ACTCTGGAGGTTGGCACCAT (SEQ ID NO:12)

reverse primer: GGGTGTGGCTCAGGAGGAT (SEQ ID NO: 13) and the PCR probe was: FAM-CAGCGT-TGCTCTGGCGCA-TAMRA (SEQ ID NO: 14) where FAM is the fluorescent reporter dye and TAMRA is the quencher dye. For mouse GAPDH the PCR primers were:

forward primer: GGCAAATTCAACGGCACAGT(SEQ ID NO:15)

reverse primer: GGGTCTCGCTCCTGGAAGAT(SEQ ID NO:16) and the PCR probe was: 5' JOE-AAGGC-CGAGAATGGGAAGCTTGTCATC-TAMRA 3'(SEQ ID NO: 17) where JOE is the fluorescent reporter dye and TAMRA is the quencher dye.

Example 14

Northern Blot Analysis of Diacylglycerol Acyltransferase 2 mRNA Levels

Eighteen hours after antisense treatment, cell monolayers were washed twice with cold PBS and lysed in 1 mL RNA-ZOL? (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND? –N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER? UV Crosslinker 2400 (Stratagene, Inc, La Jolla, Calif.) and then probed using QUICKHYB? hybridization solution (Stratagene, La Jolla, Calif.) using manufacturer's recommendations for stringent conditions.

To detect human diacylglycerol acyltransferase 2, a human diacylglycerol acyltransferase 2 specific probe was prepared by PCR using the forward primer CATACGGCCTTACCTG-GCTACA (SEQ ID NO: 5) and the reverse primer CAGA-CATCAGGTACTCCCTCAACA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse diacylglycerol acyltransferase 2, a mouse diacylglycerol acyltransferase 2 specific probe was prepared by PCR using the forward primer ACTCTGGAGGTTGGCACCAT (SEQ ID NO: 12) and the reverse primer GGGTGTGGCTCAGGAGGAT (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER? and IMAGEQUANT? Software V3.3 (Molecular Dynamics, Sunnyvale, Calif.). Data was normalized to GAPDH levels in untreated controls.

Example 15

Antisense Inhibition of Human Diacylglycerol Acyltransferase 2 Expression by Chimeric Phosphorothioate Oligonucleotides Having 2'-MOE Wings and a Deoxy Gap In accordance with the present invention, a series of antisense compounds was designed to target different regions of the human diacylglycerol acyltransferase 2 RNA, using published sequences (GenBank accession number NM_032564.2, incorporated herein as SEQ ID NO: 4, nucleotides 5669186 to 5712008 of the nucleotide sequence with the GenBank accession number NT_033927.5, incorporated herein as SEQ ID NO: 18). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human diacylglycerol acyltransferase 2 mRNA levels by quantitative real-time PCR as described in other examples herein. Data are averages from three experiments in which A549 cells were treated with the antisense oligonucleotides of the present invention. The positive control for each datapoint is identified in the table by sequence ID number. If present, "N.D." indicates "no data".

TABLE 1

Inhibition of human diacylglycerol acyltransferase 2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 217310 | Coding | 4 | 579 | ctcctgccacctttcttggg | 79 | 20 | 1 |
| 217312 | Coding | 4 | 639 | tggatgggaaagtagtctcg | 82 | 21 | 1 |
| 217313 | Coding | 4 | 644 | ccagctggatgggaaagtag | 34 | 22 | 1 |
| 217314 | Coding | 4 | 649 | cttcaccagctggatgggaa | 40 | 23 | 1 |
| 217315 | Coding | 4 | 654 | tgtgtcttcaccagctggat | 86 | 24 | 1 |
| 217316 | Coding | 4 | 659 | ggttgtgtgtcttcaccagc | 88 | 25 | 1 |
| 217317 | Coding | 4 | 664 | cagcaggttgtgtgtcttca | 93 | 26 | 1 |
| 217318 | Coding | 4 | 669 | gtggtcagcaggttgtgtgt | 74 | 27 | 1 |
| 217319 | Coding | 4 | 674 | tcctggtggtcagcaggttg | 84 | 28 | 1 |
| 217320 | Coding | 4 | 679 | atagttcctggtggtcagca | 90 | 29 | 1 |
| 217321 | Coding | 4 | 684 | aagatatagttcctggtggt | 77 | 30 | 1 |
| 217322 | Coding | 4 | 689 | atccaaagatatagttcctg | 73 | 31 | 1 |
| 217323 | Coding | 4 | 694 | gtggtatccaaagatatagt | 70 | 32 | 1 |
| 217324 | Coding | 4 | 723 | aaggcacccaggcccatgat | 74 | 33 | 1 |
| 217325 | Coding | 4 | 846 | cctccagacatcaggtactc | 73 | 34 | 1 |
| 217328 | Coding | 4 | 909 | gcattgccactcccattctt | 89 | 35 | 1 |
| 217329 | Coding | 4 | 914 | tgatagcattgccactccca | 88 | 36 | 1 |
| 217330 | Coding | 4 | 919 | gatgatgatagcattgccac | 77 | 37 | 1 |
| 217331 | Coding | 4 | 924 | accacgatgatgatagcatt | 77 | 38 | 1 |
| 217333 | Coding | 4 | 963 | ttgccaggcatggagctcag | 79 | 39 | 1 |

TABLE 1-continued

Inhibition of human diacylglycerol acyl-
transferase 2 mRNA levels by chimeric phosphorothioate
oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 217336 | Coding | 4 | 1110 | tggacccatcggccccagga | 72 | 40 | 1 |
| 217337 | Coding | 4 | 1115 | tcttctggacccatcggccc | 76 | 41 | 1 |
| 217338 | Coding | 4 | 1120 | gaacttcttctggacccatc | 43 | 42 | 1 |
| 217339 | Coding | 4 | 1125 | ttctggaacttcttctggac | 62 | 43 | 1 |
| 217341 | Coding | 4 | 1197 | ggcaccagcccccaggtgtc | 68 | 44 | 1 |
| 217342 | Coding | 4 | 1202 | agtagggcaccagcccccag | 54 | 45 | 1 |
| 217343 | Coding | 4 | 1207 | cttggagtagggcaccagcc | 69 | 46 | 1 |
| 217346 | Coding | 4 | 1309 | cagggcctccatgtacatgg | 81 | 47 | 1 |
| 217347 | Coding | 4 | 1314 | ttcaccagggcctccatgta | 54 | 48 | 1 |
| 217348 | Coding | 4 | 1319 | agagcttcaccagggcctcc | 83 | 49 | 1 |
| 217353 | 3'UTR | 4 | 1469 | aacccacagacacccatgac | 65 | 50 | 1 |
| 217354 | 3'UTR | 4 | 1474 | taaataacccacagacaccc | 40 | 51 | 1 |
| 217355 | 3'UTR | 4 | 1479 | tcttttaaataacccacaga | 47 | 52 | 1 |
| 334165 | intron | 18 | 21985 | acaaaagagcatcctcctca | 64 | 53 | 1 |
| 334166 | intron | 18 | 23110 | actataaatgcttcagtcca | 78 | 54 | 1 |
| 334167 | exon:intron | 18 | 31175 | ttgcacttacctttcttggg | 8 | 55 | 1 |
| 334168 | exon:intron | 18 | 31611 | agcactttacctggatggga | 63 | 56 | 1 |
| 334169 | intron | 18 | 33686 | tcagtgaaatgaggcagatg | 84 | 57 | 1 |
| 334170 | intron | 18 | 35303 | ctcaaaagaggtgacatcaa | 72 | 58 | 1 |
| 334171 | exon:intron | 18 | 37412 | ggattcttacctccagacat | 22 | 59 | 1 |
| 334172 | intron:exon | 18 | 39106 | caggtcagctctggaaggga | 47 | 60 | 1 |
| 334173 | intron | 18 | 37108 | ttcccctggacctccatggg | 76 | 61 | 1 |
| 334174 | 5'UTR | 4 | 46 | gtggcgcgagagaaacagcc | 82 | 62 | 1 |
| 334175 | 5'UTR | 4 | 134 | gccagggcttcgcgcagagc | 75 | 63 | 1 |
| 334176 | Start Codon | 4 | 222 | agggtcttcatggctgaagc | 53 | 64 | 1 |
| 334177 | Coding | 4 | 246 | aggaccccggagtaggcggc | 95 | 65 | 1 |
| 334178 | Coding | 4 | 441 | acccactggagcactgagat | 83 | 66 | 1 |
| 334179 | Coding | 4 | 855 | gggcagatacctccagacat | 28 | 67 | 1 |
| 334180 | Coding | 4 | 987 | cggttccgcagggtgactgc | 72 | 68 | 1 |
| 334181 | Stop Codon | 4 | 1387 | aaggctggctcagttcacct | 78 | 69 | 1 |
| 334182 | 3'UTR | 4 | 1401 | gggagttggccccgaaggct | 64 | 70 | 1 |
| 334183 | 3'UTR | 4 | 1414 | gctggttcctccagggagtt | 81 | 71 | 1 |
| 334184 | 3'UTR | 4 | 1449 | acttccaaatttacagagca | 72 | 72 | 1 |
| 334185 | 3'UTR | 4 | 1584 | ccacctagaacagggcaagc | 80 | 73 | 1 |
| 334186 | 3'UTR | 4 | 1635 | gggaagaagagaggttagct | 35 | 74 | 1 |
| 334187 | 3'UTR | 4 | 1647 | tcacttcaggaagggaagaa | 63 | 75 | 1 |

TABLE 1-continued

Inhibition of human diacylglycerol acyl-
transferase 2 mRNA levels by chimeric phosphorothioate
oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 334188 | 3'UTR | 4 | 1679 | ccttcttccccaagaagact | 51 | 76 | 1 |
| 334189 | 3'UTR | 4 | 1707 | ctaactggtccaagtcacta | 82 | 77 | 1 |
| 334190 | 3'UTR | 4 | 1724 | ggcaaaaagtgaatcatcta | 76 | 78 | 1 |
| 334191 | 3'UTR | 4 | 1743 | ttcgcctctcatccctaggg | 13 | 79 | 1 |
| 334192 | 3'UTR | 4 | 1763 | ggcttgtatgagaagtggct | 77 | 80 | 1 |
| 334193 | 3'UTR | 4 | 1802 | tttcaggactagacgagcgt | 82 | 81 | 1 |
| 334194 | 3'UTR | 4 | 1946 | ctccgatatgagtgactagg | 85 | 82 | 1 |
| 334195 | 3'UTR | 4 | 1969 | ctcatcctggaggccagtcc | 72 | 83 | 1 |
| 334196 | 3'UTR | 4 | 1974 | ccatcctcatcctggaggcc | 50 | 84 | 1 |
| 334197 | 3'UTR | 4 | 1989 | gtgtcattgccaccccatc | 49 | 85 | 1 |
| 334198 | 3'UTR | 4 | 2055 | acctagctcatggtggcggc | 67 | 86 | 1 |
| 334199 | 3'UTR | 4 | 2067 | accagttactccacctagct | 73 | 87 | 1 |
| 334200 | 3'UTR | 4 | 2088 | gtcatcagccacccaagaaa | 73 | 88 | 1 |
| 334201 | 3'UTR | 4 | 2125 | gtgctccaggccaaggctga | 75 | 89 | 1 |
| 334202 | 3'UTR | 4 | 2137 | accagtaagcatgtgctcca | 84 | 90 | 1 |
| 334203 | 3'UTR | 4 | 2143 | gaggccaccagtaagcatgt | 65 | 91 | 1 |
| 334204 | 3'UTR | 4 | 2150 | gtaaactgaggccaccagta | 82 | 92 | 1 |
| 334205 | 3'UTR | 4 | 2184 | cttcctcacatccagaatct | 22 | 93 | 1 |
| 334206 | 3'UTR | 4 | 2220 | tgctcagaaggccaggcccc | 89 | 94 | 1 |
| 334207 | 3'UTR | 4 | 2242 | acctgctttggaactaatct | 76 | 95 | 1 |
| 334208 | 3'UTR | 4 | 2269 | gaaaagtgaggcttgggttc | 44 | 96 | 1 |
| 334209 | 3'UTR | 4 | 2367 | aaaagtctgacatggtgcaa | 75 | 97 | 1 |

As shown in Table 1, SEQ ID NOs 20, 21, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 60, 61, 62, 63, 64, 65, 66, 68, 69, 70, 71, 72, 73, 75, 76, 77, 78, 80, 81, 82, 83, 84, 85, 86, 87, 88, 89, 90, 91, 92, 94, 95, 96 and 97 demonstrated at least 40% inhibition of human diacylglycerol acyltransferase 2 expression in this assay and are therefore preferred. More preferred are SEQ ID NOs 65, 26, 29 and 35. The target regions to which these preferred sequences are complementary are herein referred to as "preferred target segments" and are therefore preferred for targeting by compounds of the present invention. These preferred target segments are shown in Table 3. These sequences are shown to contain thymine (T) but one of skill in the art will appreciate that thymine (T) is generally replaced by uracil (U) in RNA sequences. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

Example 16

Antisense Inhibition of Mouse Diacylglycerol Acyltransferase 2 Expression by Chimeric Phosphorothioate Oligonucleotides Having 21-MOE Wings and a Deoxy Gap.

In accordance with the present invention, a second series of antisense compounds was designed to target different regions of the mouse diacylglycerol acyltransferase 2 RNA, using published sequences (GenBank accession number AK002443.1, incorporated herein as SEQ ID NO: 11). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse diacylglycerol acyltransferase 2 mRNA levels by quantitative real-time PCR as described in other examples herein. Data are averages from three experiments in which 3T3-L1 cells were treated with the antisense oligonucleotides of the present invention. The positive control for each datapoint is identified in the table by sequence ID number. If present, "N.D." indicates "no data".

TABLE 2

Inhibition of mouse diacylglycerol acyltransferase 2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 217299 | 5'UTR | 11 | 21 | ccaccctagatgagcagaaa | 0 | 98 | 1 |
| 217300 | 5'UTR | 11 | 36 | ggtaggtagccgctgccacc | 26 | 99 | 1 |
| 217301 | 5'UTR | 11 | 44 | agagctgaggtaggtagccg | 24 | 100 | 1 |
| 217302 | 5'UTR | 11 | 99 | gcgctgagctccgggagctg | 50 | 101 | 1 |
| 217303 | 5'UTR | 11 | 183 | aagccaatgcacgtcacggc | 18 | 102 | 1 |
| 217304 | Start Codon | 11 | 199 | gagggtcttcatgctgaagc | 19 | 103 | 1 |
| 217305 | Coding | 11 | 262 | gttttcgctgcgggcagctt | 10 | 104 | 1 |
| 217306 | Coding | 11 | 386 | gtttttccaccttagatctg | 0 | 105 | 1 |
| 217307 | Coding | 11 | 403 | tgagatgacctgcagctgtt | 0 | 106 | 1 |
| 217308 | Coding | 11 | 447 | caggccactcctagcaccag | 0 | 107 | 1 |
| 217309 | Coding | 11 | 457 | gatgacactgcaggccactc | 29 | 108 | 1 |
| 217311 | Coding | 11 | 586 | ccacacggcccagtttcgca | 64 | 109 | 1 |
| 217326 | Coding | 11 | 831 | gggcagatgcctccagacat | 15 | 110 | 1 |
| 217327 | Coding | 11 | 841 | tcggttgacagggcagatgc | 31 | 111 | 1 |
| 217332 | Coding | 11 | 920 | gggactcagctgcacctccc | 18 | 112 | 1 |
| 217334 | Coding | 11 | 1006 | cagatcagctccatggcgca | 30 | 113 | 1 |
| 217335 | Coding | 11 | 1051 | cacctgcttgtatacctcat | 41 | 114 | 1 |
| 217340 | Coding | 11 | 1147 | gaagaggcctcggccatgga | 39 | 115 | 1 |
| 217344 | Coding | 11 | 1209 | ggctcccccacgacggtggt | 0 | 116 | 1 |
| 217345 | Coding | 11 | 1240 | ggtcgggtgctccagcttgg | 28 | 117 | 1 |
| 217349 | Coding | 11 | 1333 | agtctctggaaggccaaatt | 3 | 118 | 1 |
| 217350 | Stop Codon | 11 | 1361 | ggctgggtcagttcacctcc | 0 | 119 | 1 |
| 217351 | 3'UTR | 11 | 1383 | ctcccaggagctggcacgcg | 47 | 120 | 1 |
| 217352 | 3'UTR | 11 | 1424 | atgcactcaagaactcggta | 60 | 121 | 1 |
| 217356 | 3'UTR | 11 | 1536 | actgactcttcccttcttaa | 39 | 122 | 1 |
| 217357 | 3'UTR | 11 | 1560 | acacactagaagtgagctta | 57 | 123 | 1 |
| 217358 | 3'UTR | 11 | 1577 | cctccaccttgagcaggaca | 45 | 124 | 1 |
| 217359 | 3'UTR | 11 | 1599 | caccaaggcccataaatatc | 6 | 125 | 1 |
| 217360 | 3'UTR | 11 | 1605 | agaaaccaccaaggcccata | 0 | 126 | 1 |
| 217361 | 3'UTR | 11 | 1653 | gccagggccaagtgtctgtc | 46 | 127 | 1 |
| 217362 | 3'UTR | 11 | 1685 | tggagtcactaaggactgcc | 45 | 128 | 1 |
| 217363 | 3'UTR | 11 | 1715 | gggacatggcctctgcctct | 0 | 129 | 1 |
| 217364 | 3'UTR | 11 | 1746 | ggtacgaggaacccgacctg | 43 | 130 | 1 |

TABLE 2-continued

Inhibition of mouse diacylglycerol acyl-
transferase 2 mRNA levels by chimeric phosphorothioate
oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 217365 | 3'UTR | 11 | 1772 | gccagctgtgccctcagcct | 0 | 131 | 1 |
| 217366 | 3'UTR | 11 | 1815 | ccaagccgggcagtccagat | 18 | 132 | 1 |
| 217367 | 3'UTR | 11 | 1861 | gggtaggctcagattggaga | 35 | 133 | 1 |
| 217368 | 3'UTR | 11 | 1908 | cggcacctgtgggacagccg | 32 | 134 | 1 |
| 217369 | 3'UTR | 11 | 1946 | agagtgaaaccagccaacag | 23 | 135 | 1 |
| 217370 | 3'UTR | 11 | 2002 | gctcaggaggatatgcgcca | 90 | 136 | 1 |
| 217371 | 3'UTR | 11 | 2033 | aagcccttcctcacaccaga | 9 | 137 | 1 |
| 217372 | 3'UTR | 11 | 2055 | ggcacctctgtgaagagaag | 24 | 138 | 1 |
| 217373 | 3'UTR | 11 | 2086 | tcctggacccagtgtgctgc | 32 | 139 | 1 |
| 217374 | 3'UTR | 11 | 2124 | cacacacgtgaggcttggtt | 31 | 140 | 1 |
| 217375 | 3'UTR | 11 | 2209 | atacaaaagtgtgacatggc | 30 | 141 | 1 |
| 217376 | 3'UTR | 11 | 2230 | tccatttattagtctaggaa | 76 | 142 | 1 |

As shown in Table 2, SEQ ID NOs 101, 109, 114, 115, 120, 121, 122, 123, 124, 127, 128, 130, 133, 136 and 142 demonstrated at least 35% inhibition of mouse diacylglycerol acyltransferase 2 expression in this experiment and are therefore preferred. More preferred are SEQ ID NOs 142, 109 and 121. The target regions to which these preferred sequences are complementary are herein referred to as "preferred target segments" and are therefore preferred for targeting by compounds of the present invention. These preferred target segments are shown in Table 3. These sequences are shown to contain thymine (T) but one of skill in the art will appreciate that thymine (T) is generally replaced by uracil (U) in RNA sequences. The sequences represent the reverse complement of the preferred antisense compounds shown in Tables 1 and 2. "Target site" indicates the first (5'-most) nucleotide number on the particular target nucleic acid to which the oligonucleotide binds. Also shown in Table 3 is the species in which each of the preferred target segments was found.

TABLE 3

Sequence and position of preferred target segments
identified in diacylglycerol acyltransferase 2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 134026 | 4 | 579 | cccaagaaaggtggcaggag | 20 | H. sapiens | 143 |
| 134028 | 4 | 639 | cgagactactttcccatcca | 21 | H. sapiens | 144 |
| 134030 | 4 | 649 | ttcccatccagctggtgaag | 23 | H. sapiens | 145 |
| 134031 | 4 | 654 | atccagctggtgaagacaca | 24 | H. sapiens | 146 |
| 134032 | 4 | 659 | gctggtgaagacacacaacc | 25 | H. sapiens | 147 |
| 134033 | 4 | 664 | tgaagacacacaacctgctg | 26 | H. sapiens | 148 |
| 134034 | 4 | 669 | acacacaacctgctgaccac | 27 | H. sapiens | 149 |
| 134035 | 4 | 674 | caacctgctgaccaccagga | 28 | H. sapiens | 150 |
| 134036 | 4 | 679 | tgctgaccaccaggaactat | 29 | H. sapiens | 151 |
| 134037 | 4 | 684 | accaccaggaactatatctt | 30 | H. sapiens | 152 |
| 134038 | 4 | 689 | caggaactatatctttggat | 31 | H. sapiens | 153 |
| 134039 | 4 | 694 | actatatctttggataccac | 32 | H. sapiens | 154 |

TABLE 3-continued

Sequence and position of preferred target segments
identified in diacylglycerol acyltransferase 2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 134040 | 4 | 723 | atcatgggcctgggtgcctt | 33 | H. sapiens | 155 |
| 134041 | 4 | 846 | gagtacctgatgtctggagg | 34 | H. sapiens | 156 |
| 134044 | 4 | 909 | aagaatgggagtggcaatgc | 35 | H. sapiens | 157 |
| 134045 | 4 | 914 | tgggagtggcaatgctatca | 36 | H. sapiens | 158 |
| 134046 | 4 | 919 | gtggcaatgctatcatcatc | 37 | H. sapiens | 159 |
| 134047 | 4 | 924 | aatgctatcatcatcgtggt | 38 | H. sapiens | 160 |
| 134049 | 4 | 963 | ctgagctccatgcctggcaa | 39 | H. sapiens | 161 |
| 134052 | 4 | 1110 | tcctggggccgatgggtcca | 40 | H. sapiens | 162 |
| 134053 | 4 | 1115 | gggccgatgggtccagaaga | 41 | H. sapiens | 163 |
| 134054 | 4 | 1120 | gatgggtccagaagaagttc | 42 | H. sapiens | 164 |
| 134055 | 4 | 1125 | gtccagaagaagttccagaa | 43 | H. sapiens | 165 |
| 134057 | 4 | 1197 | gacacctgggggctggtgcc | 44 | H. sapiens | 166 |
| 134058 | 4 | 1202 | ctggggctggtgccctact | 45 | H. sapiens | 167 |
| 134059 | 4 | 1207 | ggctggtgccctactccaag | 46 | H. sapiens | 168 |
| 134062 | 4 | 1309 | ccatgtacatggaggccctg | 47 | H. sapiens | 169 |
| 134063 | 4 | 1314 | tacatggaggccctggtgaa | 48 | H. sapiens | 170 |
| 134064 | 4 | 1319 | ggaggccctggtgaagctct | 49 | H. sapiens | 171 |
| 134069 | 4 | 1469 | gtcatgggtgtctgtgggtt | 50 | H. sapiens | 172 |
| 134070 | 4 | 1474 | gggtgtctgtgggttattta | 51 | H. sapiens | 173 |
| 134071 | 4 | 1479 | tctgtgggttatttaaaaga | 52 | H. sapiens | 174 |
| 250517 | 18 | 21985 | tgaggaggatgctcttttgt | 53 | H. sapiens | 175 |
| 250518 | 18 | 23110 | tggactgaagcatttatagt | 54 | H. sapiens | 176 |
| 250520 | 18 | 31611 | tcccatccaggtaaagtgct | 56 | H. sapiens | 177 |
| 250521 | 18 | 33686 | catctgcctcatttcactga | 57 | H. sapiens | 178 |
| 250522 | 18 | 35303 | ttgatgtcacctcttttgag | 58 | H. sapiens | 179 |
| 250524 | 18 | 39106 | tcccttccagagctgacctg | 60 | H. sapiens | 180 |
| 250525 | 18 | 37108 | cccatggaggtccaggggaa | 61 | H. sapiens | 181 |
| 250526 | 4 | 46 | ggctgtttctctcgcgccac | 62 | H. sapiens | 182 |
| 250527 | 4 | 134 | gctctgcgcgaagccctggc | 63 | H. sapiens | 183 |
| 250528 | 4 | 222 | gcttcagccatgaagaccct | 64 | H. sapiens | 184 |
| 250529 | 4 | 246 | gccgcctactccggggtcct | 65 | H. sapiens | 185 |
| 250530 | 4 | 441 | atctcagtgctccagtgggt | 66 | H. sapiens | 186 |
| 250532 | 4 | 987 | gcagtcaccctgcggaaccg | 68 | H. sapiens | 187 |
| 250533 | 4 | 1387 | aggtgaactgagccagcctt | 69 | H. sapiens | 188 |
| 250534 | 4 | 1401 | agccttcggggccaactccc | 70 | H. sapiens | 189 |
| 250535 | 4 | 1414 | aactccctggaggaaccagc | 71 | H. sapiens | 190 |
| 250536 | 4 | 1449 | tgctctgtaaatttggaagt | 72 | H. sapiens | 191 |

TABLE 3-continued

Sequence and position of preferred target segments identified in diacylglycerol acyltransferase 2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 250537 | 4 | 1584 | gcttgccctgttctaggtgg | 73 | H. sapiens | 192 |
| 250539 | 4 | 1647 | ttcttcccttcctgaagtga | 75 | H. sapiens | 193 |
| 250540 | 4 | 1679 | agtcttcttggggaagaagg | 76 | H. sapiens | 194 |
| 250541 | 4 | 1707 | tagtgacttggaccagttag | 77 | H. sapiens | 195 |
| 250542 | 4 | 1724 | tagatgattcactttttgcc | 78 | H. sapiens | 196 |
| 250544 | 4 | 1763 | agccacttctcatacaagcc | 80 | H. sapiens | 197 |
| 250545 | 4 | 1802 | acgtcgtctagtcctgaaa | 81 | H. sapiens | 198 |
| 250546 | 4 | 1946 | cctagtcactcatatcggag | 82 | H. sapiens | 199 |
| 250547 | 4 | 1969 | ggactggcctccaggatgag | 83 | H. sapiens | 200 |
| 250548 | 4 | 1974 | ggcctccaggatgaggatgg | 84 | H. sapiens | 201 |
| 250549 | 4 | 1989 | gatggggtggcaatgacac | 85 | H. sapiens | 202 |
| 250550 | 4 | 2055 | gccgccaccatgagctaggt | 86 | H. sapiens | 203 |
| 250551 | 4 | 2067 | agctaggtggagtaactggt | 87 | H. sapiens | 204 |
| 250552 | 4 | 2088 | tttcttgggtggctgatgac | 88 | H. sapiens | 205 |
| 250553 | 4 | 2125 | tcagccttggcctggagcac | 89 | H. sapiens | 206 |
| 250554 | 4 | 2137 | tggagcacatgcttactggt | 90 | H. sapiens | 207 |
| 250555 | 4 | 2143 | acatgcttactggtggcctc | 91 | H. sapiens | 208 |
| 250556 | 4 | 2150 | tactggtggcctcagtttac | 92 | H. sapiens | 209 |
| 250558 | 4 | 2220 | ggggcctggccttctgagca | 94 | H. sapiens | 210 |
| 250559 | 4 | 2242 | agattagttccaaagcaggt | 95 | H. sapiens | 211 |
| 250560 | 4 | 2269 | gaacccaagcctcacttttc | 96 | H. sapiens | 212 |
| 250561 | 4 | 2367 | ttgcaccatgtcagactttt | 97 | H. sapiens | 213 |
| 134018 | 11 | 99 | cagctcccggagctcagcgc | 101 | M. musculus | 214 |
| 134027 | 11 | 586 | tgcgaaactgggccgtgtgg | 109 | M. musculus | 215 |
| 134051 | 11 | 1051 | atgaggtatacaagcaggtg | 114 | M. musculus | 216 |
| 134056 | 11 | 1147 | tccatggccgaggcctcttc | 115 | M. musculus | 217 |
| 134067 | 11 | 1383 | cgcgtgccagctcctgggag | 120 | M. musculus | 218 |
| 134068 | 11 | 1424 | taccgagttcttgagtgcat | 121 | M. musculus | 219 |
| 134072 | 11 | 1536 | ttaagaagggaagagtcagt | 122 | M. musculus | 220 |
| 134073 | 11 | 1560 | taagctcacttctagtgtgt | 123 | M. musculus | 221 |
| 134074 | 11 | 1577 | tgtcctgctcaaggtggagg | 124 | M. musculus | 222 |
| 134077 | 11 | 1653 | gacagacacttggccctggc | 127 | M. musculus | 223 |
| 134078 | 11 | 1685 | ggcagtccttagtgactcca | 128 | M. musculus | 224 |
| 134080 | 11 | 1746 | caggtcgggttcctcgtacc | 130 | M. musculus | 225 |
| 134083 | 11 | 1861 | tctccaatctgagcctaccc | 133 | M. musculus | 226 |

TABLE 3-continued

Sequence and position of preferred target segments
identified in diacylglycerol acyltransferase 2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 134086 | 11 | 2002 | tggcgcatatcctcctgagc | 136 | M. musculus | 227 |
| 134092 | 11 | 2230 | ttcctagactaataaatgga | 142 | M. musculus | 228 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of diacylglycerol acyltransferase 2.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 17

Western Blot Analysis of Diacylglycerol Acyltransferase 2 Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to diacylglycerol acyltransferase 2 is used, with a radiolabeled or fluorescently labeled secondary antibody directed against the primary antibody species. Bands are visualized using a PHOSPHORIMAGER? (Molecular Dynamics, Sunnyvale Calif.).

Example 18

Effects of Antisense Inhibition on Diacylglycerol Acyltransferase 2 Levels: In Vivo Studies in a Diet-induced Model of Obesity The C57BL/6 mouse strain is reported to be susceptible to hyperlipidemia-induced atherosclerotic plaque formation. Accordingly, these mice were fed a high-fat diet and used in the following studies to evaluate the effects of diacylglycerol acyltransferase 2 antisense oligonucleotides on mRNA expression in a model of diet-induced obesity.

Male C57BL/6 mice (7-weeks old) received a 60% fat diet for 8 weeks and subsequently received subcutaneous-injections of ISIS 217376 (SEQ ID No: 142) or a control oligonucleotide ISIS 141923 (CCTTCCCTGAAGGTTCCTCC, SEQ ID NO: 229) at a dose of 25 mg/kg twice per week for 7 weeks. ISIS 141923 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. A group of saline injected mice served as untreated controls. Each treatment group contained 6-8 mice.

After the 8 week treatment period, mice were sacrificed and diacylglycerol acyltransferase 2 (DGAT2) mRNA levels were evaluated in liver, brown adipose tissue (BAT) and white adipose tissue (WAT). In addition, diacylglycerol acyltransferase 1 (DGAT1) mRNA levels were measured in these tissues. mRNA expression levels were quantitated by real-time PCR as described in other examples herein. The results are presented in Table 4 and are expressed as percent inhibition relative to saline treated mice receiving a high fat diet. A "+" preceding the number indicates that gene expression was increased, rather than inhibited.

TABLE 4

Antisense inhibition of diacylglycerol acyltransferase 2 expression in liver, brown adipose and white adipose tissues from diet-induced obese mice

| | % Inhibition of diacylglycerol acyltransferase mRNAs | | | | | |
|---|---|---|---|---|---|---|
| | Liver | | WAT | | BAT | |
| ISIS # | DGAT 2 | DGAT 1 | DGAT 2 | DGAT 1 | DGAT 2 | DGAT 1 |
| 141923 | 2 | 7 | +26 | +23 | 25 | 33 |
| 217376 | 80 | 47 | 87 | 0 | 78 | 21 |

The data demonstrate that diacylglycerol acyltransferase 2 antisense oligonucleotide treatment can effectively inhibit target mRNA expression in liver, brown adipose and white adipose tissue. Diacylglycerol acyltransferase 1 expression levels were slightly lowered. Although target levels were reduced, no significant changes were observed in food intake, body weight, metabolic rate or adipose tissue weight in diet-induced obese mice following treatment with diacylglycerol acyltransferase 2 antisense oligonucleotide.

Example 19

Effects of Antisense Inhibition of Diacylglycerol Acyltransferase 2 on Markers of Lipid and Glucose Metabolism In accordance with the present invention, ISIS 217376 (SEQ ID NO: 142) was tested for its ability to affect lipid and glucose metabolism. The diet-induced obese mice that received antisense oligonucleotide treatment, as described in Example 18, were further evaluated at the end of the 7 week treatment period for levels of serum free fatty acids, triglycerides (TRIG), cholesterol, including total cholesterol (CHOL) and high (HDL) and low (LDL) density lipoprotein cholesterol. The data, expressed as percent reduction relative to the saline control, are presented in Table 5.

TABLE 5

Effects of antisense inhibition of diacylglycerol acyltransferase 2 on serum cholesterol and lipids in diet-induced obese mice

| | Percent Reduction in | | | | |
|---|---|---|---|---|---|
| | Serum Lipids | | Cholesterol | | |
| ISIS # | Free Fatty Acids | TRIG | Total CHOL | HDL CHOL | LDL CHOL |
| 141923 | 17 | 13 | 13 | 11 | 30 |
| 217376 | 33 | 41 | 31 | 28 | 24 |

The results demonstrate that antisense inhibition of diacylglycerol acyltransferase 2 expression, which was presented in Example 18, leads to significant reductions in serum free fatty acids, serum triglycerides, HDL cholesterol and total serum cholesterol. No significant change was observed in LDL cholesterol levels. With respect to glucose metabolism, treatment with antisense oligonucleotide targeted to diacylglycerol acyltransferase 2 did reduce plasma insulin by 69% at the end of the treatment period, but did not change plasma glucose levels, glucose tolerance or insulin tolerance in diet-induced obese mice.

Example 20

Effects of Antisense Inhibition of Diacylglycerol Acyltransferase 2 on Hepatic Triglycerides and Steatosis in Diet-Induced Obese Mice In accordance with the present invention, ISIS 217376 (SEQ ID NO: 142) was tested for its ability to affect triglyceride and glycogen content in the livers of diet-indueced obese mice. The diet-induced obese mice that received antisense oligonucleotide treatment, as described in Example 18, were further evaluated at the end of the 7 week treatment period for hepatic triglycerides and glycogen content. Hepatic triglyceride content was used to assess hepatic steatosis, or clearing of lipids from the liver. The data are shown in Table 6 and are expressed as percent reduction relative to saline-treated, high-fat diet mice.

TABLE 6

Effects of antisense inhibition of diacylglycerol acyltransferase 2 on hepatic lipid and glycogen content

| | Percent reduction in | |
|---|---|---|
| ISIS # | Hepatic Triglycerides | Hepatic Glycogen |
| 141923 | 30 | 5 |
| 217376 | 56 | 3 |

The results in Table 6 demonstrate that treatment with antisense oligonucleotide targeted to diacylglycerol acyltransferase 2 yields a marked reduction in hepatic triglyceride content compared to saline- and control oligonucleotide-treated mice, indicating an improvement in hepatic steatosis. No significant change in hepatic glycogen was observed.

Example 21

Effects of Antisense Inhibition of Diacylglycerol Acyltransferase 2 on Hepatic Lipogenic and Gluconeogenic Genes In accordance with the present invention, ISIS 217376 (SEQ ID NO: 142) was tested for its ability to affect the expression of genes involved in fatty acid synthesis and glucose metabolism. The diet-induced obese mice that received antisense oligonucleotide treatment, as described in Example 18, were further evaluated at the end of the 7 week treatment period for expression levels of genes that participate in lipid metabolism, gluconeogenesis and glucose metabolism. mRNA levels in liver and white adipose tissue were quantitated by real-time PCR as described in other examples herein, using primer-probe sets that were generated using the GenBank accession numbers provided in Table 7. The results are presented as percent change relative to saline-treated, high fat diet control mice and are shown in Table 7.

TABLE 7

Lipid and glucose metabolism gene expression following antisense inhibition of diacylglycerol acyltransferase 2

| | | Percent Change | |
|---|---|---|---|
| Gene Name | GenBank Accession # | ISIS 141923 | ISIS 217376 |
| Liver tissue | | | |
| carnitine palmitoyltransferase I | NM_001876.1 | −17 | −49 |
| acetyl-CoA carboxylase 1 | NM_000664.1 | −18 | −66 |
| acetyl-CoA carboxylase 2 | NM_001093.1 | −5 | −90 |
| fatty acid synthase | U29344.1 | −48 | −50 |
| glucose-6-phosphatase | NM_000151.1 | −27 | −9 |
| phosphoenolpyruvate carboxykinase 1 | NM_011044.1 | +14 | +23 |
| pyruvate kinase | NM_000298.2 | −47 | −73 |
| glucose transporter type 2 | NM_000340.1 | −6 | +8 |
| pyruvate dehydrogenase alpha subunit | NM_000284.1 | −22 | −25 |
| glycogen phosphorylase | M14636.1 | −2 | −19 |
| HMGCoA reductase | NM_000859.1 | −19 | −45 |
| White adipose tissue | | | |
| glucose transporter 4 | M20747.1 | +185 | +8 |
| glucose transporter type 2 | NM_000340.1 | −7 | +3 |
| hormone sensitive lipase | NM_005357.1 | +75 | +42 |
| lipoprotein lipase | NM_000237.1 | +113 | −25 |

These data demonstrate that antisense inhibition of diacylglycerol acyltransferase 2, in addition to reducing the expression of target mRNA in diet-induced obese mice, is also capable of altering the expression of other genes that participate in lipid and glucose metabolism. For example, the expression levels of HMG-CoA reductase, acetyl-CoA carboxylase 1 and acetyl-CoA carboxylase 2, carnitine palmitoyltransferase I and glycogen phosphorylase, which participate in cholesterol biosynthesis, fatty acid synthesis, fatty acid oxidation and glycogen metabolism, respectively, were reduced following ISIS 217376 treatment of mice. Lipoprotein lipase, which participates in fatty acid storage in adipose tissue, exhibited reduced expression as well. Conversely, expression of enzymes that participate in gluconeogenesis, glucose-6-phosphatase and phosphoenolpyruvate carboxykinase 1, was not significantly reduced. Expression levels of hormone sensitive lipase and phosphoenolpyruvate carboxykinase 1 were significantly increased following antisense inhibition of diacylglycerol acyltransferase.

Example 22

Effects of Antisense Inhibition of Diacylglycerol Acyltransferase 2 in the ob/ob Mouse Model of Obesity Leptin is a hormone produced by fat that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and treatments designed to reduce obesity.

In accordance with the present invention, the effects of antisense inhibition of diacylglycerol acyltransferase 2 were investigated in the ob/ob mouse model of obesity. Seven-week old male C57B1/6J-Lepr ob/ob mice were fed a diet with a fat content of 10-15% and were subcutaneously injected with ISIS 217376 (SEQ ID NO: 142) or ISIS 116847 (CTGCTAGCCTCTGGATTTGA, SEQ ID NO: 230) at a dose of 25 mg/kg twice per week for 4 weeks. ISIS 116847 was used as a positive control oligonucleotide that does not target the diacylglycerol acyltransferase 2 gene. ISIS 116847 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. A group of saline-injected mice served as an untreated control. Each treatment group consisted of 8 mice.

At the end of the four week treatment period, the mice were sacrificed and target expression, as well as diacylglycerol acyltransferase 1 expression, was measured in liver and fat tissue. mRNA expression was quantitated by real-time PCR as described in other examples herein. These organs were also weighed. The data are expressed as percent inhibition relative to saline control and are presented in Table 8. A "+" preceding the number indicates that gene expression was increased, rather than inhibited.

TABLE 8

Antisense inhibition of diacylglycerol acyltransferase 2 mRNA expression in liver and fat tissues from ob/ob mice

| | % Inhibition of diacylglycerol acyltransferase mRNAs | | | |
|---|---|---|---|---|
| | Liver | | Fat tissue | |
| ISIS # | DGAT 2 | DGAT 1 | DGAT 2 | DGAT 1 |
| 116847 | 17 | 11 | 14 | 16 |
| 217376 | 83 | 7 | 90 | +14 |

These results illustrate that treatment of ob/ob mice with an antisense oligonucleotide targeted to diacylglycerol acyltransferase 2 effectively inhibits the expression of target mRNA in both liver and fat tissues, whereas diacylglycerol acyltransferase 1 expression is not significantly changed. Liver weight was reduced by 21% in ob/ob mice treated with the antisense oligonucleotide of the present invention, but fat tissue weight was not significantly changed. No significant reduction in diacylglycerol acyltransferase 1 mRNA expression was observed.

Example 23

Effects of Antisense Inhibition of Diacylglycerol Acyltransferase 2 in ob/ob Mice on Serum and Liver Lipid Content In accordance with the present invention, ISIS 217376 (SEQ ID NO: 142) was tested for its effect on serum lipids and free fatty acids, as well as tissue triglyceride levels in ob/ob mice.

The ob/ob mice that received antisense oligonucleotide treatment, as described in Example 22, were further evaluated at the end of the 4 week treatment period for serum lipids, serum free fatty acids, serum cholesterol (CHOL), liver triglycerides, and fat tissue triglycerides. Hepatic steatosis, or clearing of lipids from the liver, can be assessed by measuring the liver triglyceride content. The data, shown in Table 9, are expressed as percent reduction relative to saline-treated control ob/ob mice. As in Example 22, the results are the average of measurements from 8 mice.

TABLE 9

Serum and tissue lipid content following antisense inhibition of diacylglycerol acyltransferase 2

| | % Reduction of serum and tissue lipid content | | | | |
|---|---|---|---|---|---|
| | Serum Lipids | | | | |
| | | | Free Fatty | Tissue Triglycerides | |
| ISIS # | Triglyceride | CHOL | Acids | Liver | Fat |
| 116847 | 22 | 10 | 8 | 12 | 14 |
| 217376 | 0 | 0 | 22 | 21 | 13 |

The data illustrate that antisense inhibition of diacylglycerol acyltransferase 2 in ob/ob mice causes a reduction in triglyceride levels in liver tissue and in serum free fatty acids. The decrease in liver tissue triglyceride content indicates an improvement in hepatic steatosis. No significant change in serum triglyceride, fat tissue triglyceride or cholesterol was observed.

Example 24

Plasma Insulin and Glucose Levels Following Antisense Inhibition of Diacylglycerolacyltransferase 2 in ob/ob Mice In accordance with the present invention, the ob/ob mice treated as described in Example 22 were further evaluated for insulin and glucose levels. Plasma glucose was measured at the start of the antisense oligonucleotide treatment and after 2 weeks and 4 weeks of treatment. Plasma insulin was measured following 2 weeks and 4 weeks of treatment. After 3 weeks of treatment, glucose and insulin tolerance tests were also performed in mice fasting for 16 and 4 hours, respectively. Relative to saline-treated control ob/ob mice, plasma insulin in ob/ob mice receiving ISIS 217376 was reduced by 43% at both 2 weeks and 4 weeks of antisense oligonucleotide treatment. No significant change was observed in plasma glucose levels, and glucose levels following insulin and glucose challenge were higher than in saline-treated control mice.

Example 25

Effects of Antisense Inhibition of Diacylglycerol Acyltransferase 2 in the db/db Mouse Model of Obesity A deficiency in the leptin hormone receptor mice also results in obesity and hyperglycemia. These mice are referred to as db/db mice and, like the ob/ob mice, are used as a mouse model of obesity.

In accordance with the present invention, antisense inhibition of diacylglycerol acyltransferase 2 with ISIS 217276 (SEQ ID NO: 142) was investigated for its ability to effect target mRNA expression, triglyceride levels and plasma glucose levels in db/db mice. Six-week old male C57B1/6J-Lepr db/db mice were fed a 15-20% fat diet and received subcutaneous injections of ISIS 217376 (SEQ ID NO: 142) or the control oligonucleotide ISIS 116847 (CTGCTAGCCTCTG-GATTTGA, SEQ ID NO: 230) at a dose of 25 mg/kg twice per week for 4 weeks. A group of saline injected mice served as untreated controls. Each treatment group contained 4 to 8 mice.

After the 4 week treatment period, mice were sacrificed and diacylglycerol acyltransferase 2 mRNA levels (n=4 mice) were evaluated in liver, brown adipose tissue (BAT) and white adipose tissue (WAT). Diacylglycerol acyltransferase 1 mRNA levels were also measured in these tissues. mRNA expression levels were quantitated by real-time PCR as described in other examples herein. In addition, liver triglycerides (n=6 mice) and plasma glucose (n=8 mice) were measured. The results are presented in Table 10 and are expressed as percent inhibition (for mRNA expression) or reduction (for glucose and triglycerides) relative to saline treated mice. An increase in gene expression or liver triglycerides is indicated by a "+" preceding the number. Hepatic steatosis, or clearing of lipids from the liver, was assessed by routine histological analysis of frozen liver tissue sections stained with oil red O stain, which is commonly used to visualize lipid deposits, and counterstained with hematoxylin and eosin, to visualize nuclei and cytoplasm, respectively.

TABLE 10

Effects of antisense inhibition of diacylglycerol acyltransferase 2 in db/db mice

| Biological Marker Measured | | Treatment | |
|---|---|---|---|
| | | ISIS 116847 | ISIS 217376 |
| | Week | | |
| % Reduction in plasma glucose | 0 | 0 | 0 |
| | 2 | 34 | 5 |
| | 4 | 55 | 14 |
| % Reduction in liver triglycerides | 4 | +41 | 41 |
| mRNA expression in tissue | | | |
| % Inhibition of diacyglycerol acyltransferase 2 | Liver | +17 | 95 |
| | WAT | 0 | 80 |
| | BAT | 19 | 87 |
| % Inhibition of diacyglycerol acyltransferase 1 | Liver | +9 | +5 |
| | WAT | +11 | 5 |
| | BAT | 13 | 28 |

These data illustrate that target mRNA expression can be effectively inhibited in liver, brown adipose and white adipose tissue of db/db mice treated with the oligonucleotide of the present invention. Furthermore, inhibition of diacylglycerol acyltransferase 2 expression in db/db mice results in a reduction in hepatic triglyceride content and improved steatosis. Similar observations regarding improvement of hepatic steatosis were made in two other mouse models of obesity, the diet-induced obese mice and ob/ob mice, as described in other examples herein. No significant change in plasma glucose was observed.

---

What is claimed is:

1. A modified oligonucleotide compound that is 12 to 50 nucleobases in length and targeted to a region comprising nucleotide 901 to 950 of the nucleic acid molecule encoding diacylglycerol acyltransferase 2 in SEQ ID NO: 4, wherein said compound is at least 80% complementary to said nucleic acid molecule encoding diacylglycerol acyltransferase 2, and wherein said compound comprises at least an 8 nucleobase portion of SEQ ID NO: 36, 37 or 38.

2. The compound of claim 1, wherein said compound is 15 to 30 nucleobases in length.

3. The compound of claim 1 comprising an antisense oligonucleotide.

4. The compound of claim 1 comprising a DNA oligonucleotide.

5. The compound of claim 1 comprising a RNA oligonucleotide.

6. The compound of claim 1 comprising a chimeric oligonucleotide.

7. The compound of claim 1 wherein at least a portion of said compound hybridizes with RNA to form an oligonucleotide-RNA duplex.

8. The compound of claim 1 having at least 90% complementarity with said nucleic acid molecule encoding diacylglycerol acyltransferase 2.

9. The compound of claim 1 having at least 95% complementarity with said nucleic acid molecule encoding diacylglycerol acyltransferase 2.

10. The compound of claim 1 having 100% complementarity with said nucleic acid molecule encoding diacylglycerol acyltransferase 2.

11. The compound of claim 1 having at least one modified internucleoside linkage, sugar moiety, or nucleobase.

12. The compound of claim 1 having at least one 2'-O-methoxyethyl sugar moiety.

13. The compound of claim 1 having at least one phosphorothioate internucleoside linkage.

14. The compound of claim 1 having at least one 5-methylcytosine.

15. A kit or assay device comprising the compound of claim 1.

16. The compound of claim 1, wherein said compound is 20 nucleobases in length.

17. The compound of claim 10 having at least one modified internucleoside linkage, sugar moiety, or nucleobase.

18. A modified oligonucleotide compound that is 20 nucleobases in length and targeted to a nucleic acid molecule encoding diacylglycerol acyltransferase 2 (SEQ ID NO: 4), wherein said compound has the nucleobase sequence of SEQ ID NO: 35.

19. The compound of claim 18, wherein said compound is an antisense oligonucleotide comprising:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

20. The compound of claim 19, wherein the antisense oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

21. The compound of claim 20, wherein each cytosine is a 5-methylcytosine.

22. The compound of claim 20, wherein the deoxynucleosides are 2'-deoxynucleosides.

23. The compound of claim 21, wherein the deoxynucleosides are 2'-deoxynucleosides.

24. The compound of claim 1, wherein said compound comprises at least an 8 nucleobase portion of SEQ ID NO: 36.

25. The compound of claim 1, wherein said compound comprises at least an 8 nucleobase portion of SEQ ID NO: 37.

26. The compound of claim 1, wherein said compound comprises at least an 8 nucleobase portion of SEQ ID NO: 38.

27. A modified oligonucleotide compound that is 20 to 50 nucleobases in length and targeted to a region comprising nucleotide 901 to 950 of the nucleic acid molecule encoding diacylglycerol acyltransferase 2 in SEQ ID NO: 4, wherein said compound is 100% complementary to said nucleic acid molecule encoding diacylglycerol acyltransferase 2, and wherein said compound comprises the nucleotide sequence of SEQ ID NO: 35.

28. The compound of claim 27, wherein said compound that is 20 to 30 nucleobases in length.

29. The compound of claim 27 comprising an oligonucleotide.

30. The compound of claim 29 comprising an antisense oligonucleotide.

31. The compound of claim 29 comprising a DNA oligonucleotide.

32. The compound of claim 29 comprising a RNA oligonucleotide.

33. The compound of claim 29 comprising a chimeric oligonucleotide.

34. The compound of claim 29 wherein at least a portion of said compound hybridizes with RNA to form an oligonucleotide-RNA duplex.

35. The compound of claim 27 having at least one modified internucleoside linkage, sugar moiety, or nucleobase.

36. The compound of claim 27 having at least one 2'-O-methoxyethyl sugar moiety.

37. The compound of claim 27 having at least one phosphorothioate internucleoside linkage.

38. The compound of claim 27 having at least one 5-methylcytosine.

39. A kit or assay device comprising the compound of claim 27.

40. The compound of claim 27, wherein said compound is 20 nucleobases in length.

\* \* \* \* \*

SEQUENCE LISTING

<160> NUMBER OF SEQ ID NOS: 233

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                           20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                           20

<210> SEQ ID NO 3
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 3
atgcattctg cccccaagga                                               20

<210> SEQ ID NO 4
<211> LENGTH: 2439
<212> TYPE: DNA
<213> ORGANISM: H. sapiens
<220> FEATURE:
<220> FEATURE:
<221> NAME/KEY: CDS
<222> LOCATION: (231)...(1397)

<400> SEQUENCE: 4

```
ctccgggaac gccagcgccg cggctgccgc tctgctggg gtctaggctg tttctctcgc      60
gccaccactg gccgccggcc gcagctccag gtgtcctagc cgcccagcct cgacgccgtc     120
ccgggacccc tgtgctctgc gcgaagccct ggccccgggg gccggggcat gggccagggg    180
cgcggggtga agcggcttcc cgcggggccg tgactgggcg ggcttcagcc atg aag       236
                                                      Met Lys
                                                        1 acc ctc ata gcc gcc tac tcc ggg gtc ctg cgc ggc gag cgt cag gcc      284
Thr Leu Ile Ala Ala Tyr Ser Gly Val Leu Arg Gly Glu Arg Gln Ala
        5                  10                  15 gag gct gac cgg agc cag cgc tct cac gga gga cct gcg ctg tcg cgc      332
Glu Ala Asp Arg Ser Gln Arg Ser His Gly Gly Pro Ala Leu Ser Arg
 20                  25                  30 gag ggg tct ggg aga tgg ggc act gga tcc agc atc ctc tcc gcc ctc      380
Glu Gly Ser Gly Arg Trp Gly Thr Gly Ser Ser Ile Leu Ser Ala Leu
 35                  40                  45                  50 cag gac ctc ttc tct gtc acc tgg ctc aat agg tcc aag gtg gaa aag      428
Gln Asp Leu Phe Ser Val Thr Trp Leu Asn Arg Ser Lys Val Glu Lys
                55                  60                  65 cag cta cag gtc atc tca gtg ctc cag tgg gtc ctg tcc ttc ctt gta      476
Gln Leu Gln Val Ile Ser Val Leu Gln Trp Val Leu Ser Phe Leu Val
         70                  75                  80 ctg gga gtg gcc tgc agt gcc atc ctc atg tac ata ttc tgc act gat      524
Leu Gly Val Ala Cys Ser Ala Ile Leu Met Tyr Ile Phe Cys Thr Asp
     85                  90                  95 tgc tgg ctc atc gct gtg ctc tac ttc act tgg ctg gtg ttt gac tgg      572
Cys Trp Leu Ile Ala Val Leu Tyr Phe Thr Trp Leu Val Phe Asp Trp
100                 105                 110 aac aca ccc aag aaa ggt ggc agg agg tca cag tgg gtc cga aac tgg      620
Asn Thr Pro Lys Lys Gly Gly Arg Arg Ser Gln Trp Val Arg Asn Trp
115                 120                 125                 130 gct gtg tgg cgc tac ttt cga gac tac ttt ccc atc cag ctg gtg aag      668
Ala Val Trp Arg Tyr Phe Arg Asp Tyr Phe Pro Ile Gln Leu Val Lys
                135                 140                 145 aca cac aac ctg ctg acc acc agg aac tat atc ttt gga tac cac ccc      716
Thr His Asn Leu Leu Thr Thr Arg Asn Tyr Ile Phe Gly Tyr His Pro
        150                 155                 160 cat ggt atc atg ggc ctg ggt gcc ttc tgc aac ttc agc aca gag gcc      764
His Gly Ile Met Gly Leu Gly Ala Phe Cys Asn Phe Ser Thr Glu Ala
165                 170                 175 aca gaa gtg agc aag aag ttc cca ggc ata cgg cct tac ctg gct aca      812
Thr Glu Val Ser Lys Lys Phe Pro Gly Ile Arg Pro Tyr Leu Ala Thr
180                 185                 190 ctg gca ggc aac ttc cga atg cct gtg ttg agg gag tac ctg atg tct      860
```

```
                                           -continued

Leu Ala Gly Asn Phe Arg Met Pro Val Leu Arg Glu Tyr Leu Met Ser
195                 200                 205                 210 gga ggt atc tgc cct gtc agc cgg gac acc ata gac tat ttg ctt tca      908
Gly Gly Ile Cys Pro Val Ser Arg Asp Thr Ile Asp Tyr Leu Leu Ser
            215                 220                 225 aag aat ggg agt ggc aat gct atc atc atc gtg gtc ggg ggt gcg gct      956
Lys Asn Gly Ser Gly Asn Ala Ile Ile Ile Val Val Gly Gly Ala Ala
        230                 235                 240 gag tct ctg agc tcc atg cct ggc aag aat gca gtc acc ctg cgg aac     1004
Glu Ser Leu Ser Ser Met Pro Gly Lys Asn Ala Val Thr Leu Arg Asn
    245                 250                 255 cgc aag ggc ttt gtg aaa ctg gcc ctg cgt cat gga gct gac ctg gtt     1052
Arg Lys Gly Phe Val Lys Leu Ala Leu Arg His Gly Ala Asp Leu Val
260                 265                 270 ccc atc tac tcc ttt gga gag aat gaa gtg tac aag cag gtg atc ttc     1100
Pro Ile Tyr Ser Phe Gly Glu Asn Glu Val Tyr Lys Gln Val Ile Phe
275                 280                 285                 290 gag gag ggc tcc tgg ggc cga tgg gtc cag aag aag ttc cag aaa tac     1148
Glu Glu Gly Ser Trp Gly Arg Trp Val Gln Lys Lys Phe Gln Lys Tyr
                295                 300                 305 att ggt ttc gcc cca tgc atc ttc cat ggt cga ggc ctc ttc tcc tcc     1196
Ile Gly Phe Ala Pro Cys Ile Phe His Gly Arg Gly Leu Phe Ser Ser
            310                 315                 320 gac acc tgg ggg ctg gtg ccc tac tcc aag ccc atc acc act gtt gtg     1244
Asp Thr Trp Gly Leu Val Pro Tyr Ser Lys Pro Ile Thr Thr Val Val
        325                 330                 335 gga gag ccc atc acc atc ccc aag ctg gag cac cca acc cag caa gac     1292
Gly Glu Pro Ile Thr Ile Pro Lys Leu Glu His Pro Thr Gln Gln Asp
    340                 345                 350 atc gac ctg tac cac acc atg tac atg gag gcc ctg gtg aag ctc ttc     1340
Ile Asp Leu Tyr His Thr Met Tyr Met Glu Ala Leu Val Lys Leu Phe
355                 360                 365                 370 gac aag cac aag acc aag ttc ggc ctc ccg gag act gag gtc ctg gag     1388
Asp Lys His Lys Thr Lys Phe Gly Leu Pro Glu Thr Glu Val Leu Glu
                375                 380                 385 gtg aac tga gccagccttc ggggccaact ccctggagga accagctgca atcactttt   1447
Val Asn ttgctctgta aatttggaag tgtcatgggt gtctgtgggt tatttaaaag aaattataac   1507
aattttgcta aaccattaca atgttaggtc ttttttaaga aggaaaaagt cagtatttca   1567
agttctttca cttccagctt gccctgttct aggtggtggc taaatctggg cctaatctgg   1627
gtggctcagc taacctctct tcttcccttc ctgaagtgac aaaggaaact cagtcttctt   1687
ggggaagaag gattgccatt agtgacttgg accagttaga tgattcactt tttgccccta   1747
gggatgagag gcgaaagcca cttctcatac aagccccttt attgccacta ccccacgctc   1807
gtctagtcct gaaactgcag gaccagtttc tctgccaagg ggaggagttg agagcacag    1867 ttgccccgtt gtgtgagggc agtagtaggc atctggaatg ctccagtttg atctcccttc   1927
tgccacccct acctcacccc tagtcactca tatcggagcc tggactggcc tccaggatga   1987 ggatggggt ggcaatgaca ccctgcaggg gaaaggactg cccccatgc accattgcag     2047 ggaggatgcc gccaccatga gctaggtgga gtaactggtt tttcttgggt ggctgatgac   2107
atggatgcag cacagactca gccttggcct ggagcacatg cttactggtg gcctcagttt   2167
accttcccca gatcctagat tctggatgtg aggaagagat ccctcttcag aagggcctg    2227 gccttctgag cagcagatta gttccaaagc aggtggcccc cgaacccaag cctcactttt   2287
ctgtgccttc ctgaggggt tgggccgggg aggaaaccca accctctcct gtgtgttctg    2347
```

```
ttatctcttg atgagatcat tgcaccatgt cagactttg tatatgcctt gaaataaat        2407 gaaagtgaga atccaaaaaa aaaaaaaaaa aa                                    2439

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
catacggcct tacctggcta ca                                                 22

<210> SEQ ID NO 6
<211> LENGTH: 24
<212> TYPE: DNA
<213> ORGANISM: Artificial Sequence
<220> FEATURE:
<223> OTHER INFORMATION: PCR Primer

<400> SEQUENCE: 6
cagacatcag gtactccctc aaca                                               24

<210> SEQ ID NO 7
<211> LENGTH: 22
<212> TYPE: DNA
<213> ORGANISM: Artificial Sequence
<220> FEATURE:
<223> OTHER INFORMATION: PCR Probe

<400> SEQUENCE: 7
tggcaggcaa cttccgaatg cc                                                 22

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                     19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                    20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                    20

<210> SEQ ID NO 11
```

```
<211> LENGTH: 2262
<212> TYPE: DNA
<213> ORGANISM: M. musculus
<220> FEATURE:
<220> FEATURE:
<221> NAME/KEY: CDS
<222> LOCATION: (207)...(1373)

<400> SEQUENCE: 11
ggtggccgcg cttcgctggc tttctgctca tctagggtgg cagcggctac ctacctcagc      60
tctcgccctg ctgccgccac ggcctgggcg ctgtccctca gctcccggag ctcagcgcga     120
agccctggcc ccggcggccg gggcatgggt caggggcgcg gcgtgaggcg gctttctgca     180
cggccgtgac gtgcattggc ttcagc atg aag acc ctc atc gcc gcc tac tcc     233
                              Met Lys Thr Leu Ile Ala Ala Tyr Ser
                                1               5 ggg gtc ctg cgg ggt gag cgt cgg gcg gaa gct gcc cgc agc gaa aac     281
Gly Val Leu Arg Gly Glu Arg Arg Ala Glu Ala Ala Arg Ser Glu Asn
 10              15                  20                  25 aag aat aaa gga tct gcc ctg tca cgc gag ggg tct ggg cga tgg ggc     329
Lys Asn Lys Gly Ser Ala Leu Ser Arg Glu Gly Ser Gly Arg Trp Gly
             30                  35                  40 act ggc tcc agc atc ctc tca gcc ctc caa gac atc ttc tct gtc acc     377
Thr Gly Ser Ser Ile Leu Ser Ala Leu Gln Asp Ile Phe Ser Val Thr
         45                  50                  55 tgg ctc aac aga tct aag gtg gaa aaa cag ctg cag gtc atc tca gta     425
Trp Leu Asn Arg Ser Lys Val Glu Lys Gln Leu Gln Val Ile Ser Val
     60                  65                  70 cta caa tgg gtc cta tcc ttc ctg gtg cta gga gtg gcc tgc agt gtc     473
Leu Gln Trp Val Leu Ser Phe Leu Val Leu Gly Val Ala Cys Ser Val
 75                  80                  85 atc ctc atg tac acc ttc tgc aca gac tgc tgg ctg ata gct gtg ctc     521
Ile Leu Met Tyr Thr Phe Cys Thr Asp Cys Trp Leu Ile Ala Val Leu
 90                  95                 100                 105 tac ttc acc tgg ctg gca ttt gac tgg aac acg ccc aag aaa ggt ggc     569
Tyr Phe Thr Trp Leu Ala Phe Asp Trp Asn Thr Pro Lys Lys Gly Gly
             110                 115                 120 agg aga tcg cag tgg gtg cga aac tgg gcc gtg tgg cgc tac ttc cga     617
Arg Arg Ser Gln Trp Val Arg Asn Trp Ala Val Trp Arg Tyr Phe Arg
         125                 130                 135 gac tac ttt ccc atc cag ctg gtg aag aca cac aac ctg ctg acc acc     665
Asp Tyr Phe Pro Ile Gln Leu Val Lys Thr His Asn Leu Leu Thr Thr
     140                 145                 150 agg aac tat atc ttt gga tac cac ccc cat ggc atc atg ggc ctg ggt     713
Arg Asn Tyr Ile Phe Gly Tyr His Pro His Gly Ile Met Gly Leu Gly
 155                 160                 165 gcc ttc tgt aac ttc agc aca gag gct act gaa gtc agc aag aag ttt     761
Ala Phe Cys Asn Phe Ser Thr Glu Ala Thr Glu Val Ser Lys Lys Phe
170                 175                 180                 185 cct ggc ata agg ccc tat ttg gct acg ttg gct ggt aac ttc cgg atg     809
Pro Gly Ile Arg Pro Tyr Leu Ala Thr Leu Ala Gly Asn Phe Arg Met
             190                 195                 200 cct gtg ctt cgc gag tac ctg atg tct gga ggc atc tgc cct gtc aac     857
Pro Val Leu Arg Glu Tyr Leu Met Ser Gly Gly Ile Cys Pro Val Asn
         205                 210                 215 cga gac acc ata gac tac ttg ctc tcc aag aat ggg agt ggc aat gct     905
Arg Asp Thr Ile Asp Tyr Leu Leu Ser Lys Asn Gly Ser Gly Asn Ala
     220                 225                 230 atc atc atc gtg gtg gga ggt gca gct gag tcc ctg agc tcc atg cct     953
Ile Ile Ile Val Val Gly Gly Ala Ala Glu Ser Leu Ser Ser Met Pro
 235                 240                 245
```

```
ggc aag aac gca gtc acc ctg aag aac cgc aaa ggc ttt gtg aag ctg      1001
Gly Lys Asn Ala Val Thr Leu Lys Asn Arg Lys Gly Phe Val Lys Leu
250                 255                 260                 265 gcc ctg cgc cat gga gct gat ctg gtt ccc act tat tcc ttt gga gag      1049
Ala Leu Arg His Gly Ala Asp Leu Val Pro Thr Tyr Ser Phe Gly Glu
                270                 275                 280 aat gag gta tac aag cag gtg atc ttt gag gag ggt tcc tgg ggc cga      1097
Asn Glu Val Tyr Lys Gln Val Ile Phe Glu Glu Gly Ser Trp Gly Arg
            285                 290                 295 tgg gtc cag aag aag ttc cag aag tat att ggt ttc gcc ccc tgc atc      1145
Trp Val Gln Lys Lys Phe Gln Lys Tyr Ile Gly Phe Ala Pro Cys Ile
        300                 305                 310 ttc cat ggc cga ggc ctc ttc tcc tct gac acc tgg ggg ctg gtg ccc      1193
Phe His Gly Arg Gly Leu Phe Ser Ser Asp Thr Trp Gly Leu Val Pro
    315                 320                 325 tac tcc aag ccc atc acc acc gtc gtg ggg gag ccc atc act gtc ccc      1241
Tyr Ser Lys Pro Ile Thr Thr Val Val Gly Glu Pro Ile Thr Val Pro
330                 335                 340                 345 aag ctg gag cac ccg acc cag aaa gac atc gac ctg tac cat gcc atg      1289
Lys Leu Glu His Pro Thr Gln Lys Asp Ile Asp Leu Tyr His Ala Met
                350                 355                 360 tac atg gag gcc ctg gtg aag ctc ttt gac aat cac aag acc aaa ttt      1337
Tyr Met Glu Ala Leu Val Lys Leu Phe Asp Asn His Lys Thr Lys Phe
            365                 370                 375 ggc ctt cca gag act gag gtg ctg gag gtg aac tga cccagccctc          1383
Gly Leu Pro Glu Thr Glu Val Leu Glu Val Asn
        380                 385 gcgtgccagc tcctgggagg gacgactgca gatccttttc taccgagttc ttgagtgcat   1443
tttgttctgt aaatttggaa gcgtcatggg tgtctgtggg ttatttaaaa gaaattataa   1503
tgtgttaaac cattgcaatg ttagatgttt ttttaagaag ggaagagtca gtattttaag   1563
ctcacttcta gtgtgtcctg ctcaaggtgg aggctgatat ttatgggcct tggtggtttc   1623
ttacccaccc cttctagcgt tccccagacg acagacactt ggccctggct agctgggcaa   1683
gggcagtcct tagtgactcc agggattctt gagaggcaga ggccatgtcc cacccgtggc   1743
tgcaggtcgg gttcctcgta ccaaggggag gctgagggca cagctggccc cacttgggga   1803
gggtagataa catctggact gcccggcttg ggtctctgct cctcacccta gccctcttct   1863
ccaatctgag cctaccctgg cctcctgtct cctggctagg gacacggctg tcccacaggt   1923
gccgtcttgg gttatctcgc tgctgttggc tggtttcact ctggaggttg gcaccatgga   1983
cacagctcag cgttgctctg gcgcatatcc tcctgagcca caccccaagt ctggtgtgag   2043
gaagggcttc tcttctcttc acagaggtgc ctggcttcct gtgcagcaca ctgggtccag   2103
gacaggaggc cccccccccca aaccaagcct cacgtgtgtg cctttatgag gcgttgggag   2163
aaagctaccc tcctgtgtat tctgtttttct ccatgagatt gttgtgccat gtcacacttt   2223
tgtatattcc tagactaata aatggaaaca agaacagcc                          2262
```

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
actctggagg ttggcaccat                                                20

<210> SEQ ID NO 13
<211> LENGTH: 19
<212> TYPE: DNA
<213> ORGANISM: Artificial Sequence
<220> FEATURE:
<223> OTHER INFORMATION: PCR Primer

<400> SEQUENCE: 13
gggtgtggct caggaggat                                                  19

<210> SEQ ID NO 14
<211> LENGTH: 18
<212> TYPE: DNA
<213> ORGANISM: Artificial Sequence
<220> FEATURE:
<223> OTHER INFORMATION: PCR Probe

<400> SEQUENCE: 14
cagcgttgct ctggcgca                                                   18

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                                 20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat                                                 20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                         27

<210> SEQ ID NO 18
<211> LENGTH: 42823
<212> TYPE: DNA
<213> ORGANISM: H. sapiens
<220> FEATURE:

<400> SEQUENCE: 18
gcagcagaag tgttaaagtt taagtgaaag ttttaaaaag gggtatgtgt ggttgtaaag      60
aaggcttctt ggaggaagat gcatcaagac aggacagatg gacagggtgt gaaaaagggg     120
gagcttgggg aagggcttga gctcaagagc acagtgtggg cagggaccca gaggtggaaa     180
agcacgttca gggcagggc aagtgacctg atgggcctag ggagctggac ccacattaga      240
gcatggcggt gggagaggag tggaggcggc tggagagagt ggcaggagca ggatgatgtg     300

```
aggccttgaa tgccaagtta aggagctggg gcctcatcct aagaactatg gggagccacg    360
agaaacaatg gttgggttct gtgttctgaa gctcattctg ggaatctgga gacaggggac    420
cagtgaagag gatagtacag ctgtctatgc aaggtggcat ggcccaaggc agaagagaga    480
aggagagaac tgtttcctgg ttgttgggca tagaggtatc agtgtgaatg ttttgtatg     540 tgtccatgag cacaagtaat ctttctcaga gagtcagcct aaaaaaaaaa aaaacccaa     600 ccctattcag tttcatgacc cagcataccc agcagcctgg gggaggccaa agttaccaaa    660
gaaagaggct gagagacatt cagttaaagc ctgactttat agttcttcct catcaacacc    720
atcctgcaaa ttcacattca tctacaggct ttcagggtgt tttaatccca gttatctcac    780
ccaaaatatt tgcttttccg cctttctttg tgtttcctgt atgcctcatg tcagcatcct    840
tgttcaggtc acttacttaa aaaaaaaaaa aaatccataa ggccgggctg aggtggagcc    900
tggagtgacc aggaaaccac tctagaatga actcctacct gaggcagctc ctcctcccta    960
gcagagccca cactggcctg ctgatcacct ccctgctcag gactctgctg ataccataga   1020
cctagtccta ggccagtttg ggaatctaga gaggccattg aaaagaaaac tgatatatgg   1080
ataccacccc tcctcggtga ctcaatcgta gctcctgaca actcagggtt ttgttttttt   1140
gtttgtttgt ttttctctt gagggttaca gagcatcatt tatagaatgc agtttataca    1200
actgacctca gaatatggcc aggattttgc agctattata gagcatggtc tctggagcca   1260
gaccatctca gcttaaatcc tggctctgcc acttcctaag ctgtgtgacc ttgggcaatt   1320
ttttttaacc tctttgtgtc tcaatttctc catctgaaaa atggactcat atagtatcta   1380
ctccaaaggg ttgttgtgag gcttaactaa atccacccat gtaaggaacc tagaatagta   1440
actggcagac agtaaatact cactgaagtt taacacctgt tatattgcct gttatagttc   1500
atgaaaactg ttgcttctcc ttttggaaaa atcaggatgg cactagccca cctccagtct   1560
cccaacgctt ctccagctga acagcatttc ctagagatta cagattctgt aatctgcagg   1620
ttctctgaga tgcagttgga acaatttaat acagcagagc agtcccatgc tccactgtag   1680
tctcactgca aaacagttca gcagcggttc tcaaaatgtg ggcttcaaac tagcagtatc   1740
agcatgtcct gggaacttgt tagaaatgca cattctcagc ctcactccag aacctactga   1800
atcagaaact ctggggggtgg aacccagaaa gctatatttt aaccagccct ctgctaatgt   1860
ttgaaaactg ccacagcata ttatagcaca gtggtttatt taggtagata tggcgcagtt   1920
cattgcccac tccttctcca caaagtgttc ctgattcccc cagaaccctc ttttactaac   1980
agctctaact tcctccctgt attactgttg tccatgctca aaagtgctca atcctccctg   2040
gattacaggt tacctgagag cagtgttggg tcttacacat ctctgcactg ggcagcccag   2100
gggctgccac agggaccttt gcttaggaaa gacatgctga gtcaagcgtg caacatttcc   2160
agtttcctct gactaaggct actattactg agcctctgct ccttccagga cccttgctca   2220
tactgcattt tcctttgtga attgtggtca tctcctatgc taagatgcct ggttctttgt   2280
catttctagt atcctccagt tccactgcct tctcaggcat tttactcttc tccctcccctt  2340 tatgtttgtt caaagccctt tggagaaggt gtcagagctc caggcaaacc tgtcacccta   2400
atccttattt tcaatcataa tacttctact ggtaacaatt tgtcaagtac tatatgccag   2460
gccctgtact gggcattta cattcattca ttcattcact tagagacagg gtgtctctct    2520
gctgcccagg ctgcagcgca gtgacacgat catagctcac tgcggcctct aactcctgga   2580
ctcaagcaat cctcccctcc ccctaccttg gcctcctacg tagctgggac tacagacaca   2640
tgccaccatg cctaggtaat tttttttttt tgggtagaga tggggtctgt ctgtgttgcc   2700
```

```
caggctggtc ttcaactcct gggctcaaat gatcctcatg cctcagcatc ccaaagtact    2760
gagattacag gcatgagcca ttgtgcccat atggcacttt acatttatta ttttagtctt    2820
tacaacaacc ctaggaggaa gatacctatt cccatttgga tggagcacag ggaaactgag    2880
gctcaaacac agtaagcaac attaacatgt ggcaaggtgg gggcttattc agtctggggc    2940
caagtcaggg tctgggtgga tggaccagga aagggcctt gtctaggcat atgtattcat     3000
ataaaaatga tccaccaaca aacctgtcca gtgcccttgc tcaggaagat gggtctgacc    3060
aggtgccagc ccaccagggt gcctttccac agtgtgcagg gggcatccac ctgaatgccc    3120
gtcttcagtg catcccctgg ccctgcactt gctattctgt gcagcaggag tttcaaactg    3180
tgttccacag agccctggag atagggtgtg tgggctgggc aagtgagaga caaaccctga    3240
ggaactgtgg gaccacccca gcagcctgtc atccctgtca cttcttgggc tctcaaggtt    3300
gtatttgaag aaatgatttc agctgggcgc ggtggctcac gcctgtaatc ccagcgcttt    3360
gggaggttga gatgggcgga tcacgaggtc aggagcttga ccatcttg gctaacatgg      3420 caaaacctcg tctctaaaaa tacaaaaaaa aaattagctg gatgtggtgg cgggcgcctg    3480
tagtcccagc tacttgggag gctgaggcag gagaatggcg tgaacccggg aggtggagct    3540
tgtagtgagc cgagattgtg ccactgcact ccagcctggg cgacagaacg agactccgtc    3600
tcaaaaaaaa aaaaagaaa aagaaaaaa agaaatggtt tcactgcttt taaaaagcta      3660
gaaactactg ctgaataata attgtcattt taggtgtctg tttcttcccc cagaatgccc    3720
ctaaggagca agaactgtac ccacagcacc cagcacaagg atgggggtc tcaggaaagg     3780 tcggccagat agaagggcag atgagaaatg aatgtactgg gagctctctg tgtaatatcc    3840
cctcccccac cctcacccca cccccaatt ctgcaggga agaggccttg agagagttga      3900
gtaagaaata agcaggcaga atgatgcaag gggagctgtc tgtacacatt gcaacagaac    3960
tttctaaaac aagcctgggg ctgctcccaa gggtctcagt cctgccctat tcctctactg    4020
tcatccagac ctgtcacaca agatagggcc aaaggccatt accaagctct gctaaggcct    4080
gaccttagag ctgggaggtc tgtgctcttg ggttctggtt tgaaacccgg agccatcttc    4140
aatcaccccc ttccttcctt tcagccctac atccatgcca tcaaatccta gagactctaa    4200
agcttcagca tctctcaaaa tcaccctcgc ttctcttttg ccttgccacc ccttcagttc    4260
aggctctgtc gtcattatct ctctccttcc tctcatctgc ctccctccct tccatccaat    4320
atcacccagg tccctgtggg ttgtctgtgc cccttcagca aaggccacag cttccatgtg    4380
gcagccctct ccgctcagcc cccattgcac ctgcagtgtc cttctcttag tccttcaggc    4440
cagatcccct gtgaggtgac tagtcctggg ctactgcacc atcccttgag ttttctctat    4500
agcctgctta catctttgca aacagtcttt gtattaaact gtcctcaaat tacccagttt    4560
gggtgggctg tttcccatag ggacactgac taatataagg tagaggtagt taggaagggt    4620
gccatggaga tgacagttaa agatgttctt gcctggacaa tgatctttct aaagcataaa    4680
actcctgcta aaaacctcta tggctcccca ttgccctgag aataaagtcc agactctgta    4740
gcctgccacc caagactata taccatcagg cccctgacca caaagcagca gcagcatgtg    4800
gggaagccac caggaagagg gagagtaggg ggcttggacg tgggaggcaa agacttccaa    4860
gaggagtgca gccatgccac acagctgctc tggctggcaa attcctgtga gtaaggaggc    4920
gggtgagttt ccaggctaga gggccatgcc aggctgcctc tgcttgccag aaccctgccc    4980
gcccactctc caagtgagtt gagcactgaa aggagtttaa ccccaatggg ccctagcctt    5040
```

```
gtggcatgag aactggttac atcccaaccc catctggtaa gctattggat tccctgagct    5100
ttcattttgc caactgcaaa atgggactaa cctcccaggg ctgtggaggc gatggatggg    5160
aatttgcttt cgtccagtag ttctgctgtt acaggtgctc cctctcccag ccttgggagg    5220
caggaaaagc gtacaggttt gaggctctgg aagacttggt gtgaatctca gctttactac    5280
ttactccttg tgtgatccag gacaagtcac tttacttccc tgcacccccat gtgcaaagcg    5340 gtggggggtga tcacccccttg tgtggtggct gtgaggactg ggcaagctca cacaagccag    5400
ggcctagcac agagcaggga gcttgataca cgtttgtttc tgtctttcta cctgtgcctc    5460
tcttagggca agtgtcctct ctgccttata ggctggccac ttaccctcct catgtgtgca    5520
atggaggagc taagactgct atcactgaag catatctcag aggtgcatgc gtcaaacctc    5580
tcacaagcta caaagctgca cgtgtaatcc ccaatggctg tacaacactg gtgattgaag    5640
tgggtggagg atgagccatc cttgtggatg cctctctgct cacacccctc ctttggtcca    5700
tcccccaaca ggatgaagtc caagcttctt ggtgggacca caaagcccac cctggtcaag    5760
cccttcttgg aggcatgact tgaccggtct ctgattttcc caatatacac atgggttgag    5820
agatgatgaa ggaaaggtaa ccaggtccta gaacacattc tcaagctgtt ctgctcacac    5880
acctgcagga aggtcagggc tggtcattat aggaggctag gaatgtcaag aagcatggga    5940
gggggccagg agaagtcaga gtctggtgta agtccccctt gcccaaactc acacagggga    6000
aaacagtccc aggacacagg aagctgccat gaaacttcct ttccaggcta ctctaagttt    6060
gggtctggtt ttccttccaa atccaatttg gaccaagctg tttaagcagt acccatgggc    6120
atggcggctg gaggccaagg ggaaggagtg ttctagaagt tgggatgcca ggggctgctt    6180
gctctgtgag gtggcacaga agtaagcaat tgtgcctctc agcccttgga ctcacctctg    6240
cgtcctctca cagatgttcc cacacaggaa gggcccaagc tggggaccag attttatggc    6300
cctattcccc aagcacccac ctccaccccca acaacccagc ttatcttcct ttttttttt    6360 ttttttttgag tcttgctctc tcgcccaggc taccaggctg gagtgcagtg gcacaatctc    6420
ggctcactgc aagctccatc tcctgggttc acgccattct cttgcctcag cctcccgagt    6480
agctgggact acaggcacct gccaacacgc ctggctaatt tttgtatttt tagcagagag    6540
gaggtttcac cgtgttagcc aggatggtct cgatctactg acctcgtgat ccacccgcct    6600
cggcctcccg aagtgctggg attacaggcg taagccaccg cgctgggccc cagtttatct    6660
ttctaaccca ccaatccaat caaggtgcat ctctgctcac accccctcctt tggtccatcc    6720 ccccacagga tgaagtccaa gcttcctggc aggacccacg aggccgttca gatctgggcc    6780
ctgtcaacct ctccagcctc atttcctacc cctcttctgc ctgtatcttt ctttcagcca    6840
caccagggtg ctcacagggt tcctacctcc aggcctttgt ccatgctgta ccctctgcct    6900 gacaccttc cccttttcccc ctgcctcaca gaatcagact tctcatctta ggtctgcagc    6960
aatatcactt cttcttgacc ttcccaattt accattccct ctacttcctc tatgactcta    7020
ctatactttt tcagggggca atccaccttg gactaagcgt ctatgccgag ctaggcccac    7080
actgggacat agagtgatga ggttcctgcc cttgggaaac gcctggctcc gtggagaggc    7140
aggcagacag tgacagcaca gggggaaagg ccaaacttgg catagccttc catgttaccc    7200
tgtgccacag gctggctgtc ttgggatcat tggctttagg acaccatctc tcgattgggt    7260
ctcctcaaag ccaaggacta agtccgatta ctctctgtgt cctaaccaag gccgggccca    7320
gagaaggtgc atagcaaaaa tgtgctgaag tagatgaact tgggatctga atgtttcaaa    7380
taggccttgg taaccccaaa tcttgccatt taagacaatg atctcttaca ttacagcaca    7440
```

-continued

```
gtgataacac tcttttacat gctgtgattt cacttcatcc tcaaatactc aagtgaagtc   7500
agcaaaacag aaactgtcac ctccatttca taatgcagaa aaggaaacct agacaagata   7560
gcgatactga cttgcccagg gtgagtgggt gggccatgag ttccagccca ggcctcctcc   7620
acaggagacc cttctggagc aggcacgagc cacagactga cctgggatct tccaggccag   7680
caggagtctt gcctccaaga gcaccctctc tgaggagagg atgccaggat ttactggcac   7740
cttcagtatc ctcctggctt cactcctctt tgcccaaaaa caaaccacac ctgtttctac   7800
ctcccagcct ttgcacttac cagtccccat gtctccccc atcccccaca tgtggcatgc    7860
cactagccta ccctcagttt cctaaaaggc actaagatct ttccagcctc atggcctcac   7920
cacatgctgg gagctctgcc tggaatgctt ttctttctac tcttggccaa ttcgggcctt   7980
ggggcccagt aacacggttg agagatttac tcctgtggcc ttgagagggc tgaacaaatg   8040
gaagcatctc taggttgcac cagaggcatc tattacctgc tgccctgtgc ctgtaacttc   8100
tgtcattctc ctctccccct gtgagaacat gataaagacc acaaaggcag ggaattcctc   8160
tcctcttatg ctgtgacccc acagctatct cgctccagct atgcctaaga aatctgtctt   8220
atcactgaca tgcttgttgt ccccactcgt tccctgagcc tccatccaac aagtcgctcc   8280
accacatgct ggtggatctc gcttcctatg ctcttcccta gatcaggcct tccctccatt   8340
ccctctacca ctgccgtgcc ttgaggctca tcctctctca catggatccc ccgcccctac   8400
agcctcccca ctgccctcct gacctacagc ctctcctgtc catttcccat accatggcta   8460
aggacactta aaacccacct gaccagccat ttccctacta aagctctccc aagacccggc   8520 tccccccaa tatctcaaga gtggcactcc caaacctctc tcagttcaag cacccgcgcc    8580
tctcacttca gcctcatttt ccacagttgc ctgggctcca gccactccag ggcccccagc   8640
cctgccccaa acatgctggc ttttctaaca ctttatgcct atctttctgc tttgccctca   8700
caccttccat ctgcaaaatt cctattcatt aatgggcaaa ccattctgga atgctttcta   8760
tgtgccagac actacctagg ctcttttat accttatctc atttacttct caaagtacct    8820
cacaaaaata ataattatta ttcccatttt acagatatgg aaactgaggc tcaagagagg   8880
cagggcaaga actggactcc tagtctatct gattccaaac ctgctgtgca ccaacctctc   8940
tgggaagtgc accagcgccc ccactccccc agcccagggc agagtcttct ctactctgtg   9000
gttccatagc cccctggttt ctcgcttgtc ccggccgttg tcaccagtga ctgtgtgcgg   9060
ctgtctctgc tgcccccag cgtgagcatc ccaagggcag aacctgggct gatctggctg    9120
ggtccccagc acccagcagg gtataggtgc tctgtgaggt ttcttaataa agagatggaa   9180
agccagaagc agtttgggtg gttgagatac ccagccctaa cctaactaat cctgatacca   9240
gtgaccaaaa gcgggacctt cgcatctttg ctgccaaaag acagcccctc ctaaagagta   9300
aaggcccgac cccctgcacg ccctctgcct gcaccgcacg tgcttggttt tccccgcccg   9360
ggtactggcc gccgggccgt accaatctcc gcggggagc gccggggtc ggactgaggg     9420 agcgagggga ataaccgggc gcgccccttg aagcagggc tcagagctgc tctcctctca    9480
cgcattcccc ggatccgcgc ggagcaggct gctggccagc cccgggcccg cgccaagcag   9540
agcctcaggt gcggttcccc cacaagcaag tggcgcgggc ggcggcttag aacgccccgc   9600
cccgcccgcc gcgtcggcgc ctgccccgtt gtgaggtgat aaagtgttgc gctccgggac   9660
gccagcgccg cggctgccgc ctctgctggg gtctaggctg tttctctcgc gccaccactg   9720
gccgccggcc gcagctccag gtgtcctagc cgcccagcct cgacgccgtc ccgggacccc   9780
```

```
tgtgctctgc gcgaagccct ggccccgggg gccggggcat gggccagggg cgcggggtga   9840
agcggcttcc cgcggggccg tgactgggcg ggcttcagcc atgaagaccc tcatagccgc   9900
ctactccggg gtcctgcgcg gcgagcgtca ggccgaggct gaccggagcc agcgctctca   9960
cggaggacct gcgctgtcgc gcgaggggtc tgggagatgg ggtgagtgcc acggcgcagg  10020
ggttatggac ctgcgagaag attttctgga aagggccctg tggcaggctg gtgggtactg  10080
atgagtccac gttcattctc cactgtggca ctcatcaatt tttacgacct ctgttacatc  10140
gctttccacc cgccccccag cttgtttccc tcatccgtga ggtgggagcg gtaccaccca  10200
ccattcttag ttattaggga tattcgagaa ctcctcccca gccccactg cggctggtga  10260 cccctggcac ttccctcccc tctcccttca ccaggtagag cgagctttgg cagtgataga  10320
ctggatgggc aggatggtat gggttttgcc gtctcctgag acagccacca gacggggaac  10380
atgcccgact ggaacaggtg tgtctgccct gtcctctgtc ccacatccat cctctcgccc  10440
aggctctgga gcccacatag cagcaactct tgagcctggc atgcttagaa ggcagcggag  10500
aggaccctgc atgtcctcca aggtagaact gaggtcctca gtgaatcgcg cagagttgaa  10560
atcaaccccc gccccgcacc ccccgcagct tttcccaagc gaggaatagc aactcttcca  10620
accccaccct cccttaccta gagctggaga aactgaagtg ggaggaagca tgcctaagtt  10680
ttccttagct gatgccttga cccctggatt caagtacaaa tccggtagac cctgggaagt  10740
catcacagct gtcctggtct gcgtgtgtgt cttgcatgaa gcccctctcc ctctttctaa  10800
gtctgtattc tgtttgctga gcctctctga catggatttt tctttagtaa ctaacggtcg  10860
cctacaccgc ccacctttgt tacaaaaata aagcttgcta attatggaat ttttgaaaat  10920
atagacaaat gaaaaaaatt tctggtaaat cgactatcca aagataccttcctattagca  10980 ttttagtata tctcttgatc attttcttta tacacattgc atagatacaa ttgaggacat  11040
gctgtagata tagttatgaa tcttgttttc tcccccttaa tgtaacatcg aggtttccct  11100
tctgttaatc agaatcactt acaatgtcct agtggttgca ataacccacc ctgcagctgt  11160
accacacttt aactgtgacc taggcattgg cattgcttct tgtgtgatta tcgctgtggt  11220
tatctgcccc tcttggtgtg ggtgctgctc gtagcccttg aagaggaacc cagctgctgc  11280
cctgtctcgg gggcgagcag cttgagctgc cccatgtatc cagccagtag cctctgacag  11340
ccccttctct cacttgagtc ctttttctgtt ccctgtgtcc tttgatgtcc ttagggacat  11400
caatggatga atggacttgc ccttgttcat gctgttaaaa atgttttttgc actgggcagt  11460 gggatagggga tgttctctgt ggtagtgctt cctggagacc ccattccgtc ggctctgcca  11520
tccacaggct gggagctgtg tcttccagga ggcagtgacc ctggctgtca tgttttttgac  11580 ttagagtttg ttccttagga gaacttgtac tctagcgaat ggttttaacc aagccactta  11640
atatcatgtc aggaacattt ccccatgttg ttatcagatc ttgaaaactt ttttttttt   11700 aaactgggtg caaggattta catcatggaa tgtaggaagg gctggtatga aatgcaaacc  11760
agtcagttca gctttctggg atctactttg gtgaaagatt gggtggagta ggggagggca  11820
ctgaagcaca ttttgttatc tgggcatctc cattagacct gccttctaga tccttggtcc  11880
ttgaagatac tccccagtgg cctagtttgc ctctgtgggt aaggtccacc tgttgtgagc  11940
tggtgaacag cccgtcagtg acagtattca agtagagacc atggattctg tgaagggaag  12000
tcctgtgacg ggtgagagat tgaaatagat accttggcat ctggtttctt ggccaaaaaa  12060
aaaggccagc tgtgggagta tgggtaggtg ggtgcatgct gggggaagcg ggagtctgtg  12120
ttgatatttc ctaatccttg gagggctgtc ctgtgccaga cgtggagttt gcagagttca  12180
```

```
tcaggacagg agggatatat atcctattct ttatccttgc cttttggattg ggggctcttc   12240 gttcagaaga gccctctgac acctgcctgt gtcctcaggg ttcagcacag gacctagcat   12300
gagatgttgg tggtcccagt aaaattttga gctgatttgt tgtgtgcggc tccaaagagt   12360
gaggccagga ataggagtgg gatgatgggt gcaagttttg atgtagcaga ggagtccttt   12420
ctgacagctg ttgaggactg caacaggctg gggtgggtga ggatggagtt ccacatcact   12480
gtggatctgc ttgaaaactaa gtggctagat tgttgggggt aactgggaac tgagggttga   12540
cagtcaccta acctagtcct aagtcagaat gagaacatta ctctcatgct tccctctcca   12600
attccgtgtg gcttccccccc tcacctacat cacttcccca gctgaataga ggccactttg   12660
gggctgcgtc accaagggct catctaggct gagaaaggag ggccaagagt aatgttgtat   12720
taacaggctc agtgactcaa tggtcagtgt tgaaatcctg ccccacctcc accctcctgc   12780
cctcaaattc aacagcaagt acttgagttg taaaaattag tgctggatcg ggcccaaccc   12840
tcatgttaca gatgggatca ctggagtctc cagaaagaag ggactttccc agggttatca   12900
aagccaggct agaactcaga tccatctccc agtctgtggc ctgactcctt aagccaagag   12960
aagggttgca aggccgtgaa gggctgagtg cagggctctg tgcattgtag gtgctcagtg   13020
gtttgctgaa tgagtgaagg ttgtctccat ggtgcgggtg gcagctcatc ccttctcaaa   13080 cttttttgagg aagctcccca agcctgccct agtggattag agcactaaga tcccccagag   13140 cttttggctgc caggtgaatg ccagttgccc cctacccaca ctcagtcaca cttcagactt   13200
tccaaactct tcctcctggc ctatgaagta agccccaggt gaacagcctc cactgccatc   13260
acgacttcct ctcctagtat gtcacccacc atgctgcaga cgcatggtgg tcttcctgtt   13320
cctgcagcat tactcccaat tcagtcttac ctcagcgcct ttgcatatgc tgcctgtctg   13380
cccaggtctt cgcatggctg gctttacaac agtcaatctc ctctcagagg tcttccctgg   13440
ccaccctatc tagagagcca cttccaatct agagagccac ttccaatcac cacatcttct   13500 tttatttta tagcctttat cactacctaa attttcatgc gtgcttatct gtttaagcaa   13560
ttgtctcccc agtaagaata tcagtccctt tgccggccgc gtgccatggc tttcgcctgt   13620
aatcccagca ctttgggagg ccaaagtggg aggatcactt gaggtcagga gttcgagacc   13680
agcctggctg acatggtaaa accctgtct ctactaaaaa taaaaaaatt tagccaggtg   13740
tggtggtgtg tgcctgtaat cccagctact gggaggctg aggcaggata gtcgcttgaa   13800
cccaggagga ggaggttaca gtgagccaag gttgtgctac tgcactccag cgtgggtaac   13860
agagcgagac tccatctcaa aacaaaacaa aaagaacaaa cagaaaaaga atatgagtcc   13920
cttgaaaaca ggaaccttgt ctgtcttct cagtgctgtg acatctagca cagtgcctgg   13980
cactggtaat aggtacttag taagtatctg ttaaacgaag gaatcattag tgggactgcc   14040
ccattcctct tggaggaagc cctgcttta gcttcagtgt gattcctcga gccttccttg   14100
ggcctcctct gtccctgtaa ccacctgtgc tagggactgg gtgctggggt tgtagctgtt   14160
ccctgccctg gaggtaccca cagtctggca aggagctggc tccaaggctg agtggcaagt   14220
gggcagagcc agtctcaatg gtcacccta ctgcttccca gggcttatta gaagcccgag   14280 agctgggggtt ccaggcctga catttttctg ggatgtggct gggggcttca cttcctctct   14340
ggggatctca ctccttctat ctggaaaata gggtcagaat tctcagattc tcaaggatgg   14400
agggtttgag ttaacctgag tgtgagtgtt tgtgaacttg tgacattcat gttagtcctt   14460
gtcatttgtc ctgtgttaca cattcagcag gcccccaaca ctgtagagag tggcagaccc   14520
```

```
tgctctaggg catccaggaa ggcttcactg aggaagggac ttggggtgtg gaccccttcat    14580 tttattgatt gagcaccttc tgtgtgtcag ctgcagtccc tgcgtttgag gaagtgagac    14640 caggggatg  tacacaagat gactgtgcag agtgatctga gcaatgacag gaaagactgc    14700
caagaggtga gaccggggag cttgatcacc ctgaggtcag ggaagtcttc ctggaagagg    14760
tgacattcag tccggatctg gaaagatgaa tagacatcag caagacaggc aagaacattc    14820
aggtacagga aatagcataa atagaggcat gagatttgga tgggagaggc agactgactg    14880
cagggcctct gagtgaccaa ctgaggctga ggtcttggtg tactgagagc cagagacaag    14940
agagacagag aggatgctgg atccaggcct gtggtggctc acctgtgtct gcagcaggag    15000
gaagacttga gagctcatgg gaaaggagcc tggtgcagtt agtttattgg cctccagcac    15060
tttgagggcc tcctggtatg gagctgctgg ctgatttgag ggcctcatgg gcagggccca    15120
ggggtaggag tcaggcctgg gctctgtcca gctcctgctt ggccaccgaa ctgctccgca    15180
gcctcagcaa gccactaccc ttccttaccc tcagtctcct catctatgaa atgagcaaaa    15240
gtgtcataag aacctgtgca gattatggtg cagatgcaga caggctacac cctgtgaacc    15300
ttttgggtaa atcaatagaa atgggaaaca caaactcctt ttcttattag agcagaatta    15360
gccattctaa gccctgcctc tgcttcccat gtgaccttgg gtataacact gcctcttagg    15420
gcctcagcct tctcatctgc acagtgagga ggactggttg agatgacccc cttggcttcc    15480
ttacatccct gctggagaaa tgcgattcca ttcttgtccc taactgctgt gggactcttg    15540
aggtcagcca cctcctcatt cttgtcctca gcttctcctt gtgaaaatgg tgcactcatc    15600
cacttggggc caaggtaagt gccccagaag aacctgtctc cccatgcttg cccatatatt    15660
gtgatgggga cgtatttttgg agattccttg gtgacctact cgcaagctag tagtgttgcc    15720
atggcagccc cttccactgc agtagctact ttttgaatgt gcttggtcac agtgggtggg    15780
gtgggggaag tgggccccctg gggtcctcag caatcatgtc cagggtcctg gatgtagatc    15840
catgttcggt atcaggaaca tggcattcta agagtctcac ttccttggcc ttacctcttg    15900
gaactttgtg aaagttctac ttgatgaaaa cggaatacac aaaaacccag gtgtatggag    15960
tagcccgagg atgggcttat attccctttc gggagatctt ctgtggataa aaattcattt    16020
gtggattcta gcagagcaca ggtggcccaa gttagcagca ctcagatttc aacaaatcca    16080
ccccagcttc ctaatttagt gctaatgggg aaacctagag aggggaggaa gaggcttagc    16140 gccctgcag  gtctacagat gctcaggatg cctggctccc tgcagcaggc cctgaggact    16200
gacagtgcct gcagggtcct gatggcccac ttcccacctg gcacacctag catagctgtg    16260
tgctggctct ccagtagttt ggcttccccct ttgggccaga tgtcccagtg ggccctgctt    16320
taaggatacc tcatttgcaa aacagaaccg ttaaagcgaa ttgttaatct ttcagaaaa     16380 gaactcactg gcgttttggg accagttcta tagctagcta gctgccctag ggctcttagg    16440
caccagtgga gggagtgagc tctgactggc tgtcttctct gccttcaggg tagaggccag    16500
gactcctaga cctagcatcc cagtccttca tgcctccctg tttctctact tttccaacta    16560
gactcacagt ctctgtgctg cagtctgact aaactgcttg cagttaattc ctcaaacttg    16620
tcttctctct gtttcgggcc tttgcaatgc cttctgggat cctgcccctg taccttcctc    16680
ctggaaggca tccctaagaa cacccctcctg tgggggttgg ggcctcccct ggattcctag    16740
tcctgactga tcctttatgt ataattgttc gcagctttgt ctcccagcca tatcttgggt    16800
gggcagccca ggagcagaac tcagcctcta gcagatgccc aagaagcaga ggagaagcag    16860
agtctagaag ctccccctcct ggtgtggagc ctggggtgta aagggtactt agaaagcact    16920
```

```
ggtatgaatg ttagtgtttg ggttccaccc ttctctctcc cttcctctgg ggccttccac   16980
cattgccccg acattaacca ccctccagct ggagaagacc tttccctcct gattccccag   17040
aaagctctgc ttgaccctcc atcatggcac aggtcagtca gctgtgggtg gactttttttc  17100 tatctttgtc taggccctgt ttattcatca cagtcctctc aagcattcag tcattcagca   17160
aacatcgatc gagcaccttc tctgcgcctg accctgtgct gagcaccagg gcccagatga   17220
atgagacatg gtccctgcaa atgcacacac atacctttc ccataatgag aaagggctga    17280
gtacaggggt gagatgggac aggcaggat gcggtcaatc caacccaggt ggaggagaag    17340
gaagactttc cagagaaaga gtcaacaggt tggtctctag caggccagtg ctcagtgcct   17400
ggtggatgcc tggtatgcat gtgctaaaag actgaccaaa ctagacttag aagcaataga   17460
actctacctg gaggcactgc agtgaagtcc ctccttcctg gagggaacga gtctctggct   17520
gagcacatgg tgaggcacca agtggagaca gcttcctgtg tgaggcttac gggagcccag   17580
ccctggcctg ggattctaat agcagtgggc atgaccctcc agagatggca gctttgccat   17640
gaccggcctc tcatcatcat gtgtgtggac tcccgctgaa aggtgtctgc ctggaggagc   17700
ctggaagaga gctcacctcc agccttgatg aagtggcatc tctttggcac ttggcctgac   17760
ttcctagacc tccctggggc tggaagagcc tgctaggggt caatatgtac tgaccctcac   17820
tctgctacct ctcctcataa tatacaacct gttactgtgc acctcttaaa aaactgtttg   17880
ctctctctgt ctccgtgcaa cttgtcctca gctctttggg ggtaacttgg gggtgacttt   17940
ctcactcacc tagacccagg gcagacatta ggtccagatg ggcccaggtg tggcatcctt   18000
ggggttgggg atgtgggcag ggtgaccccc acccccaccc ctgcctcaag gagcccaaga   18060
ggctgttcac acctctctta gctggcatct ttctggctct ctcacattga tgccagacat   18120
tctggccctt ttccctaagt tatttagatt ccttatgaca atcctggatt aaagctaagg   18180
aggacactga gtcccaggga cagggagtga tttgcaaggt tcattgcag gtaagaatca    18240 gagccagggt ttgaatccta agttagcctg tcgcctacgc ctctgttcct aggcagggca   18300
ggcattattt tacccatcaa acaggagagg acaccgaggc ttacttggta attaatcagc   18360
attcatagag atctttactt tttatgaagc tcttggctat acattatctc atttaattcc   18420
cacaacaatc tggtgaggta ggtattagcc ccactgtata gatgaggaag ctgaagcttg   18480
tataggaagt gactcatcca ggccacttcc tacgagttag aggccaggtt ctcctgactc   18540
tcggcccctg ttttcggcac tgactccagg ttggcatgtc ccctgccaga tgccagtatg   18600
gaggtgaggt gggtggagga cgcggtgtgg gctttcgaga ggcgtgagct gcccacagtc   18660
tctgtctacc agtgcttcgc catgtacgct cagggcctcc tctccatagg ccagggatcc   18720
tcctgcccct ctctctatct cattgcccca aattatttttt cttcatagct ctcgtcgctg  18780
cctgatgtta catcatacat taatacgtag gtgttttatc tctccctcag cagaagttaa   18840
gcatcctaac ttaactttag ccagtctgac ttgggcatcc aggcctatag ctgcctctga   18900
ggcaggacat catctgctgt gctcactgct gtttccccag ggctagtatt agcgcttagt   18960
accttgtatg tgctctatgc cttgggtctt agctctgtcc ccacccacct cacccaggaa   19020
gccacctttg actactcatt ccaacttctt tattctcagc ttctatttca ggcagtcact   19080 caccccctt tctgggttct tgagtatttg ggtctgcctc attagaactc cctgcaaggc    19140
tttgttccag cagtttcccc caaccacagt gcgcactttc ctcctgtttg acccctagat   19200
cttgtcttca gggccctggc gaagcctcat ggcctccttg gagcctcctc tgcgctacca   19260
```

```
tcactctgcg acctcttctt gtaacacaga cctgtggcca tgagcctctg gaaaaactct    19320
gcttgctcac tacatatact ccttcccact ctggagatgg gaggagcaat gccagtagcc    19380
accacttaat cacctaacaa atgccacatg tgccttaaac gttttaaaat ttaatgttcc    19440
tggctgggcg tggtggctca tgcctgtaat cgcagcactt tgggaggcct aggcgggcgg    19500
atcacgagat caggagatcg agaccatcct ggctaacatg gtgaaacccc atctctacca    19560
aaaatacaaa taattagccg ggcgttgtgg cgggtgcctg tagtcccagc tactcgggag    19620
gctgaggcag gagaatggag tgaacctggg aggcggaggt tgcagcgagt cgagatcgca    19680
ccactgcact ccagcctggg cgacagatcg gactccgtc tcaaaaaaaa aaaaaaaaa    19740 aaaatttaat gttccccaaa atcctgtgag gtgaggatta tcaccctcat cctatagata    19800
agaaaaccaa agctagagtt aggtgacttg cccgaggtca cagagccagg caagggcaga    19860
gctggcccag ggccctcttt ctcagattta gggggttggg gctcagacac tgctgccctc    19920
aggcatgtga gaggaagccc tgaaaacttg ggtttcatca gccccgaggt gtggccttcc    19980
tggtcacttt gatatcagat attgggcaaa gaggtgctca cagacaccct tcaacacccc    20040
agccctgggc tgggccctgg gtctgagaac tgcttgaaag cacatgggtt gcggggtgg    20100 aatccagtct cactagaaca tccacatgag actttgagca tgatatgggc agaggaggga    20160
gctctccttt gccaggatat gttcctgaag tccaggtgtg ggctggcgtg tttggtgggg    20220
ccagcgctca acagcgtagc attgtagaga tgatgaggga ctgggagcct gaatacctc    20280 tttaagtcct ggctcccaca ccctgacctc aagcaagtga ttttgcctct ttgggcttca    20340
cctcacctca gtttccttct ctgtgaaaca ggattgccag ttctcccctt gcctaccttc    20400
ccagagagtg ctgtgggacg gtgaagcccc acataggcgc aggagaaggg gattgctttc    20460
cgggtggtaa aagagctgct ctgggcctct ctggcagctc tactccctct gccttcccca    20520
aaggtaggag caaatgagct gtgtgtaaag caagtgctgc ctgggagcag ccatttgagt    20580
cttctgttgg gaatcttccc ctacagcctg tctcatctgc ccccataaaa cagagacatc    20640
tgtaggtagc agggttgtgt tccctttata ggtggagaaa cttgtaccta gggagggcaa    20700
aagaggctca tcccccatct ctggggtcag tcctcagtga tggggctggt tttgcctcct    20760
gccaggcagc ccagtctaac ttgggcatcc aggcctatag ctgcctctga ggctgctctg    20820
gatttgctta tggatttgct cagctatgca gtaaacctct atgagcccct cttaccacag    20880
atgaatcagg taccaagtcc tggcacccat gcgtcactgg cagtgggatg ccaagtaaa    20940 gtgacattgg tgctgtggga gtgtgcagag agagtgcaga tgtggtgagg gggcagatag    21000
gagcagggac ttggctggat gctgaggctc cctggtggcc ccacccagga gtcaggaaca    21060
gtcagactgg gtgtgaaggt ggtggcatgt ggtggcatct gattgcagca tcggcatccc    21120
caccagcttc tgctggactc ctcccagcca cagctgggc agaggaagta ctgacagcca    21180
ggtggcaagg actggcagtg tttggggt gcccaactga accctcactt cccatctgcc    21240
tgagcaacgg taccagaact actgcaagat ggtaagctct aggtcccaaa taccctgaca    21300
ggagtcctca ggagggtggg tgccagagat cacagacttc accctcctta cccccatttc    21360
atagatgggg aaactgaagc ccagagaggt gaggagactt agcatgggag ttggtggcag    21420
agctgggtct agaaacccaa gtcctgctgc cactctacct gctgtagaag atgcctgctc    21480
ctgacccacc cctctgaagg aaaacagatc attcatttct ccccttcccc ttccagctcc    21540
ccaccactgc cccctgcttt gttgtgggga cagagagaa ggaacttggg gacatgcaac    21600
atcggagcag atgcaggcct gaaggttggg cctgaattgg gttcagcttt gccagcatct    21660
```

```
ggctgagtga ccttgacccg gtatcaccat caaaataggg tgttggtgcc aaactcacag   21720
gagtccaagt gcctgtgcaa gggcatggag ggtctcccaa agctttatgg gcctcttgtg   21780 catcataccct ttcactcagc cctgcatgga gggaactccg ggggcctgaa gagtggccag   21840
agcacctcct tggggctggc ctgacagggc actggggatc cagatatgga tcagacccag   21900
gcctggcctt cgggcagctt ccagtgtgat ggagaatcag cttgtaatca gcagttagaa   21960
caaggccaga ggctgtggga accctgagga ggatgctctt ttgtttctcc attgtgcggg   22020
tctgacttta tcttcaaata ggttatttct gtgggtggca agatagcccc tggcaattcc   22080
aggcctgcat agaccttagt gtttatcatc ccagagaagg aaaggccttc tctttccaaa   22140
ggcttcctgg aagactgctg ccttatcacc atctctgggt tttgaaggat gtattgcttt   22200
atctcattat cagggaatca tcaggtaagc aaagcaggga agggcctctg cctagaatat   22260
ttctgaggtg gactggggcc tcccactggc ccggggttca gcatccatgg ccaggccagc   22320
tcccaggcca cggcctccat ggtcagccag gttgggattg cctgagaggg cctgggcctg   22380
agaaagcaga ggtgcagtcc tcccagcttc cctctccagg agcctcccaa ctctaacgcc   22440
cacggaagca cttgccattt ggtatttggg acttagagct caccaccttg cagcagtccc   22500
ggtacagttg cccaggcaga tgggaagtga gggttcactt ggtagactgc atttcccact   22560
tgttggcaga gcgagctgtg ggcggtagtt ggggctggat aaggcagggt gagaaccgaa   22620
ccagcagtgt gggaaaagcc tgagcctgca gacccacctt gctgcgggac ttgggagact   22680
cccgcaggcc ctcaatttcc agtctgtata acggggtgag ggttgaacaa gatggcgtgc   22740
gtttcctgcg ctatgacttt acctaatttt aagacaccta ataagcttag cagagagatt   22800
tggattaggc acgatgaaga attttttaggt cttctcagtt gtttcagttg gggatatgtc   22860
atcagtgaaa tttctatact cctcctccaa gctgcatggg ggctggccct ggcgtcaagg   22920
tagggagcta gataagttga ctcccagcat gcctcttccc tacgcacccc tcaaaccact   22980
ggcttcaggg gcctgtctgc aacgggaagc aagtcagcca cgagaaggca tgctttgcct   23040 tttttttcctg ccaaatagaa ggtggtgttc cccggtgctg tgtctcaccc cagcccctac   23100
ctgagtgttt ggactgaagc atttatagtg gtgtttctca gacttaatca cctggggatc   23160
ttgttaaaat gcagattttg attcagtaaa tccagtctgg agcccaaagt cctgcatttc   23220
taacccgctc ccaggtgatg ctgatgctgc tgttcccaga ccacgctttg agtaggaaag   23280
tgctagagta cattttgtct tctgtctagc cagggcatcc agcctgcctc agatggaaca   23340
ggaactcacc tgccacttaa ccagcctccg gtggccatgg ctcctgcttc acttcatcca   23400
gcatggctca ggaggcagag ccagctgctg gaagatgact tgtccagccc cagcccttgg   23460
atcaagggtt caagcctgtg cttggacttc acttccctcc cttatatact cacccagtcc   23520
tgtcccactt gtaggtgaag gtgaaaggtt atgagaccct caaggataag catgtgatga   23580
actcatctgg ccaggtccca ctgctgggca ggttgaccag gccctgagca tgaccctccg   23640
actgtgtcct gtgtacagag cctttgcact cagagctgct ctggggaaag gggaggtcct   23700
ctaagcaggg tcaggaatgc tgggtttcag tcctggctct gccgcctact gcctgggtag   23760
ccctgggcta gtcagtgcct gtctctggtc cccagtctcc ctggctgtcc aattaggcta   23820
tactggatga ccccagaggg ctctcaggct ctaagatggg ttgctgggca agtctggagg   23880
tgggaaagtc ctatgaaggt aggattttttg taaaggggc gaaggagcaa ttatgaggca   23940
gacctctgga atggctctat ggcccagcct ctttatttgc ttttgtgagt tcacatcctg   24000
```

```
ccgcctccac cccagttatg ccagtggtgt tattagatgc tactgaacac ccaatttgtg   24060
cactgaggat gtggcagtga accctgcaag cttgcctggg gtcacatagt gagtagaacc   24120
aaagtctgaa cctaggtttg actcttctgc taaactaagc cctttccctc tgatgcatca   24180
caccagggaa aggggccatc ttgaggccta gcatttcctt ccttcctcct aaaagtcaaa   24240
gcagttgtta actttcagct cataagggta gatatctttc taaactctgc tgtggctttg   24300 ttgcttttgca gattttgaag aaaagcaaag cttgagtgt aggcccctaa atccgtcttt    24360
ctccctgctc ccagcttgta ggctcagttg aaaggtcatg agaccctcaa ggacaagatt   24420
gtgactaact catctgtgct ctgggtcttt cacagagcag atggtatgaa ggaatattta   24480
atgggcacac agtaggtgct tggtgaagat gtgttgagca aagggcatgt agtgggggtt   24540
cagcaaagag gggtttgagg tggcccactt cttcagctgc cggaaggaat ggggtatggg   24600
tgaggaacct tcacccatgc tcttccccag tgctgtctcc tgcagtcacc aggcttcctg   24660
tccctactgc ccatcagctg ctggagtcca gggtgtcatc ctaggggcac caagccaatt   24720
aagtgggcac atctcgtcct aacttccagg cttggcactt gattgatagt gaacataatt   24780
acagccctca gtgtccttca ggctgcctga agctcactgg ctactgggcc ctttggggaa   24840
gcaaaggctc ccaccttact cctttctggg ccccacgctt tgggcactga gatgaggctg   24900
aacatttaca tctctctgaa agtggtagtg gtgtggggaa tcagtggtgt tgggggtggg   24960
ggcaagaggg ttcagctcct tggagaaggg gtattagtct gggacataca gaaggcagag   25020
cagggattgg ggatgctcaa agtacacttg gagaaaaaaa accattgcaa attggatgtt   25080
gaacctctgt ccttggcctc acagacagat agcaaaatta aatatttgta ctagattcag   25140
ataagggaca ggagtttgac tggggtggag gggatgggag agaactggca attatgagag   25200
acttcccaag gcctagccct tggactagcc tctttagata cttcatgtgg tctccaaaat   25260
gaccccgagt gcgataccat tcccattgtg tatctataga aaccagggca caggggagca   25320
tgcagacagc ccagagttac aaagccatga ggtggagggc taggatctga acccaggtct   25380
gtctgattct atagctgatg ctcttctcat atctagaagg gtacctgtgg gaggtgaggt   25440
ttgtactggg gaccccatga ctggagagaa gggtgacagt ggactgacat cttccctctg   25500
ctgtaggcac tggatccagc atcctctccg ccctccagga cctcttctct gtcacctggc   25560
tcaataggtc caaggtggaa aagcagctac aggtcatctc agtgctccag tgggtcctgt   25620
ccttccttgt actgggtaag ctgggcctta gagggagggc aggtgggcag gcagtgtcca   25680
cttccccaaa agaggtagag caggagccct gctctacagg ggtgagggaa taagagtaac   25740
tcttacacat gctgcccac agcacctttc cacatctatc tttttgggtcc cagatcaagt    25800 gctctacccc tcagcatgca tgaagattca gcaagattca gtgggaggtg gtgtgatagt   25860
tcccatttac agatgggaaa cctcaagtct tagagaagat aggtaacttg cccaaggtca   25920
cacagatttg aatccctgtc tacaggaccc ccaaagcctg tgcctttccc acaatgccac   25980
cctgcccacc aacagacatt ttccagcagg tatgttactt tgccttaagg tggtttggtg   26040
ccaggtttaa gtcctgaatc tcctgcagac aagctctgtg accttacaca ggttatttga   26100
gctctctgag tgttagtttc ctcatttttga gtgtgaggaa agtgcctgct tcacatggct   26160
tttttgagga ttgaagataa gaaatgagag cacctggcac agggcctggt catgatgggc   26220
ccccattaca tgggaatcat cgggaggtgc cctcagaccc cactcccagc ccacacccat   26280
cctcagctga gcacattccc caggtgcttc ccgaggcctg ctccctgcta tctctcagca   26340
cagcccacat cggtgctttg gttgctttt ctgcaggtct ggctagatac cctcactcct    26400
```

```
taggttgcca tccaggccag gggcaggaca acacgaatgt ctgaggggag ggaagaagcc   26460
tcttgttttt ccccagaccc ctgtgctctc agcatagcag gtagcttcct cagcacgtca   26520
aggcagatga acctgctcca gagcatcaca gagtgcattc cagtgcctgt gagccagtcc   26580
ctctgggcaa cccactcttc gggactgtat aggctggtag gggatcatca ggacttacca   26640
tgtcagtgct gagcagctgt ccttcaggca ggtgcatggg gcgctctgag actgagacca   26700
tgtttgcagg gccaagggat agaacttcac aggtgagaaa atgcaaattc acaaaggttc   26760
atcaactacc tgctactgtg aagctcatta aatggcagag ttgggatttt agcagaaact   26820
cagtgcattc cccagggagc ccacattcct ggaagcccag aattagtgaa ctggggctga   26880
aacagccagt cttcaccttt aggcccaaga acgggctttg agtgggggga tccatgaacc   26940
cttaaaatta gatgcaagat tatatatgag tatgtgcaca tttttctggg gagaagggcc   27000
atagctgtcc tcaaagtctt acagggacag gtagcctcaa gaagacaaac actggttgga   27060
agaactgagc aaactaaaca gtctccctca ggactcagac ccctaacatg gcttgcattt   27120
ggccacttac tagaatccta gagtagtgag cacagtgtga ccccttcttg ttaaaaaagg   27180
aagtggaggc ctggcgagga tggagcctta cttggggtca catgagaaga aagtactggg   27240
accaggacaa gaacccaggg actccagcct cccagacccc ctgcctagtc tgctacacca   27300
gctctctttg ttccctgttg cacccccaaag ctaccactat ccctgtctta atgggtctgg   27360
gcctggctgg tagggagctg agcagcttgt agaacaccag ctcacgcagc atgtgatggg   27420
gactggcccc aggctatagg ttaataattg atcagaccca accacagccc agaaaccggc   27480
ccagcatctt ctcaacaccc tcgcctggcc tcacctcgcc tcgcctcgca taggtgggaa   27540
cctggcctcg ttgacaggc agatctcctg agctactgct aattactgcc ctcagcagcc   27600
ccagccactc cttccctctg cctctcaaac ctgctggcag aagctcacct ggcaagcaaa   27660
gaccgtggtg gccctgttgg tctctccctg gaccagagat ttttcaccac tttgtgccat   27720
ggaaccctct gtcattttga tgaggcctat gcccttctc agtgttttag agtatttaat   27780
acaaggtgca ttggatttca aggaaaacta ctgataataa aatataaata tctatacatt   27840
aaaaaagctg attagacatg tagtaacagg tgcctttta ttacagtaaa taaaaagatc   27900
tagcagcaca tgtaataatt actatagttc ttaagtagtg atgagaagaa atgatttttt   27960
ttaagatatc tgcaactgct acaaagttat atgaaaatac ctttgttatt tatttgtgtc   28020
ataagtactg ctgataattc tgtgatttat tatattggta agtgaaggaa atgccacatt   28080
tccataagag ataagtgaaa atttagatgt catttgtttc cccatccaag tccatggata   28140
ttgtgtgtca ggctgagtaa gttcaaacat catatttaat tttcccaata ccctgtaagg   28200
aaattaaggc ttaggaatgg ggcttggcca gcaagtggca gggccaaggc tccaggtctg   28260
tttggtctca gagtccatgc tcttcaccag gccacactgc tgccttccct gccattgagc   28320
atccacaggc tgccctgcac cacaggcctc gtggcttcag aattttgtat cacaagtgtc   28380
tttgtaggcc accataatgt gcaggaagca ggtgatgtgt gaaagtggtc ctgagccttc   28440
catgtgtggg gcaaagcagg gccttctaag cttctcatga gctcagcaac agtggttttt   28500
actgcagccc cacaacctaa gagcatggaa ccagagcctg ttgttcagag gacaaggatt   28560
aggctctgag aaaggaaggt catttggtgg atttagttca tccttttgct cttcctgtgt   28620
ttggtttctg gggctggaga gattaatctg acctggtttc tgctcccaag gagctcgggc   28680
tgaagggctg tctgttagtg ggagtccaat gagggaggca gatgatgaaa gggatggtga   28740
```

```
gtggtttcag agagggctgt ggacacatag gggaggggag ggagccccca gctgagaaag  28800
gccaggctag aattcagtct ctggataccc catcaggcct cttcttctcc atccaggctg  28860
cctcagcagc agagtaagga caagtgggta gggttacccc ccttcccaga gagaccagcc  28920
ctctaagcag tggggcctgg agctcagccc cctctggtcc ttttaccoct caagagagtt  28980
agagatttct ggaagctagg tttccaggat gctcagacca tagcctaaac ctcatcgtcc  29040
ctatctggcc cacctggagc atccacctag aggatgccac tagaggagcc tggatgcctg  29100
tagagtctgg ggggctagag tcttcccttt tcaggcccaa gaaagggaat caggcagact  29160
gctgaacagt aagtatgact ttgtaggcag cctttagaca tagctattca ccaagctacc  29220
gtaagctttt cacagtttgc ttttaacagg ctcttgtagg ctgcacatgc ttccctagaa  29280
acttgtcttc ccttctgcga tgtcacaccc ctaagctggt cctgaaaaat tggacatctc  29340
gtcactctgt attcactgtt cctcccaaca agagagttgt accctgtttt tagctaccct  29400
ggggagaggc tggctcagga gtctagaaca gggctagatt gggggcaac aaggggctac  29460
catttccctc cctttaggct catggagagt ctacatccag ccttatcttc tcccatggga  29520
aaccaaagga ggctcaacat ggtgagaaga gagcatgaca tccagagcca ggcagcctac  29580
agcacctggg accaccaggg aatgggcaca cagcaagggt tggcctccct tcttgggcag  29640
tggaaaaagt cctagaagga gtccatgctt ctcccaccaa acatgagtac ctgctgccct  29700
tgcccttgtg ctgaatgcca aggaccaaag aagatgcctc cccacccagt gtgggaaatt  29760
cacaggcaag agatgatatg tagatagtat gatattgggg aacacttctt gaagagctga  29820
ggtctgagat aggccttaaa ggttgggtaa aaaatggaaa gagagaagcc ctgctgaggg  29880
cagctagtgg cgagccatga gataaagcag gcatggcaca agctctcctt cctttctgtg  29940
ccaggctaga ttagtctctc ttatgaccta caggcccaga acatggtgac cagtggaagc  30000
cagcccccag gcaagtcttc caagtgtgct gttagggttt tttttttttt acttttgaga  30060
cagagattcc ctctgttgcc caggttgcag tgtagtggcg cgatcatggc tcactgcagc  30120
ttcaaactcc tggcttaagg agtcttccca tctcagcctc ctgagtagct gggactacag  30180
gcacatgcca ccttgcccag ctaattttttt aaatttttttt gtagagatgg agtctcgcta  30240
tgttgcccag gctggtcttg aatttctgag ctcaagcagt ccaccacctc agcttcccaa  30300
agtgctggga ttacgggtgt gagccactgt gcctggctgc tgaagttttt gaagacaggg  30360
aggctgatgg gctctgcgct ttggcctggg acttcctgga ttgccgttat gttggaaggg  30420
agccagccct cctcctgggc aagtgtcccc tctccggtcc ctctagtgat ggtctgggac  30480
tttggtgaat ttctaaagcc taatacagag aacggactgt agagtcagac ctgtgtttga  30540
atcctggctc tgccactgtc ctgctgggtg accttgggca agttatctcc cccttgagcc  30600
tcagtgttct tatctctaaa atggggcaaa gtcaccctgc cttacacttg agacagtggc  30660
tcagccccag tcttgagatg cagaggcact gggtaggtgt tccctcccct tatccacagt  30720
gtctgggctg ggtgctggca tggggcgca cacaaggagg ggacagtaag agcagcttca  30780
caagaagctg aagcctatct cctttggtgc tcctgtccag ataacatgga gcccatgggc  30840
ccctcgatgc caggacagtc catcagagtc tgggagatga ggctcctctt gtcccaggaa  30900
tctgctccta cctgggctga acattcctgt agctatttct cagggtttgt gggcccatg  30960
cccatggccc tgggtgtgcc tagcttagtg ccacagtaaa cactcactcc atccaccatg  31020
gcccagaggg gagatgaagc ccagtaggac ctgacctgtg gccatctgcc ccccaggagt  31080
ggcctgcagt gccatcctca tgtacatatt ctgcactgat tgctggctca tcgctgtgct  31140
```

```
ctacttcact tggctggtgt ttgactggaa cacacccaag aaaggtaagt gcaaggcctc    31200
ccttgcccca cctctcattc tagggatgct cttccccctg cacaagctga agggcctcat    31260
cctgagtgct gtttcttta  acacccactt tgtgaaaagc actggactag tccttttggg    31320
gggaggttaa aagcccctca aagggcactg ttctggtcct gacaagagtt cacactcagt    31380
cgagggtttg cataacatga aggaatgaat gtggaaaggg gcctgatggg aaggggggcat   31440
ggtgcatggg gtgatggtca cctgcttggg tttcacactg gccctgtctt gtctgccttg    31500
cccaaatgta cccccacccc caccaactct gtattttatt ccctggaagg tggcaggagg    31560
tcacagtggg tccgaaactg ggctgtgtgg cgctactttc gagactactt tcccatccag    31620
gtaaagtgct gtgagtgttg ttttgggagg gtgggaatgg atgggaaatc tgaactcagg    31680
ccttaaccca cccacaggga agcaagttta gaccaagttg gtctcttcat ttcctttcta    31740
ctgtgtcact ggctgtgctg gggaccccac tgctcttctg agtatccatc ttctttgggc    31800
cagccctgag gtcctgacag ggaaatggtg gctcagtttg gctttcagtc tcagctctgt    31860
ctggcccctg cctggtctgc aagctgggct ggtgaggcac agccatctgg ccctgatgca    31920
tgtgggcaat cctggtgaat tgaggataac tctggcagga tcctgaaggt tttccccaca    31980
ggggaaagac ctgtctggcc agctcactcc acaccccagc tccagcacac cctagctgct    32040
gagtaccctg cagaaggtag gggtgctgaa gagtggaggc agcacgtgaa tgtgaaagag    32100
ttctgtgcag ggtgcagggt ggtgtatatt tgctgttgtg agtcagtgac tgagatcctg    32160
gtgtgttgcc tgggggcagt ggctgggtaa ccctgcatcc ttcactgcat tcggtatttt    32220
gggggtggca gggccagctc cttctgctca tccttagcct aagcccagtc ttcccgggac    32280
cttcctgctc ctcagggtca gcgttccttc tccttttcct gaccccatct ctctaactgc    32340
agaaaatttg aagctgtttt tgttgggaga aagttgcatc ataggaccca accctctaat    32400
tttggaggta aagaaactga gcctcagaga tgggcaggac ttgtccaggc tgcatagtct    32460
agtatgatgg caacattgca accaccatcc aggcttattg aattcagggc ccaggttctt    32520
ttccactgat ttcctactgc ctgtttctct gggagagatt caatccctgg atttccccat    32580
tggattgatt ccagcttcct gggtctccct ctcccccgtt gctgctggag atctcagttt    32640
aagttcctgc cctgtcactc catttattaa cctgccacca ttgctccctg tccagtgcag    32700
ggctgtgctg ggcatgggga cacaagtcag ccctgccctt ggggtgtcta ttgcatcctg    32760
atagactttg tcactttctg ccatgggggcc atgggcagac tttctcaagc ctgctgagcc    32820
tcatctgcaa aatggagctg tctgtatgat gaaaagtaat cagttctgat tgggtgggag    32880
tgatgataga ctgttctttc tgctttctct ctcacctcag gggccaggct ccagtgttct    32940
ctgttgccac tgtggcctgg tcctctggaa gtctccagga ggccagtagc cccatccact    33000
tagaacagga tgacctgatg attgttggtc agacctggga caggcaggtg tccttttgcta   33060
tctgatctcc acccttccaa aagaaccaaa caaacccctg tgtccttctc acatctctgt    33120
tccaagaagt cagctgggag ttggagcctt agggcacata caacctggcc ctgtgagggc    33180
tccctggggc actaggacaa aagccaaact gggcccgagg caggctgggg tgttgagcct    33240
caacccgggg cttaggctga tcaacccggg gcttaggctg agcctgcctc tctccctctg    33300
ggcctcaatc tccccttcac ttggccttgg tgatctgaca tcaggtctga cactctatgg    33360
gggtgtgtgt gaccctcctg tcccaccccc ttttcctggc ctcttgccag taatcatgta    33420
atgaagatct gccgctgtac ccacccgccc acctactccc ttcctggtgg gactctggtc    33480
```

```
tttgctgcca gaacagctca tctggcccag agtgtatccc ttctgttggc acaggtgggg    33540
ttcttgtgtt agcaacagcc accgagacca ccagccacct ggaagaggag cagacagtgc    33600
cccacatcac ctctccccaa agtgtaggca gaatccttgg agaggagact aggaaacact    33660
ctctctaagc ttagaatcac ctgtccatct gcctcatttc actgataggc ttactgaggc    33720
acagagagga gggactatcc caaggtcaca aagcttaagt agtagcagga ctagtgtagg    33780
aaccagggct gtctgctttg ggcccatgg tcttactcct gtgttacttt caccatcacc    33840
atgccgtgct gtgtaaactt aagcaagcct ttgctcttct gtgggtctga attttttcct    33900
ctatgcactg ctgtggtggg acaagcctat ctgagcacct tgcctctcct gggagggagg    33960
gtataaagag tgacttgata ggaatgtgtc ccagactgac attagcgagc aggccgggcc    34020
tgggcatcgt gttgggctgg gactttgcca cgggaaacag gcagcaagag gacacaagag    34080
caggcatgtc aacagaacct tcattggcgg tatccttccc ctccttccag aacggacatt    34140
ctctccagcc ctggggagg ggagtgtgac atgaaaacag atcagagctg gtcagatgcc    34200
tacattcttc tgggtcctac agcaagggca ttgacttgca ctgtgtccca aggcacctca    34260
ttcaaccaaa tgtcccatca gagccttggg gagggaggaa atgatttaaa gagccacctg    34320
gggcccactg ggtgacacat cttcatccag cagcccaggg aaaagtgcag cgactggcct    34380
gctccagatg tgcaggataa tttgctgtga cctccacagg ggaattgcag ctccctttttc   34440 taggcctcag cttcccccccg tcatccaagg aatggcttag acctttcagg gctctgccag    34500
cccatgcagt gctgtgggtt cctggttatc ggcccagtgg gaaggtcggg ggagccatag    34560
gaaggggaca aaaagatgct gcacggcgtg atggtcacct gccagggtaa ctatcccagg    34620
cctggccatc agctcaggag caagtttcca agtttcccac ctggtattgg ctgccccagc    34680
tcttccctca atgcctgcct gccttttttca tcaaaactag cacaaggaac ttttttaattc   34740 cagcttcact gagagctaac ttggtgggca gacctgcttg ttaggcaaaa cattggaaca    34800
gcaatcttaa cagagctcat gtaaacgaga ttttgagatc tgctcgctgc cccgagcccc    34860
actagctatg gattagactg ctgctgtttc ccatttattt ggggagtagc tgagagttgg    34920
tttggttttt gagcaacttt aatctgtttg ccaagggcaa agcgggagaa agagcatcag    34980
tgccccaagc agtggggatg agagtgaggg agtcttgctc acatttgcac agactggcag    35040
cgtcagagct gggagtggtg ccagccagcc ttttccatcc cctctgtcac ctgaagattt    35100
gcatttcaat tttccaaggc cagccaccag caccctctcc cccagagctg cacacaagtc    35160
cttcagctct gccaggaggc tcccaaatct ggagtcacag aaaacctggg ctcttgacat    35220
tctgctggtg gccagtgact ctgcttccag ctggcaccag tgcagggaag gggcactttg    35280
cagcactcag gtgggagtgt cattgatgtc acctcttttg aggcagggca gccaaaaaga    35340
ccaacgtgtt cattccttgt tatccaggaa ttgtatttct agaagtttgt ttcacaaaag    35400
caatcagata tgtggacaaa gataaggtat ttattgaagc attacttcta agagggaaat    35460
tttggaagct tttaaaatgt ccatcaatca gggtttgagt cagtgctgtt acatgcatga    35520
gagctgtgct gtagaataca aatgcagcca cgagaagata tggaactgag ggattttgat    35580
aaggacagat agctgtatgt ttggtagaaa atgatataaa aatgatatca acccatataa    35640
cctcaatttt gtgggttttg aaaaagagca tgtatatttt tgagtagaaa aaggactcaa    35700
tgcgtcagat ggttttatct ggatggaaat attatggatt ttttaaattt tcttttttgct   35760 ttcctatatt ttttaaattc tctaggagtt tctcttcttt tccctctccc ctcccctccc    35820 ctccccctccc cctcctccgt tcctctcccc tctcctccgt tcctctgccc tctcctccgt   35880
```

-continued

```
tcctctcccc tctcctctcc tctcccttct ctcctttctt cctttccttc tttcctttct    35940
tctcactctg tcactcaggc ttgagtgcag tggtgcaatc tcggtttact gcagcctctg    36000
cctcctgggc tcaagccatc tttccacctc agcctcctga gtagctggga ccacaggtgc    36060
gtgccaccat gcccagttaa tttctgtatt tttgtagaga taagcgtttc accatgttgc    36120
ccaggctggt ctcaaactcc tgagctgaag caatcctccc accttggcct cccaaagtgt    36180
tgggataaca ggcatgagcc accatgcctg ccctattat ttttctaatc agaataaaaa    36240
tgatgttttt atgagcagaa taccttact cattgtctct ctcagcctct tccaccccca     36300
tcacattcct tgtaacacag ggtaggtgtc acaggctttg cctctcatga ctcagggttt    36360
agggacactg catcacccac cccttcaagc accagcccca gggcaggagg tgggccctga    36420
ggaagccaat catcgtttag agcatcccag tgtccttagt accacaggtc aggtcctcag    36480
ctgctgcagc cttacaacta acctctaccc caggctggct ggcacagggc tgtcgcttgt    36540
cctgtcttgt ccttcctgcc ttagaacctg aactgagccc agctgactgt gggaaagttt    36600
ccatttgggc cagctgcagt gtcccttttc caggccaggg gagtaggagg tgggctgcct    36660
gtctcattct gtgagctgtg gaggagccca cagagcacag ggccaagtaa accctacctc    36720
caaggagctc acagtttgga gagactgaca gtggggcag agcttgcagc caaggccccg     36780
gttgccaaac tcaggaactt ggactttact cacatgaagc cagacacact ctccagtcta    36840
agagtgacaa gggttggatt tgagttttag aataatcact ctggctgttg cgaaaaggat    36900
gggcccagag ggagggaagg caggaggctg gcagagtgca aagaagagct gctgtgtgca    36960
tggctgaaga ctgagaggaa caagggcaaa cattgcccac cccttcccag agacccacag    37020
tgcaaatggt gactgcccaa caccagcact gtggccctgg ggatgagagt ctgaggtaag    37080
gtgtggagat tcattgcagc cctcaggccc atggaggtcc aggggaaatg acacatccaa    37140
tccctcccta ccctccgggt atgccccggt atccctctcc cagccagttt cctctgaccc    37200
aaggtcatcc ttgcagctgg tgaagacaca caacctgctg accaccagga actatatctt    37260
tggataccac ccccatggta tcatgggcct gggtgccttc tgcaacttca gcacagaggc    37320
cacagaagtg agcaagaagt tcccaggcat acggccttac ctggctacac tggcaggcaa    37380
cttccgaatg cctgtgttga gggagtacct gatgtctgga ggtaagaatc cacccctgt     37440 gctcctgctg ggcactgttg tcaaggcctg agcctctcca tcgggcaggg tgacacaggg    37500
agccaacaca ccattccttg gtgctgggcc tgcattggga gatgcaacct gcttcagaca    37560
tggtgggtca gggctgagga ggagagctgt ccatatggtc ttgagaattc aactcggata    37620
acatcttccc taggaggcct tctttgaccc ccttttctgg gaccccccag cccttgtgtt    37680 gcctttgta caacctgatt gttgtccatg gcactgtaat tgtccacctg cctgagacct     37740
cccaccagac tgatgcattg ggatccccaa cacctcgcac cgacttggca gaattagggc    37800
cctgggaatg tttgccaaat gcatgagttc ccaaaacaac cttgtatcat tagctgcatt    37860
ttacagatga ggaaactgag gctcagaaaa atgaatagct tacacagaac cagcaaactc    37920
caaaggggct gggctaggtc tggggcccag gtccagggtt ctttatgttt tatacctgac    37980
tgtgtgccgg ggatggggag tggatccatg ggcaaccctg actgttgcgt ccttccctcc    38040
cctcaggtat ctgccctgtc agccgggaca ccatagacta tttgctttca aagaatggga    38100
gtggcaatgc tatcatcatc gtggtcgggg gtgcggctga gtctctgagc tccatgcctg    38160
gcaagaatgc agtcacccct gcggaaccgca agggctttgt gaaactggcc ctgcgtcatg    38220
```

```
ggtgagtgcc tccctacaca cacacacacc cctccagtgc ccctcagccc agggcagcag   38280
actccttggc ccctgaagac aggacccaga ccccaggaag gcatggaagg gagtcagtca   38340
ttctgttagg gaggggatgt tggagcccag actgcacagt gtgggccaag tttgcccatg   38400
tgtgtctggg tgggcacaga tgcaacctgt ggcctgtggg cccttgcagg tgggccgaga   38460
gtccaggctt atatgcagga ctggaccacc tggggccaga atatatcatt ttgctgggag   38520
accaggaggt caggaaggag ggtggtgtgg aatgtggctg ggggacagca gctgttttct   38580 ctgtccctg gggaccttac ctcaggcttt ggaagaagag gctgccctgc aggctcagcc   38640
ctgggccagc ccctggggac acattcatat tggacccagt ccctgccttc agggagcacc   38700
aagggtgggg gagggtagag ggatggacag tgacaacaca gtgtgctgag actgtgaaac   38760
aatggtgagt ccagggctga gagaggcctg gtttggtgga gggaccaaga gaacttcctg   38820
gcagaggcag gccctgcagg aagaggtgga aaacaggcat tccagagcag ggcgctcagc   38880 cttcccttg cctgggggac ccagagctct gatatgctcc ccagtcccta gcagtggggc   38940
agaaggccca tcagaacctg gtagagaggg atcatgtgaa cttgggacac ccaggtaatt   39000
ctggtacacc cagctggggg aggggatgc ttggccagtg tccagggcct ctaggctgac   39060
atagaaactg aagccagtaa gtagggtatg acagaccctg gcctctccct tccagagctg   39120
acctggttcc catctactcc tttggagaga atgaagtgta caagcaggtg atcttcgagg   39180
agggctcctg gggccgatgg gtccagaaga agttccagaa atacattggt ttcgcccat   39240 gcatcttcca tggtcgaggc ctcttctcct ccgacacctg ggggctggtg ccctactcca   39300
agcccatcac cactgttggt aagcccctag cctgcagacc aagggctgtc ctgaacacag   39360
ggtgccatac agctaatcag cagtagagac gggattccaa tgcaggccac ctggctctga   39420
tggccatgcc cttagccatg aggactttga agtgttgggt gctgatattg gtcaggaggg   39480
gtagtagtag gagtcgggga attgagccta tgggatgaac caagctctgt gataagtgag   39540
gaaagaaaat ctgcagtctc tgggtttgca gcacccacta gtctatcagg gaagactatt   39600
gcagcaaaga ctagtggggg aatgtgatga ggatgcgcag gtgctctagg gagtcatagc   39660
ggaccccagg gaggaggtaa ctcttgcact gctaactgat aggaattatc tagcaaaata   39720
gaggaggaag agaatttta tcagaaacaa tagcctacgt gaagttcaga agcaagattg   39780
tgtagttttt ttgaagaaca gaaagaaaaa cattaatatg actgcagcat agacctgtca   39840
gaagagtgga aaacactggt tgcacttggc cctcgtctgt gttgttttgg gtgtatttgg   39900
gaccatttag aggattctaa agaattacct attgtaggtg tgtgtgtgca tgttaatgga   39960
tcccccagga gcacatgggc ccttggcagt ggacttgagg ggccaaagct cacacagatc   40020
ctttgcgttc ctaggccagg tgtcctgcct tgtacttta ggtagagaca aagcaacagg   40080
gaggcagcag gaacatttcc atgcacaggt gtggctgggg aggggctggg tcctgtgggc   40140
aatgtgaagg aatttgctct tcaccttgag aatggagagc caccagagag tgtttgggag   40200
gggaagttca gatttgcatt taaaaatgat ccttggagct gctggatgga agatgggtta   40260
gaaaaatgga agccacgaga ccagcccaga gactgttttg gtagccagtg gcttggacca   40320
agggagtagc agtggagatg aagagatgt gcatgatttg ggaaaaattt cagaaatagc   40380
attggcagga cataggaatg gattgggtat ggagatgcag caggataaga aaataaagca   40440
acgcacagat cataaatgct ggtctactcc ctcctctcct gcccttaacc acacttttta   40500
tttttttttt tttattttt gagacagggt ctcattctgt catccaggct ggagtgcagt   40560
ggcgcaatct cggctcactg taacctctgc ctcctagtct caagcgatcc tcccacctca   40620
```

```
gcctcctgag tagctgggac tacaggcgtg caccaccaca cccagctaat tttttgtatt    40680 ttttttttggt agagacgatt ttcaccatgt tacccaggct ggtcttgaac tcatgagctc    40740
aagcaatctg cgggtctttg cctctcacag tgctggaatt acaggcgtga gccaccactc    40800
ctggcctaca cttttttaaag catgtcacat tccttgcaga atccttagaa aaccccctatg    40860 aggaagaatc cccatgtgac agatgaggaa actgagggtc agagaggcag gaatggcttg    40920
cccagagcag agcaaaagca aagatgtttta cttgatcccc tgactctcat agaccctcct    40980
agcagaatgc agtgggttca accagtcttg atcccatctg cagcttagca cctggtggcc    41040
tcgggtgggt cccttcacat gcccctgggc ctcagtcttt tcatctgtaa tagggggacaa    41100 ccagagatgc agcacataaa gcatttggca cagttccttc cacatggcgg gcccacagcc    41160
cagcgtcacc accttcagca tcatggtgga tgcccagggg aagggtgttg actaaccaga    41220
agcctctgcc ctgtccctgc agtgggagag cccatcacca tccccaagct ggagcaccca    41280
acccagcaag acatcgacct gtaccacacc atgtacatgg aggccctggt gaagctcttc    41340
gacaagcaca agaccaagtt cggcctcccg gagactgagg tcctggaggt gaactgagcc    41400
agccttcggg gccaattccc tggaggaacc agctgcaaat cacttttttg ctctgtaaat    41460
ttggaagtgt catgggtgtc tgtgggttat ttaaaagaaa ttataacaat tttgctaaac    41520
cattacaatg ttaggtcttt tttaagaagg aaaaagtcag tatttcaagt tctttcactt    41580
ccagcttgcc ctgttctagg tggtggctaa atctgggcct aatctgggtg gctcagctaa    41640
cctctcttct tcccttcctg aagtgacaaa ggaaactcag tcttcttggg gaagaaggat    41700
tgccattagt gacttggacc agttagatga ttcactttttt gccctaggg atgagaggcg    41760 aaagccactt ctcatacaag cccctttatt gccactaccc cacgctcgtc tagtcctgaa    41820
actgcaggac cagtttctct gccaagggga ggagttggag agcacagttg ccccgttgtg    41880
tgagggcagt agtaggcatc tggaatgctc cagtttgatc tcccttctgc caccccctacc    41940 tcacccctag tcactcatat cggagcctgg actggcctcc aggatgagga tgggggtggc    42000
aatgacaccc tgcagggaaa aggactgccc cccatgcacc attgcaggga ggatgccgcc    42060
accatgagct aggtggagta actggttttt cttgggtggc tgatgacatg gatgcagcac    42120
agactcagcc ttggcctgga gcacatgctt actggtggcc tcagtttacc ttccccagat    42180
cctagattct ggatgtgagg aagagatccc tcttcagaag gggcctggcc ttctgagcag    42240
cagattagtt ccaaagcagg tggccccccga acccaagcct cacttttctg tgccttcctg    42300 aggggggttgg gccggggagg aaacccaacc ctctcctgtg tgttctgtta tctcttgatg    42360
agatcattgc accatgtcag acttttgtat atgccttgaa aataaatgaa agtgagaatc    42420
ctctatgagt tattgctggg gctgcatctg catctgctgc tgacacctgg ggaagactgg    42480
gtccccagct ggctgccctc tgagccctct agccccttgc acctttggcc cacatgaccc    42540
tgccatggtg tgtaagttac ctgtcactgt gtaacaaact acttcagagc tcagtggctt    42600
ccaacagcat ctgttgtctc ccagttccaa gtcacgattt gaggcttggc ttggtcctcc    42660
actcagggtt tctcacaggg ctgcagttgt cttggagccg ggctgaggaa ggatccactc    42720
ccaaggccgt tcctgcagtt gttcgcagga ttgacttcct cactggctgt tgacagaggc    42780
cactttcagt tccttgccac atgggccttt ccatgggta gct                       42823

<210> SEQ ID NO 19
<220> FEATURE:
```

```
<400> SEQUENCE: 19

000

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ctcctgccac ctttcttggg                                           20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tggatgggaa agtagtctcg                                           20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ccagctggat gggaaagtag                                           20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
cttcaccagc tggatgggaa                                           20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
tgtgtcttca ccagctggat                                           20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ggttgtgtgt cttcaccagc                                           20

<210> SEQ ID NO 26
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 26
cagcaggttg tgtgtcttca                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
gtggtcagca ggttgtgtgt                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tcctggtggt cagcaggttg                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
atagttcctg gtggtcagca                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
aagatatagt tcctggtggt                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
atccaaagat atagttcctg                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
```
gtggtatcca aagatatagt                                        20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
aaggcaccca ggcccatgat                                        20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cctccagaca tcaggtactc                                        20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gcattgccac tcccattctt                                        20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
tgatagcatt gccactccca                                        20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gatgatgata gcattgccac                                        20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
accacgatga tgatagcatt                                        20

<210> SEQ ID NO 39
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 39
ttgccaggca tggagctcag                                             20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
tggacccatc ggccccagga                                             20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
tcttctggac ccatcggccc                                             20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gaacttcttc tggacccatc                                             20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ttctggaact tcttctggac                                             20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ggcaccagcc cccaggtgtc                                             20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
agtagggcac cagcccccag                                             20
```

```
<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
cttggagtag ggcaccagcc                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
cagggcctcc atgtacatgg                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ttcaccaggg cctccatgta                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
agagcttcac cagggcctcc                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
aacccacaga cacccatgac                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
taaataaccc acagacaccc                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 52
tcttttaaat aacccacaga                                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
acaaaagagc atcctcctca                                                    20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
actataaatg cttcagtcca                                                    20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ttgcacttac ctttcttggg                                                    20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
agcactttac ctggatggga                                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
tcagtgaaat gaggcagatg                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ctcaaaagag gtgacatcaa                                                    20

<210> SEQ ID NO 59
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ggattcttac ctccagacat                                          20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
caggtcagct ctggaaggga                                          20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ttcccctgga cctccatggg                                          20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gtggcgcgag agaaacagcc                                          20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gccagggctt cgcgcagagc                                          20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
agggtcttca tggctgaagc                                          20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
```
aggaccccgg agtaggcggc                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
acccactgga gcactgagat                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
gggcagatac ctccagacat                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cggttccgca gggtgactgc                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
aaggctggct cagttcacct                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gggagttggc cccgaaggct                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gctggttcct ccagggagtt                                               20

<210> SEQ ID NO 72
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 72
acttccaaat ttacagagca                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ccacctagaa cagggcaagc                    20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
gggaagaaga gaggttagct                    20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
tcacttcagg aagggaagaa                    20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ccttcttccc caagaagact                    20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ctaactggtc caagtcacta                    20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ggcaaaaagt gaatcatcta                    20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ttcgcctctc atccctaggg                                          20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
ggcttgtatg agaagtggct                                          20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tttcaggact agacgagcgt                                          20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
ctccgatatg agtgactagg                                          20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ctcatcctgg aggccagtcc                                          20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ccatcctcat cctggaggcc                                          20

<210> SEQ ID NO 85
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 85
gtgtcattgc cacccccatc                                                         20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
acctagctca tggtggcggc                                                         20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
accagttact ccacctagct                                                         20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
gtcatcagcc acccaagaaa                                                         20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gtgctccagg ccaaggctga                                                         20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
accagtaagc atgtgctcca                                                         20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gaggccacca gtaagcatgt                                                         20

```
<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gtaaactgag gccaccagta                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
cttcctcaca tccagaatct                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tgctcagaag gccaggcccc                                              20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
acctgctttg gaactaatct                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
gaaaagtgag gcttgggttc                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
aaaagtctga catggtgcaa                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 98
ccaccctaga tgagcagaaa                                             20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ggtaggtagc cgctgccacc                                             20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
agagctgagg taggtagccg                                             20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
gcgctgagct ccgggagctg                                             20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
aagccaatgc acgtcacggc                                             20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gagggtcttc atgctgaagc                                             20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
gttttcgctg cgggcagctt                                             20

<210> SEQ ID NO 105
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 105
gtttttccac cttagatctg                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
tgagatgacc tgcagctgtt                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
caggccactc ctagcaccag                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
gatgacactg caggccactc                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
ccacacggcc cagtttcgca                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
gggcagatgc ctccagacat                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
```

```
tcggttgaca gggcagatgc                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
gggactcagc tgcacctccc                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
cagatcagct ccatggcgca                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
cacctgcttg tatacctcat                                              20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
gaagaggcct cggccatgga                                              20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116 ggctcccca cgacggtggt                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
ggtcgggtgc tccagcttgg                                              20

<210> SEQ ID NO 118
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 118
agtctctgga aggccaaatt                                              20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
ggctgggtca gttcacctcc                                              20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
ctcccaggag ctggcacgcg                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
atgcactcaa gaactcggta                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
actgactctt cccttcttaa                                              20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
acacactaga agtgagctta                                              20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
cctccacctt gagcaggaca                                              20
```

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
caccaaggcc cataaatatc                                              20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
agaaaccacc aaggcccata                                              20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
gccagggcca agtgtctgtc                                              20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
tggagtcact aaggactgcc                                              20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
gggacatggc ctctgcctct                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
ggtacgagga acccgacctg                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 131
gccagctgtg ccctcagcct                                            20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
ccaagccggg cagtccagat                                            20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
gggtaggctc agattggaga                                            20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
cggcacctgt gggacagccg                                            20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
agagtgaaac cagccaacag                                            20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
gctcaggagg atatgcgcca                                            20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
aagcccttcc tcacaccaga                                            20

<210> SEQ ID NO 138
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
ggcacctctg tgaagagaag                                          20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
tcctggaccc agtgtgctgc                                          20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
cacacacgtg aggcttggtt                                          20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
atacaaaagt gtgacatggc                                          20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
tccatttatt agtctaggaa                                          20

<210> SEQ ID NO 143
<211> LENGTH: 20
<212> TYPE: DNA
<213> ORGANISM: H. sapiens
<220> FEATURE:

<400> SEQUENCE: 143
cccaagaaag gtggcaggag                                          20

<210> SEQ ID NO 144
<211> LENGTH: 20
<212> TYPE: DNA
<213> ORGANISM: H. sapiens
<220> FEATURE:

<400> SEQUENCE: 144
cgagactact ttcccatcca                                          20
```

<210> SEQ ID NO 145
<211> LENGTH: 20
<212> TYPE: DNA
<213> ORGANISM: H. sapiens
<220> FEATURE:

<400> SEQUENCE: 145
ttcccatcca gctggtgaag                                       20

<210> SEQ ID NO 146
<211> LENGTH: 20
<212> TYPE: DNA
<213> ORGANISM: H. sapiens
<220> FEATURE:

<400> SEQUENCE: 146
atccagctgg tgaagacaca                                       20

<210> SEQ ID NO 147
<211> LENGTH: 20
<212> TYPE: DNA
<213> ORGANISM: H. sapiens
<220> FEATURE:

<400> SEQUENCE: 147
gctggtgaag acacacaacc                                       20

<210> SEQ ID NO 148
<211> LENGTH: 20
<212> TYPE: DNA
<213> ORGANISM: H. sapiens
<220> FEATURE:

<400> SEQUENCE: 148
tgaagacaca caacctgctg                                       20

<210> SEQ ID NO 149
<211> LENGTH: 20
<212> TYPE: DNA
<213> ORGANISM: H. sapiens
<220> FEATURE:

<400> SEQUENCE: 149
acacacaacc tgctgaccac                                       20

<210> SEQ ID NO 150
<211> LENGTH: 20
<212> TYPE: DNA
<213> ORGANISM: H. sapiens
<220> FEATURE:

<400> SEQUENCE: 150
caacctgctg accaccagga                                       20

<210> SEQ ID NO 151
<211> LENGTH: 20
<212> TYPE: DNA
<213> ORGANISM: H. sapiens
<220> FEATURE:

<400> SEQUENCE: 151
tgctgaccac caggaactat                                       20

```
<210> SEQ ID NO 152
<211> LENGTH: 20
<212> TYPE: DNA
<213> ORGANISM: H. sapiens
<220> FEATURE:

<400> SEQUENCE: 152
accaccagga actatatctt                                               20

<210> SEQ ID NO 153
<211> LENGTH: 20
<212> TYPE: DNA
<213> ORGANISM: H. sapiens
<220> FEATURE:

<400> SEQUENCE: 153
caggaactat atctttggat                                               20

<210> SEQ ID NO 154
<211> LENGTH: 20
<212> TYPE: DNA
<213> ORGANISM: H. sapiens
<220> FEATURE:

<400> SEQUENCE: 154
actatatctt tggataccac                                               20

<210> SEQ ID NO 155
<211> LENGTH: 20
<212> TYPE: DNA
<213> ORGANISM: H. sapiens
<220> FEATURE:

<400> SEQUENCE: 155
atcatgggcc tgggtgcctt                                               20

<210> SEQ ID NO 156
<211> LENGTH: 20
<212> TYPE: DNA
<213> ORGANISM: H. sapiens
<220> FEATURE:

<400> SEQUENCE: 156
gagtacctga tgtctggagg                                               20

<210> SEQ ID NO 157
<211> LENGTH: 20
<212> TYPE: DNA
<213> ORGANISM: H. sapiens
<220> FEATURE:

<400> SEQUENCE: 157
aagaatggga gtggcaatgc                                               20

<210> SEQ ID NO 158
<211> LENGTH: 20
<212> TYPE: DNA
<213> ORGANISM: H. sapiens
<220> FEATURE:

<400> SEQUENCE: 158
tgggagtggc aatgctatca                                               20

<210> SEQ ID NO 159
<211> LENGTH: 20
```

```
<212> TYPE: DNA
<213> ORGANISM: H. sapiens
<220> FEATURE:

<400> SEQUENCE: 159
gtggcaatgc tatcatcatc                                                   20

<210> SEQ ID NO 160
<211> LENGTH: 20
<212> TYPE: DNA
<213> ORGANISM: H. sapiens
<220> FEATURE:

<400> SEQUENCE: 160
aatgctatca tcatcgtggt                                                   20

<210> SEQ ID NO 161
<211> LENGTH: 20
<212> TYPE: DNA
<213> ORGANISM: H. sapiens
<220> FEATURE:

<400> SEQUENCE: 161
ctgagctcca tgcctggcaa                                                   20

<210> SEQ ID NO 162
<211> LENGTH: 20
<212> TYPE: DNA
<213> ORGANISM: H. sapiens
<220> FEATURE:

<400> SEQUENCE: 162
tcctggggcc gatgggtcca                                                   20

<210> SEQ ID NO 163
<211> LENGTH: 20
<212> TYPE: DNA
<213> ORGANISM: H. sapiens
<220> FEATURE:

<400> SEQUENCE: 163
gggccgatgg gtccagaaga                                                   20

<210> SEQ ID NO 164
<211> LENGTH: 20
<212> TYPE: DNA
<213> ORGANISM: H. sapiens
<220> FEATURE:

<400> SEQUENCE: 164
gatgggtcca gaagaagttc                                                   20

<210> SEQ ID NO 165
<211> LENGTH: 20
<212> TYPE: DNA
<213> ORGANISM: H. sapiens
<220> FEATURE:

<400> SEQUENCE: 165
gtccagaaga agttccagaa                                                   20

<210> SEQ ID NO 166
<211> LENGTH: 20
<212> TYPE: DNA
<213> ORGANISM: H. sapiens
```

```
<220> FEATURE:

<400> SEQUENCE: 166
gacacctggg ggctggtgcc                                          20

<210> SEQ ID NO 167
<211> LENGTH: 20
<212> TYPE: DNA
<213> ORGANISM: H. sapiens
<220> FEATURE:

<400> SEQUENCE: 167
ctgggggctg gtgccctact                                          20

<210> SEQ ID NO 168
<211> LENGTH: 20
<212> TYPE: DNA
<213> ORGANISM: H. sapiens
<220> FEATURE:

<400> SEQUENCE: 168
ggctggtgcc ctactccaag                                          20

<210> SEQ ID NO 169
<211> LENGTH: 20
<212> TYPE: DNA
<213> ORGANISM: H. sapiens
<220> FEATURE:

<400> SEQUENCE: 169
ccatgtacat ggaggccctg                                          20

<210> SEQ ID NO 170
<211> LENGTH: 20
<212> TYPE: DNA
<213> ORGANISM: H. sapiens
<220> FEATURE:

<400> SEQUENCE: 170
tacatggagg ccctggtgaa                                          20

<210> SEQ ID NO 171
<211> LENGTH: 20
<212> TYPE: DNA
<213> ORGANISM: H. sapiens
<220> FEATURE:

<400> SEQUENCE: 171
ggaggccctg gtgaagctct                                          20

<210> SEQ ID NO 172
<211> LENGTH: 20
<212> TYPE: DNA
<213> ORGANISM: H. sapiens
<220> FEATURE:

<400> SEQUENCE: 172
gtcatgggtg tctgtgggtt                                          20

<210> SEQ ID NO 173
<211> LENGTH: 20
<212> TYPE: DNA
<213> ORGANISM: H. sapiens
<220> FEATURE:
```

-continued

```
<400> SEQUENCE: 173
gggtgtctgt gggttattta                                        20

<210> SEQ ID NO 174
<211> LENGTH: 20
<212> TYPE: DNA
<213> ORGANISM: H. sapiens
<220> FEATURE:

<400> SEQUENCE: 174
tctgtgggtt atttaaaaga                                        20

<210> SEQ ID NO 175
<211> LENGTH: 20
<212> TYPE: DNA
<213> ORGANISM: H. sapiens
<220> FEATURE:

<400> SEQUENCE: 175
tgaggaggat gctcttttgt                                        20

<210> SEQ ID NO 176
<211> LENGTH: 20
<212> TYPE: DNA
<213> ORGANISM: H. sapiens
<220> FEATURE:

<400> SEQUENCE: 176
tggactgaag catttatagt                                        20

<210> SEQ ID NO 177
<211> LENGTH: 20
<212> TYPE: DNA
<213> ORGANISM: H. sapiens
<220> FEATURE:

<400> SEQUENCE: 177
tcccatccag gtaaagtgct                                        20

<210> SEQ ID NO 178
<211> LENGTH: 20
<212> TYPE: DNA
<213> ORGANISM: H. sapiens
<220> FEATURE:

<400> SEQUENCE: 178
catctgcctc atttcactga                                        20

<210> SEQ ID NO 179
<211> LENGTH: 20
<212> TYPE: DNA
<213> ORGANISM: H. sapiens
<220> FEATURE:

<400> SEQUENCE: 179
ttgatgtcac ctcttttgag                                        20

<210> SEQ ID NO 180
<211> LENGTH: 20
<212> TYPE: DNA
<213> ORGANISM: H. sapiens
<220> FEATURE:

<400> SEQUENCE: 180
```

| | |
|---|---|
| tcccttccag agctgacctg | 20 |

<210> SEQ ID NO 181
<211> LENGTH: 20
<212> TYPE: DNA
<213> ORGANISM: H. sapiens
<220> FEATURE:

<400> SEQUENCE: 181

| | |
|---|---|
| cccatggagg tccagggaa | 20 |

<210> SEQ ID NO 182
<211> LENGTH: 20
<212> TYPE: DNA
<213> ORGANISM: H. sapiens
<220> FEATURE:

<400> SEQUENCE: 182

| | |
|---|---|
| ggctgtttct ctcgcgccac | 20 |

<210> SEQ ID NO 183
<211> LENGTH: 20
<212> TYPE: DNA
<213> ORGANISM: H. sapiens
<220> FEATURE:

<400> SEQUENCE: 183

| | |
|---|---|
| gctctgcgcg aagccctggc | 20 |

<210> SEQ ID NO 184
<211> LENGTH: 20
<212> TYPE: DNA
<213> ORGANISM: H. sapiens
<220> FEATURE:

<400> SEQUENCE: 184

| | |
|---|---|
| gcttcagcca tgaagaccct | 20 |

<210> SEQ ID NO 185
<211> LENGTH: 20
<212> TYPE: DNA
<213> ORGANISM: H. sapiens
<220> FEATURE:

<400> SEQUENCE: 185

| | |
|---|---|
| gccgcctact ccggggtcct | 20 |

<210> SEQ ID NO 186
<211> LENGTH: 20
<212> TYPE: DNA
<213> ORGANISM: H. sapiens
<220> FEATURE:

<400> SEQUENCE: 186

| | |
|---|---|
| atctcagtgc tccagtgggt | 20 |

<210> SEQ ID NO 187
<211> LENGTH: 20
<212> TYPE: DNA
<213> ORGANISM: H. sapiens
<220> FEATURE:

<400> SEQUENCE: 187

| | |
|---|---|
| gcagtcaccc tgcggaaccg | 20 |

```
<210> SEQ ID NO 188
<211> LENGTH: 20
<212> TYPE: DNA
<213> ORGANISM: H. sapiens
<220> FEATURE:

<400> SEQUENCE: 188
aggtgaactg agccagcctt                                          20

<210> SEQ ID NO 189
<211> LENGTH: 20
<212> TYPE: DNA
<213> ORGANISM: H. sapiens
<220> FEATURE:

<400> SEQUENCE: 189
agccttcggg gccaactccc                                          20

<210> SEQ ID NO 190
<211> LENGTH: 20
<212> TYPE: DNA
<213> ORGANISM: H. sapiens
<220> FEATURE:

<400> SEQUENCE: 190
aactccctgg aggaaccagc                                          20

<210> SEQ ID NO 191
<211> LENGTH: 20
<212> TYPE: DNA
<213> ORGANISM: H. sapiens
<220> FEATURE:

<400> SEQUENCE: 191
tgctctgtaa atttggaagt                                          20

<210> SEQ ID NO 192
<211> LENGTH: 20
<212> TYPE: DNA
<213> ORGANISM: H. sapiens
<220> FEATURE:

<400> SEQUENCE: 192
gcttgccctg ttctaggtgg                                          20

<210> SEQ ID NO 193
<211> LENGTH: 20
<212> TYPE: DNA
<213> ORGANISM: H. sapiens
<220> FEATURE:

<400> SEQUENCE: 193
ttcttccctt cctgaagtga                                          20

<210> SEQ ID NO 194
<211> LENGTH: 20
<212> TYPE: DNA
<213> ORGANISM: H. sapiens
<220> FEATURE:

<400> SEQUENCE: 194
agtcttcttg gggaagaagg                                          20

<210> SEQ ID NO 195
```

-continued

<211> LENGTH: 20
<212> TYPE: DNA
<213> ORGANISM: H. sapiens
<220> FEATURE:

<400> SEQUENCE: 195
tagtgacttg gaccagttag                                              20

<210> SEQ ID NO 196
<211> LENGTH: 20
<212> TYPE: DNA
<213> ORGANISM: H. sapiens
<220> FEATURE:

<400> SEQUENCE: 196
tagatgattc acttttttgcc                                             20

<210> SEQ ID NO 197
<211> LENGTH: 20
<212> TYPE: DNA
<213> ORGANISM: H. sapiens
<220> FEATURE:

<400> SEQUENCE: 197
agccacttct catacaagcc                                              20

<210> SEQ ID NO 198
<211> LENGTH: 20
<212> TYPE: DNA
<213> ORGANISM: H. sapiens
<220> FEATURE:

<400> SEQUENCE: 198
acgctcgtct agtcctgaaa                                              20

<210> SEQ ID NO 199
<211> LENGTH: 20
<212> TYPE: DNA
<213> ORGANISM: H. sapiens
<220> FEATURE:

<400> SEQUENCE: 199
cctagtcact catatcggag                                              20

<210> SEQ ID NO 200
<211> LENGTH: 20
<212> TYPE: DNA
<213> ORGANISM: H. sapiens
<220> FEATURE:

<400> SEQUENCE: 200
ggactggcct ccaggatgag                                              20

<210> SEQ ID NO 201
<211> LENGTH: 20
<212> TYPE: DNA
<213> ORGANISM: H. sapiens
<220> FEATURE:

<400> SEQUENCE: 201
ggcctccagg atgaggatgg                                              20

<210> SEQ ID NO 202
<211> LENGTH: 20
<212> TYPE: DNA

<213> ORGANISM: H. sapiens
<220> FEATURE:

<400> SEQUENCE: 202 gatggggtg gcaatgacac                    20

<210> SEQ ID NO 203
<211> LENGTH: 20
<212> TYPE: DNA
<213> ORGANISM: H. sapiens
<220> FEATURE:

<400> SEQUENCE: 203
gccgccacca tgagctaggt                   20

<210> SEQ ID NO 204
<211> LENGTH: 20
<212> TYPE: DNA
<213> ORGANISM: H. sapiens
<220> FEATURE:

<400> SEQUENCE: 204
agctaggtgg agtaactggt                   20

<210> SEQ ID NO 205
<211> LENGTH: 20
<212> TYPE: DNA
<213> ORGANISM: H. sapiens
<220> FEATURE:

<400> SEQUENCE: 205
tttcttgggt ggctgatgac                   20

<210> SEQ ID NO 206
<211> LENGTH: 20
<212> TYPE: DNA
<213> ORGANISM: H. sapiens
<220> FEATURE:

<400> SEQUENCE: 206
tcagccttgg cctggagcac                   20

<210> SEQ ID NO 207
<211> LENGTH: 20
<212> TYPE: DNA
<213> ORGANISM: H. sapiens
<220> FEATURE:

<400> SEQUENCE: 207
tggagcacat gcttactggt                   20

<210> SEQ ID NO 208
<211> LENGTH: 20
<212> TYPE: DNA
<213> ORGANISM: H. sapiens
<220> FEATURE:

<400> SEQUENCE: 208
acatgcttac tggtggcctc                   20

<210> SEQ ID NO 209
<211> LENGTH: 20
<212> TYPE: DNA
<213> ORGANISM: H. sapiens
<220> FEATURE:

-continued

```
<400> SEQUENCE: 209
tactggtggc ctcagtttac                                              20

<210> SEQ ID NO 210
<211> LENGTH: 20
<212> TYPE: DNA
<213> ORGANISM: H. sapiens
<220> FEATURE:

<400> SEQUENCE: 210
ggggcctggc cttctgagca                                              20

<210> SEQ ID NO 211
<211> LENGTH: 20
<212> TYPE: DNA
<213> ORGANISM: H. sapiens
<220> FEATURE:

<400> SEQUENCE: 211
agattagttc caaagcaggt                                              20

<210> SEQ ID NO 212
<211> LENGTH: 20
<212> TYPE: DNA
<213> ORGANISM: H. sapiens
<220> FEATURE:

<400> SEQUENCE: 212
gaacccaagc ctcacttttc                                              20

<210> SEQ ID NO 213
<211> LENGTH: 20
<212> TYPE: DNA
<213> ORGANISM: H. sapiens
<220> FEATURE:

<400> SEQUENCE: 213
ttgcaccatg tcagactttt                                              20

<210> SEQ ID NO 214
<211> LENGTH: 20
<212> TYPE: DNA
<213> ORGANISM: M. musculus
<220> FEATURE:

<400> SEQUENCE: 214
cagctcccgg agctcagcgc                                              20

<210> SEQ ID NO 215
<211> LENGTH: 20
<212> TYPE: DNA
<213> ORGANISM: M. musculus
<220> FEATURE:

<400> SEQUENCE: 215
tgcgaaactg ggccgtgtgg                                              20

<210> SEQ ID NO 216
<211> LENGTH: 20
<212> TYPE: DNA
<213> ORGANISM: M. musculus
<220> FEATURE:

<400> SEQUENCE: 216
```

-continued atgaggtata caagcaggtg                                        20

<210> SEQ ID NO 217
<211> LENGTH: 20
<212> TYPE: DNA
<213> ORGANISM: M. musculus
<220> FEATURE:

<400> SEQUENCE: 217
tccatggccg aggcctcttc                                        20

<210> SEQ ID NO 218
<211> LENGTH: 20
<212> TYPE: DNA
<213> ORGANISM: M. musculus
<220> FEATURE:

<400> SEQUENCE: 218
cgcgtgccag ctcctgggag                                        20

<210> SEQ ID NO 219
<211> LENGTH: 20
<212> TYPE: DNA
<213> ORGANISM: M. musculus
<220> FEATURE:

<400> SEQUENCE: 219
taccgagttc ttgagtgcat                                        20

<210> SEQ ID NO 220
<211> LENGTH: 20
<212> TYPE: DNA
<213> ORGANISM: M. musculus
<220> FEATURE:

<400> SEQUENCE: 220
ttaagaaggg aagagtcagt                                        20

<210> SEQ ID NO 221
<211> LENGTH: 20
<212> TYPE: DNA
<213> ORGANISM: M. musculus
<220> FEATURE:

<400> SEQUENCE: 221
taagctcact tctagtgtgt                                        20

<210> SEQ ID NO 222
<211> LENGTH: 20
<212> TYPE: DNA
<213> ORGANISM: M. musculus
<220> FEATURE:

<400> SEQUENCE: 222
tgtcctgctc aaggtggagg                                        20

<210> SEQ ID NO 223
<211> LENGTH: 20
<212> TYPE: DNA
<213> ORGANISM: M. musculus
<220> FEATURE:

<400> SEQUENCE: 223
gacagacact tggccctggc                                        20

```
<210> SEQ ID NO 224
<211> LENGTH: 20
<212> TYPE: DNA
<213> ORGANISM: M. musculus
<220> FEATURE:

<400> SEQUENCE: 224
ggcagtcctt agtgactcca                                              20

<210> SEQ ID NO 225
<211> LENGTH: 20
<212> TYPE: DNA
<213> ORGANISM: M. musculus
<220> FEATURE:

<400> SEQUENCE: 225
caggtcgggt tcctcgtacc                                              20

<210> SEQ ID NO 226
<211> LENGTH: 20
<212> TYPE: DNA
<213> ORGANISM: M. musculus
<220> FEATURE:

<400> SEQUENCE: 226
tctccaatct gagcctaccc                                              20

<210> SEQ ID NO 227
<211> LENGTH: 20
<212> TYPE: DNA
<213> ORGANISM: M. musculus
<220> FEATURE:

<400> SEQUENCE: 227
tggcgcatat cctcctgagc                                              20

<210> SEQ ID NO 228
<211> LENGTH: 20
<212> TYPE: DNA
<213> ORGANISM: M. musculus
<220> FEATURE:

<400> SEQUENCE: 228
ttcctagact aataaatgga                                              20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
ccttccctga aggttcctcc                                              20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230 ctgctagcctc tggatttga                                              20
```

```
<210> SEQ ID NO 231
<211> LENGTH: 19
<212> TYPE: RNA
<213> ORGANISM: Artificial Sequence
<220> FEATURE:
<223> OTHER INFORMATION: Oligomeric compound

<400> SEQUENCE: 231
cgagaggcgg acgggaccg                                                    19

<210> SEQ ID NO 232
<211> LENGTH: 21
<212> TYPE: DNA
<213> ORGANISM: Artificial Sequence
<220> FEATURE:
<223> OTHER INFORMATION: Oligomeric compound
<220> FEATURE:
<221> NAME/KEY: misc_feature
<222> LOCATION: (1)...(19)
<223> OTHER INFORMATION: bases at these positions are RNA

<400> SEQUENCE: 232
cgagaggcgg acgggaccgt t                                                 21

<210> SEQ ID NO 233
<211> LENGTH: 21
<212> TYPE: DNA
<213> ORGANISM: Artificial Sequence
<220> FEATURE:
<223> OTHER INFORMATION: Oligomeric compound
<220> FEATURE:
<221> NAME/KEY: misc_feature
<222> LOCATION: (1)...(19)
<223> OTHER INFORMATION: bases at these positions are RNA

<400> SEQUENCE: 233
cggucccguc cgccucucgt t                                                 21
```